United States Patent
Geller et al.

(10) Patent No.: US 9,790,495 B2
(45) Date of Patent: Oct. 17, 2017

(54) ANTISENSE ANTIBACTERIAL COMPOUNDS AND METHODS

(71) Applicants: Bruce L. Geller, Corvallis, OR (US); David Greenberg, Coppell, TX (US)

(72) Inventors: Bruce L. Geller, Corvallis, OR (US); David Greenberg, Coppell, TX (US)

(73) Assignees: Oregon State University, Corvallis, OR (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 14/713,857

(22) Filed: May 15, 2015

(65) Prior Publication Data

US 2015/0361425 A1     Dec. 17, 2015

Related U.S. Application Data

(60) Provisional application No. 61/994,750, filed on May 16, 2014, provisional application No. 62/099,046, filed on Dec. 31, 2014, provisional application No. 62/129,746, filed on Mar. 6, 2015.

(51) Int. Cl.
| | | |
|---|---|---|
| C12N 15/11 | (2006.01) | |
| C12N 15/113 | (2010.01) | |
| A61K 47/48 | (2006.01) | |
| A61K 38/00 | (2006.01) | |

(52) U.S. Cl.
CPC ...... *C12N 15/113* (2013.01); *A61K 47/48246* (2013.01); *A61K 38/00* (2013.01); *C12N 2310/11* (2013.01); *C12N 2310/3233* (2013.01); *C12N 2310/3513* (2013.01); *C12N 2320/50* (2013.01)

(58) Field of Classification Search
CPC .............. C12N 15/113; C12N 2310/11; C12N 2310/3233
See application file for complete search history.

(56) References Cited

U.S. PATENT DOCUMENTS

| | | | |
|---|---|---|---|
| 5,034,506 A | 7/1991 | Summerton et al. | |
| 5,142,047 A | 8/1992 | Summerton et al. | |
| 5,166,315 A | 11/1992 | Summerton et al. | |
| 5,185,444 A | 2/1993 | Summerton et al. | |
| 5,217,866 A | 6/1993 | Summerton et al. | |
| 5,506,337 A | 4/1996 | Summerton et al. | |
| 5,521,063 A | 5/1996 | Summerton et al. | |
| 5,698,685 A | 12/1997 | Summerton et al. | |
| 6,245,747 B1 | 6/2001 | Porter et al. | |
| 6,965,025 B2 | 11/2005 | Gaarde et al. | |
| 6,969,400 B2 | 11/2005 | Rhee et al. | |
| 7,625,873 B2 | 12/2009 | Geller et al. | |
| 7,790,694 B2 | 9/2010 | Geller et al. | |
| 8,067,571 B2 | 11/2011 | Weller et al. | |
| 8,076,476 B2 | 12/2011 | Reeves et al. | |
| 8,299,206 B2 | 10/2012 | Fox et al. | |
| 8,314,072 B2 | 11/2012 | Geller et al. | |
| 8,536,147 B2* | 9/2013 | Weller ................... | A61K 48/00 514/44 A |
| 9,249,243 B2* | 2/2016 | Weller ................... | A61K 48/00 |
| 2004/0029129 A1* | 2/2004 | Wang ................... | C07K 14/195 435/6.18 |
| 2005/0288246 A1 | 12/2005 | Iversen et al. | |
| 2006/0241075 A1* | 10/2006 | McSwiggen ....... | C12N 15/1138 514/44 A |
| 2006/0270621 A1* | 11/2006 | Christiano ........... | A61K 9/0014 514/44 R |
| 2007/0049542 A1 | 3/2007 | Geller et al. | |
| 2008/0194463 A1 | 8/2008 | Weller et al. | |
| 2010/0016215 A1 | 1/2010 | Moulton et al. | |
| 2010/0234281 A1 | 9/2010 | Weller et al. | |
| 2010/0261777 A1* | 10/2010 | Shaw .................. | C12N 15/102 514/44 R |
| 2012/0040460 A1* | 2/2012 | Rigoutsos ............. | C12N 15/111 435/375 |
| 2012/0122769 A1 | 5/2012 | Iversen | |
| 2012/0213663 A1 | 8/2012 | Atieh et al. | |
| 2012/0289457 A1 | 11/2012 | Hanson | |
| 2012/0296087 A1 | 11/2012 | Sinha et al. | |
| 2013/0197220 A1 | 8/2013 | Ueda | |
| 2016/0106857 A1 | 4/2016 | Geller et al. | |

FOREIGN PATENT DOCUMENTS

| | | |
|---|---|---|
| KR | 10-2013-0005208     * | 1/2013 |
| KR | 2013/0005208 A | 1/2013 |
| WO | WO 93/01286 A2 | 1/1993 |
| WO | WO 2004/097017 A2 | 11/2004 |
| WO | WO 2006/085973 A2 | 8/2006 |
| WO | WO 2008/008113 A1 | 1/2008 |

(Continued)

OTHER PUBLICATIONS

Youngblood et al. Bioconjugate Chem 2007, 18, 50-60.*
KR 10-2013-0005208 pp. 1-29, Machine English Translation.*
GenBank 01251363 [KR 1020130005208-A/39: Method and kit for detecting carbapenem resistant enterobacteriaceae using real-time PCR] (retrieved on Oct. 13, 2015 from http://www.ncbi.nlm.nih.gov/nucleotide/662699238?report=genbank&log$=nuclalign&blast_rank=1&RID=1V40 3DGD016] Jul. 8, 2014 (Jul. 8, 2014) whole doc.
PCT/US2015/031150, International Search Report and Written Opinion dated Jan. 14, 2016.
PCT/US2015/031213, International Search Report and Written Opinion dated Sep. 2, 2015.
PCT/US2015/000280, International Search Report and Written Opinion dated May 2, 2016.
Summerton et al. 1997, "Morpholino antisense oligomers: design, preparation, and properties." Antisense and Nucleic Acid Drug Development (1997); 7.3: 187-195.
PCT/US2015/031150, International Preliminary Report on Patentability dated Nov. 22, 2016, 11 pages.
PCT/US2015/031213, International Preliminary Report on Patentability dated Nov. 22, 2016, 7 pages.

*Primary Examiner* — Brian Whiteman
(74) *Attorney, Agent, or Firm* — Cooley LLP

(57) ABSTRACT

Provided are antisense morpholino oligomers targeted against bacterial virulence factors such as genes that contribute to antibiotic resistance or biofilm formation, or genes associated with fatty acid biosynthesis, and related compositions and methods of using the oligomers and compositions, for instance, in the treatment of an infected mammalian subject.

38 Claims, 22 Drawing Sheets

(56) References Cited

FOREIGN PATENT DOCUMENTS

| | | |
|---|---|---|
| WO | WO 2009/005793 A2 | 1/2009 |
| WO | WO 2009/064471 A1 | 5/2009 |
| WO | WO 2012/043730 | 4/2012 |
| WO | WO 2012/064991 A1 | 5/2012 |
| WO | WO 2012/150960 A1 | 11/2012 |
| WO | WO2013011072 A1 * | 1/2013 |
| WO | WO 2015/175977 A2 | 11/2015 |
| WO | WO 2015/179249 A1 | 11/2015 |
| WO | WO 2016/108930 A2 | 7/2016 |

* cited by examiner

```
                         SEQUENCE LISTING

<160> NUMBER OF SEQ ID NOS: 42

<210> SEQ ID NO 1
<211> LENGTH: 60
<212> TYPE: DNA
<213> ORGANISM: Escherichia coli

<400> SEQUENCE: 1
gtttttaatg ctgaataaaa ggaaaacttg atggaattgc ccaatattat gcacccggtc     60

<210> SEQ ID NO 2
<211> LENGTH: 60
<212> TYPE: DNA
<213> ORGANISM: Klebsiella pneumoniae

<400> SEQUENCE: 2
gtttttaatg ctgaataaaa ggaaaacttg atggaattgc ccaatattat gcacccggtc     60

<210> SEQ ID NO 3
<211> LENGTH: 60
<212> TYPE: DNA
<213> ORGANISM: Acinetobacter baumannii

<400> SEQUENCE: 3
aacatcaaaa agtcactagg tttggacagt atgcaaaagc atcttttact tcctttattt     60

<210> SEQ ID NO 4
<211> LENGTH: 60
<212> TYPE: DNA
<213> ORGANISM: Acinetobacter baumannii

<400> SEQUENCE: 4
aacatcaaaa agtcactagg tttggacagt atgcaaaagc atcttttact tcctttattt     60

<210> SEQ ID NO 5
<211> LENGTH: 60
<212> TYPE: DNA
<213> ORGANISM: Burkholderia cenocepacia

<400> SEQUENCE: 5
```
gcatacaaaa gcacagatcc gaggacatcc atgcagacct tcgttcacga ggaagggcgg    60

<210> SEQ ID NO 6
<211> LENGTH: 60
<212> TYPE: DNA
<213> ORGANISM: Acinetobacter baumannii

<400> SEQUENCE: 6
tcacttgaaa ataagtgga agcacttgta atgaatatta ttgctggatt tcaaaacaat    60

<210> SEQ ID NO 7
<211> LENGTH: 60
<212> TYPE: DNA
<213> ORGANISM: Acinetobacter baumannii

<400> SEQUENCE: 7
tcttcaaatt tgtattgtag tgggtgttca atggaaccta tggtggtgat ggctgcgcgt    60

<210> SEQ ID NO 8
<211> LENGTH: 60
<212> TYPE: DNA
<213> ORGANISM: Burkholderia cenocepacia

<400> SEQUENCE: 8
cccgtgccgc cggctacagg atccaggctc atgcatccca tgctcaacat tgctgtcaag    60

<210> SEQ ID NO 9
<211> LENGTH: 767
<212> TYPE: DNA
<213> ORGANISM: Burkholderia cenocepacia

<400> SEQUENCE: 9
cccgtgccgc cggctacagg atccaggctc atgcatccca tgctcaacat tgctgtcaag    60
gctgcgcgcc gcgccggaca gatcatcaat cgcgcgtccc tcgatctcga cctgatcgag   120
atccgcaaga agcagcagaa cgacttcgtc accgaagtgg acaaggccgc cgaagacgcg   180
atcatcgaga cgctgaagac cgcctacccc gaccacgcga tcctcgcgga ggaatcgggc   240
gaatccgaca acgaatccga attcaagtgg atcatcgatc cgctcgacgg cacgaccaac   300
ttcatccacg gcttcccgta ttactgcgta tcgatcgcgc tcgagcacaa gggcgtcgtc   360
acgcaggccg tcgtctacga tccgaacaag aacgacctgt tcacgccac ccgcggccgc   420
ggcgcatacc tgaacgaccg ccgcatccgc gtcggccgcc gcgaccgcct ggcagacgca   480
ctggtcggca cgggcttccc gttccgcgag aaggacggcc tcgacgccta cgcgcgcctc   540
ttcaccgaaa tgacgcaggc ctgcacgggc ctgcgccgtc cgggcgcggc ggcgctcgat   600
ctcgcgaacg tcgcggccgg ccgcctcgac gcgttcttcg agcaaggcat caacgtgtgg   660
gacatggcag cgggcagcct gctgatcacc gaggccggcg gcctcgtcgg gaactacacg   720
ggcgacgccg atttcctgca tcgccacgag atcgtcgccg cgaaccc                 767

<210> SEQ ID NO 10
<211> LENGTH: 81
<212> TYPE: DNA
<213> ORGANISM: artificial
<220> FEATURE:
<223> OTHER INFORMATION: acpP target sequence

<400> SEQUENCE: 10
gcgcacttgt aaatctgaac tttccctcgg aggggtaatg acaacatcg aacaacgtgt    60 caagaagatg tcgctgaaca a                                              81

<210> SEQ ID NO 11
<211> LENGTH: 11
<212> TYPE: DNA
<213> ORGANISM: artificial
<220> FEATURE:
<223> OTHER INFORMATION: NDM-1 targeting sequence

<400> SEQUENCE: 11
tcaagttttc c                                                         11

<210> SEQ ID NO 12
<211> LENGTH: 11
<212> TYPE: DNA
<213> ORGANISM: artificial
<220> FEATURE:
<223> OTHER INFORMATION: NDM-1 targeting sequence

<400> SEQUENCE: 12
tccttttatt c                                                         11

<210> SEQ ID NO 13
<211> LENGTH: 11
<212> TYPE: DNA
<213> ORGANISM: artificial
<220> FEATURE:
<223> OTHER INFORMATION: NDM-1 targeting sequence

<400> SEQUENCE: 13
ccatcaagtt t                                                         11

<210> SEQ ID NO 14
<211> LENGTH: 11
<212> TYPE: DNA
<213> ORGANISM: artificial
<220> FEATURE:
<223> OTHER INFORMATION: NDM-1 targeting sequence

<400> SEQUENCE: 14
ggcaattcca t                                                         11

<210> SEQ ID NO 15
<211> LENGTH: 11
<212> TYPE: DNA
<213> ORGANISM: artificial
<220> FEATURE:
<223> OTHER INFORMATION: adeA targeting sequence

<400> SEQUENCE: 15
atactgtcca a                                                         11

<210> SEQ ID NO 16
<211> LENGTH: 11
<212> TYPE: DNA
<213> ORGANISM: artificial
<220> FEATURE:
<223> OTHER INFORMATION: cepI targeting sequence

<400> SEQUENCE: 16
aaggtctgca t                                                         11

<210> SEQ ID NO 17
<211> LENGTH: 11
<212> TYPE: DNA
<213> ORGANISM: artificial

```
<220> FEATURE:
<223> OTHER INFORMATION: cepI targeting sequence

<400> SEQUENCE: 17
tcggatctgt g                                                          11

<210> SEQ ID NO 18
<211> LENGTH: 11
<212> TYPE: DNA
<213> ORGANISM: artificial
<220> FEATURE:
<223> OTHER INFORMATION: cepI targeting sequence

<400> SEQUENCE: 18
catggatgtc c                                                          11

<210> SEQ ID NO 19
<211> LENGTH: 11
<212> TYPE: DNA
<213> ORGANISM: artificial
<220> FEATURE:
<223> OTHER INFORMATION: cepI targeting sequence

<400> SEQUENCE: 19
cgtgaacgaa g                                                          11

<210> SEQ ID NO 20
<211> LENGTH: 11
<212> TYPE: DNA
<213> ORGANISM: artificial
<220> FEATURE:
<223> OTHER INFORMATION: cepI targeting sequence

<400> SEQUENCE: 20
cgtgtggcaa c                                                          11

<210> SEQ ID NO 21
<211> LENGTH: 11
<212> TYPE: DNA
<213> ORGANISM: artificial
<220> FEATURE:
<223> OTHER INFORMATION: cepI targeting sequence

<400> SEQUENCE: 21
gcccgagatc c                                                          11

<210> SEQ ID NO 22
<211> LENGTH: 11
<212> TYPE: DNA
<213> ORGANISM: artificial
<220> FEATURE:
<223> OTHER INFORMATION: cepI targeting sequence

<400> SEQUENCE: 22
ctttcgttcg c                                                          11

<210> SEQ ID NO 23
<211> LENGTH: 11
<212> TYPE: DNA
<213> ORGANISM: artificial
<220> FEATURE:
<223> OTHER INFORMATION: suhB targeting sequence

<400> SEQUENCE: 23
atgcatgagc c                                                          11
```

```
<210> SEQ ID NO 24
<211> LENGTH: 11
<212> TYPE: DNA
<213> ORGANISM: artificial
<220> FEATURE:
<223> OTHER INFORMATION: suhB targeting sequence

<400> SEQUENCE: 24
ggatgcatga g                                                      11

<210> SEQ ID NO 25
<211> LENGTH: 11
<212> TYPE: DNA
<213> ORGANISM: artificial
<220> FEATURE:
<223> OTHER INFORMATION: acpP targeting sequence

<400> SEQUENCE: 25
gtccattacc c                                                      11

<210> SEQ ID NO 26
<211> LENGTH: 11
<212> TYPE: DNA
<213> ORGANISM: artificial
<220> FEATURE:
<223> OTHER INFORMATION: acpP targeting sequence

<400> SEQUENCE: 26
cattacccct c                                                      11

<210> SEQ ID NO 27
<211> LENGTH: 11
<212> TYPE: DNA
<213> ORGANISM: artificial
<220> FEATURE:
<223> OTHER INFORMATION: acpP targeting sequence

<400> SEQUENCE: 27
ccattacccc t                                                      11

<210> SEQ ID NO 28
<211> LENGTH: 11
<212> TYPE: DNA
<213> ORGANISM: artificial
<220> FEATURE:
<223> OTHER INFORMATION: acpP targeting sequence

<400> SEQUENCE: 28
tccattaccc c                                                      11

<210> SEQ ID NO 29
<211> LENGTH: 11
<212> TYPE: DNA
<213> ORGANISM: artificial
<220> FEATURE:
<223> OTHER INFORMATION: acpP targeting sequence

<400> SEQUENCE: 29
tgtccattac c                                                      11

<210> SEQ ID NO 30
<211> LENGTH: 11
<212> TYPE: DNA
<213> ORGANISM: artificial
<220> FEATURE:
<223> OTHER INFORMATION: acpP targeting sequence
```

```
<400> SEQUENCE: 30
ttgtccatta c                                                       11

<210> SEQ ID NO 31
<211> LENGTH: 11
<212> TYPE: DNA
<213> ORGANISM: artificial
<220> FEATURE:
<223> OTHER INFORMATION: acpP targeting sequence

<400> SEQUENCE: 31
gttgtccatt a                                                       11

<210> SEQ ID NO 32
<211> LENGTH: 11
<212> TYPE: DNA
<213> ORGANISM: artificial
<220> FEATURE:
<223> OTHER INFORMATION: acpP targeting sequence

<400> SEQUENCE: 32
tgttgtccat t                                                       11

<210> SEQ ID NO 33
<211> LENGTH: 11
<212> TYPE: DNA
<213> ORGANISM: artificial
<220> FEATURE:
<223> OTHER INFORMATION: acpP targeting sequence

<400> SEQUENCE: 33
atgttgtcca t                                                       11

<210> SEQ ID NO 34
<211> LENGTH: 11
<212> TYPE: DNA
<213> ORGANISM: artificial
<220> FEATURE:
<223> OTHER INFORMATION: acpP targeting sequence

<400> SEQUENCE: 34
tttacaagtg c                                                       11

<210> SEQ ID NO 35
<211> LENGTH: 11
<212> TYPE: DNA
<213> ORGANISM: artificial
<220> FEATURE:
<223> OTHER INFORMATION: acpP targeting sequence

<400> SEQUENCE: 35
cctccgaggg a                                                       11

<210> SEQ ID NO 36
<211> LENGTH: 11
<212> TYPE: DNA
```

```
<213> ORGANISM: artificial
<220> FEATURE:
<223> OTHER INFORMATION: acpP targeting sequence

<400> SEQUENCE: 36
acacgttgtt c                                                           11

<210> SEQ ID NO 37
<211> LENGTH: 11
<212> TYPE: DNA
<213> ORGANISM: artificial
<220> FEATURE:
<223> OTHER INFORMATION: acpP targeting sequence

<400> SEQUENCE: 37
agttcagcga c                                                           11

<210> SEQ ID NO 38
<211> LENGTH: 12
<212> TYPE: PRT
<213> ORGANISM: artificial
<220> FEATURE:
<223> OTHER INFORMATION: CPP sequence
<220> FEATURE:
<221> NAME/KEY: MOD_RES
<222> LOCATION: (2)..(2)
<223> OTHER INFORMATION: Acp
<220> FEATURE:
<221> NAME/KEY: MOD_RES
<222> LOCATION: (5)..(5)
<223> OTHER INFORMATION: Acp
<220> FEATURE:
<221> NAME/KEY: MOD_RES
<222> LOCATION: (8)..(8)
<223> OTHER INFORMATION: Acp
<220> FEATURE:
<221> NAME/KEY: MOD_RES
<222> LOCATION: (11)..(11)
<223> OTHER INFORMATION: Acp

<400> SEQUENCE: 38

Arg Xaa Arg Arg Xaa Arg Arg Xaa Arg Arg Xaa Arg
1               5                   10

<210> SEQ ID NO 39
<211> LENGTH: 10
<212> TYPE: PRT
<213> ORGANISM: artificial
<220> FEATURE:
<223> OTHER INFORMATION: CPP sequence

<400> SEQUENCE: 39

Arg Phe Phe Arg Phe Phe Arg Phe Phe Arg
1               5                   10

<210> SEQ ID NO 40
<211> LENGTH: 14
<212> TYPE: PRT
<213> ORGANISM: artificial
<220> FEATURE:
<223> OTHER INFORMATION: CPP sequence
<220> FEATURE:
<221> NAME/KEY: MOD_RES
<222> LOCATION: (2)..(2)
<223> OTHER INFORMATION: Acp
<220> FEATURE:
```

```
<221> NAME/KEY: MOD_RES
<222> LOCATION: (5)..(5)
<223> OTHER INFORMATION: Acp
<220> FEATURE:
<221> NAME/KEY: MOD_RES
<222> LOCATION: (8)..(8)
<223> OTHER INFORMATION: Acp
<220> FEATURE:
<221> NAME/KEY: MOD_RES
<222> LOCATION: (11)..(11)
<223> OTHER INFORMATION: Acp
<220> FEATURE:
<221> NAME/KEY: MOD_RES
<222> LOCATION: (13)..(13)
<223> OTHER INFORMATION: Acp
<220> FEATURE:
<221> NAME/KEY: MOD_RES
<222> LOCATION: (14)..(14)
<223> OTHER INFORMATION: bAla

<400> SEQUENCE: 40

Arg Xaa Arg Arg Xaa Arg Arg Xaa Arg Arg Xaa Arg Xaa Xaa
1               5                   10

<210> SEQ ID NO 41
<211> LENGTH: 12
<212> TYPE: PRT
<213> ORGANISM: artificial
<220> FEATURE:
<223> OTHER INFORMATION: CPP sequence
<220> FEATURE:
<221> NAME/KEY: MOD_RES
<222> LOCATION: (11)..(11)
<223> OTHER INFORMATION: Acp
<220> FEATURE:
<221> NAME/KEY: MOD_RES
<222> LOCATION: (12)..(12)
<223> OTHER INFORMATION: bAla

<400> SEQUENCE: 41

Arg Phe Phe Arg Phe Phe Arg Phe Phe Arg Xaa Xaa
1               5                   10

<210> SEQ ID NO 42
<211> LENGTH: 11
<212> TYPE: PRT
<213> ORGANISM: artificial
<220> FEATURE:
<223> OTHER INFORMATION: CPP sequence

<400> SEQUENCE: 42

Arg Phe Phe Arg Phe Phe Arg Phe Phe Arg Gly
1               5                   10
```

ANTISENSE ANTIBACTERIAL COMPOUNDS AND METHODS

CROSS-REFERENCE TO RELATED APPLICATIONS

This application claims priority under 35 U.S.C. §119(e) to U.S. Application No. 61/994,750, filed May 16, 2014, U.S. Application No. 62/099,046, filed Dec. 31, 2014, and U.S. Application No. 62/129,746, filed Mar. 6, 2015; each of which is incorporated by reference in its entirety.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is SATH-003_03US_ST25.txt. The text file is about 10 KB, was created on May 15, 2015, and is being submitted electronically via EFS-Web.

BACKGROUND

Technical Field

The present disclosure relates to antisense morpholino oligomers targeted against bacterial virulence factors such as genes that contribute to antibiotic resistance, biofilm formation or fatty acid biosynthesis, and related compositions and methods of using the oligomers and compositions, for instance, in the treatment of an infected mammalian subject.

Description of the Related Art

Currently, there are several types of antibiotic compounds in use against bacterial pathogens and these compounds act through a variety of anti-bacterial mechanisms. For example, beta-lactam antibiotics, such as penicillin and cephalosporin, act to inhibit the final step in peptidoglycan synthesis. Glycopeptide antibiotics, including vancomycin and teichoplanin, inhibit both transglycosylation and transpeptidation of muramyl-pentapeptide, again interfering with peptidoglycan synthesis. Other well-known antibiotics include the quinolones, which inhibit bacterial DNA replication, inhibitors of bacterial RNA polymerase, such as rifampin, and inhibitors of enzymes in the pathway for production of tetrahydrofolate, including the sulfonamides.

Some classes of antibiotics act at the level of protein synthesis. Notable among these are the aminoglycosides, such as kanamycin and gentamicin. This class of compounds targets the bacterial 30S ribosome subunit, preventing the association with the 50S subunit to form functional ribosomes. Tetracyclines, another important class of antibiotics, also target the 30S ribosome subunit, acting by preventing alignment of aminoacylated tRNA's with the corresponding mRNA codon. Macrolides and lincosamides, another class of antibiotics, inhibit bacterial synthesis by binding to the 50S ribosome subunit, and inhibiting peptide elongation or preventing ribosome translocation.

Despite impressive successes in controlling or eliminating bacterial infections by antibiotics, the widespread use of antibiotics both in human medicine and as a feed supplement in poultry and livestock production has led to drug resistance in many pathogenic bacteria. Antibiotic resistance mechanisms can take a variety of forms. One of the major mechanisms of resistance to beta lactams, particularly in Gram-negative bacteria, is the enzyme beta-lactamase, which renders the antibiotic inactive by cleaving the lactam ring. Likewise, resistance to aminoglycosides often involves an enzyme capable of inactivating the antibiotic, in this case by adding a phosphoryl, adenyl, or acetyl group. Active efflux of antibiotics is another way that many bacteria develop resistance. Genes encoding efflux proteins, such as the tetA, tetG, tetL, and tetK genes for tetracycline efflux, have been identified. A bacterial target may develop resistance by altering the target of the drug. For example, the so-called penicillin binding proteins (PBPs) in many beta-lactam resistant bacteria are altered to inhibit the critical antibiotic binding to the target protein. Resistance to tetracycline may involve, in addition to enhanced efflux, the appearance of cytoplasmic proteins capable of competing with ribosomes for binding to the antibiotic. For those antibiotics that act by inhibiting a bacterial enzyme, such as for sulfonamides, point mutations in the target enzyme may confer resistance.

Biofilm formation can also lead to antibiotic resistance, among other clinical difficulties. Typically, in situations where bacteria form a biofilm within an infected host, the infection turns out to be untreatable and can develop into a chronic state. Hallmarks of chronic biofilm-based infections not only include resistance to antibiotic treatments and many other conventional antimicrobial agents but also a capacity for evading host defenses. Therefore, strategies that prevent or breakdown biofilm would be of therapeutic interest and benefit.

The appearance of antibiotic resistance in many pathogenic bacteria, including cases involving multi-drug resistance (MDR), raises the fear of a post-antibiotic era in which many bacterial pathogens were simply untreatable by medical intervention. Thus, there is a need for antimicrobial agents that (i) are not subject to the principal types of antibiotic resistance currently hampering antibiotic treatment of bacterial infection, (ii) can be developed rapidly and with some reasonable degree of predictability as to target-bacteria specificity, (iii) are effective at low doses, and (iv) show few side effects.

SUMMARY

Embodiments of the present disclosure relate, in part, to the discovery that the antisense targeting of bacterial virulence factors can, inter alia, increase the antibiotic susceptibility of otherwise antibiotic-resistant pathogenic bacteria, and reduce the ability of certain pathogenic bacteria to form and maintain difficult-to-treat biofilms. For example, the antisense targeting of antibiotic resistance genes such as carbapenemases and efflux pumps was shown to increase the susceptibility of antibiotic resistant (e.g., multi-drug resistant) bacteria to many commonly used antibiotics, and could thus find utility in the treatment of such bacteria, for instance, in combination with antibiotics. Also, the antisense targeting of genes associated with biofilm formation was shown to break down existing biofilms and reduce the production of new biofilms. Such antisense targeting could find utility in standalone therapies against biofilm-forming bacteria, and as combination therapies, for example, to increase the susceptibility of biofilm-forming bacteria to antibiotics.

Embodiments of the present disclosure therefore include a substantially uncharged antisense morpholino oligomer, composed of morpholino subunits and phosphorus-containing intersubunit linkages joining a morpholino nitrogen of one subunit to a 5'-exocyclic carbon of an adjacent subunit, and having (a) about 10-40 nucleotide bases, and (b) a targeting sequence of sufficient length and complementarity to specifically hybridize to a bacterial mRNA target sequence that encodes a virulence factor; where the oligomer is conjugated to a cell-penetrating peptide (CPP).

In certain embodiments, the target sequence comprises a translational start codon of the bacterial mRNA and/or a sequence within about 30 bases upstream or downstream of the translational start codon of the bacterial mRNA.

In some embodiments, the virulence factor is an antibiotic resistance protein, a biofilm formation protein or a protein associated with fatty acid biosynthesis.

In certain embodiments, the antibiotic resistance protein is selected from one or more of New Delhi metallo-beta-lactamase (NDM-1) and resistance-nodulation-cell division (RND)-type multidrug efflux pump subunit AdeA (adeA). In specific embodiments, the target sequence is selected from Table 1A. Some antisense oligomers comprise, consist, or consist essentially of a targeting sequence set forth in Table 2A, a fragment of at least 10 contiguous nucleotides of a targeting sequence in Table 2A, or variant having at least 80% sequence identity to a targeting sequence in Table 2A.

In some embodiments, the biofilm formation protein is encoded by one or more of cepI or suhB. In particular embodiments, the target sequence is selected from Table 1B. Some antisense oligomers comprise, consist, or consist essentially of a targeting sequence set forth in Table 2B, a fragment of at least 10 contiguous nucleotides of a targeting sequence in Table 2B, or variant having at least 80% sequence identity to a targeting sequence in Table 2B.

In some embodiments, the protein associated with fatty acid biosynthesis is an acyl carrier protein encoded by one or more of acpP. In particular embodiments, the target sequence is selected from Table 1C. Some antisense oligomers comprise, consist, or consist essentially of a targeting sequence set forth in Table 2C, a fragment of at least 10 contiguous nucleotides of a targeting sequence in Table 2C, or variant having at least 80% sequence identity to a targeting sequence in Table 2C.

In certain embodiments, an antisense morpholino oligomer of the disclosure may be of formula (I):

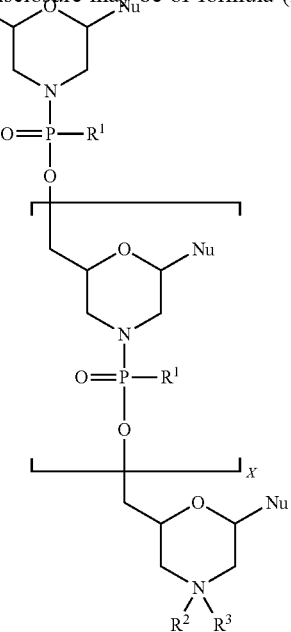

or a pharmaceutically acceptable salt thereof, where each Nu is a nucleobase which taken together forms a targeting sequence;

X is an integer from 9 to 38;

T is selected from OH and a moiety of the formula:

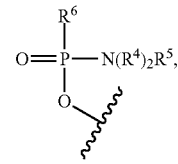

where each $R^4$ is independently $C_1$-$C_6$ alkyl, and $R^5$ is selected from an electron pair and H, and $R^6$ is selected from OH, —N($R^7$)$CH_2$C(O)$NH_2$, and a moiety of the formula:

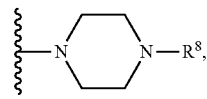

where:

$R^7$ is selected from H and $C_1$-$C_6$ alkyl, and $R^8$ is selected from G, —C(O)—$R^9$OH, acyl, trityl, and 4-methoxytrityl, where:

$R^9$ is of the formula —(O-alkyl)$_y$- wherein y is an integer from 3 to 10 and each of the y alkyl groups is independently selected from $C_2$-$C_6$ alkyl;

each instance of $R^1$ is —N($R^{10}$)$_2$$R^{11}$ wherein each $R^{10}$ is independently $C_1$-$C_6$ alkyl, and $R^{11}$ is selected from an electron pair and H;

$R^2$ is selected from H, G, acyl, trityl, 4-methoxytrityl, benzoyl, stearoyl, and a moiety of the formula:

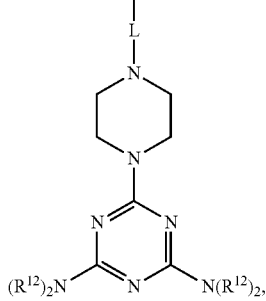

where L is selected from —C(O)(CH$_2$)$_6$C(O)— and —C(O)(CH$_2$)$_2$S$_2$(CH$_2$)$_2$C(O)—, and each $R^{12}$ is of the formula —(CH$_2$)$_2$OC(O)N($R^{14}$)$_2$ wherein each $R^{14}$ is of the formula —(CH$_2$)$_6$NHC(=NH)NH$_2$; and $R^3$ is selected from an electron pair, H, and $C_1$-$C_6$ alkyl, wherein G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

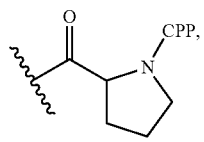

wherein the CPP is attached to the linker moiety by an amide bond at the CPP carboxy terminus, with the proviso that only one instance of G is present, wherein the targeting sequence specifically hybridizes to a bacterial mRNA target sequence that encodes a virulence factor.

In certain embodiments, the CPP is an arginine-rich peptide. In certain embodiments, the CPP is selected from Table 1C.

Also included are methods of reducing expression and activity of a virulence factor in a bacteria or bacterium, comprising contacting the bacteria or bacterium with an antisense oligomer described herein.

In some embodiments, the bacterium is in a subject, and the method comprises administering the antisense oligomer to the subject.

In certain embodiments, the bacterium is selected from the genus *Escherichia, Acinetobacter, Klebsiella,* and *Burkholderia*. In certain embodiments, the bacterium is *Escherichia coli, Acinetobacter baumannii, Klebsiella pneumoniae,* or *Burkholderia cepacia* (complex). In certain embodiments, the bacterium is *Escherichia coli, Acinetobacter baumannii,* or *Klebsiella pneumoniae,* and where the virulence factor is an antibiotic resistance protein selected from one or more of NDM-1 and AdeA.

In some embodiments, the bacterium is *Burkholderia cepacia* (complex) and where the virulence factor is a biofilm formation protein encoded by one or more of cepI and suhB. In certain embodiments, the *Burkholderia cepacia* (complex) comprises one or more of *Burkholderia cenocepacia, Burkholderia multivorans, Burkholderia vietnamiensis, Burkholderia stabilis, Burkholderia anthina, Burkholderia pyrrocinia, Burkholderia dolosa,* and/or *Burkholderia ambifaria*. In certain embodiments, administration of the antisense oligomer reduces biofilm formation or existing biofilm by at least about 10%. In certain embodiments, the subject is immunocompromised and has an underlying lung disease. In specific embodiments, the subject has cystic fibrosis (CF) or chronic granulomatous disease (CGD).

In some embodiments, the bacterium is *Burkholderia cepacia* (complex) and where the virulence factor is an acyl carrier protein associated with fatty acid biosynthesis encoded by one or more of acpP. In certain embodiments, the *Burkholderia cepacia* (complex) comprises one or more of *Burkholderia cenocepacia, Burkholderia multivorans, Burkholderia vietnamiensis, Burkholderia stabilis, Burkholderia anthina, Burkholderia pyrrocinia, Burkholderia dolosa,* and/or *Burkholderia ambifaria*. In certain embodiments, administration of the antisense oligomer reduces biofilm formation or existing biofilm by at least about 10%. In certain embodiments, the subject is immunocompromised and has an underlying lung disease. In specific embodiments, the subject has cystic fibrosis (CF) or chronic granulomatous disease (CGD).

Some methods include administering the oligomer separately or concurrently with an antimicrobial agent, for example, where administration of the oligomer increases susceptibility of the bacterium to the antimicrobial agent. Some methods include administering the oligomer by aerosolization.

In certain embodiments, the bacterium is *Escherichia coli, Acinetobacter baumannii,* or *Klebsiella pneumoniae,* the virulence factor is NDM-1, and the antimicrobial agent is a carbapenem. In certain embodiments, the carbapenem is selected from one or more of meropenem, imipenem, ertapenem, doripenem, panipenem, biapenem, razupenem, tebipenem, lenapenem, and tomopenem.

In some embodiments, the bacterium is *Escherichia coli, Acinetobacter baumannii,* or *Klebsiella pneumoniae,* the virulence factor is AdeA, and the antimicrobial agent is selected from one or more of aminoglycoside antibiotics, tetracycline antibiotics, and β-lactam antibiotics. In certain embodiments, the aminoglycoside is selected from one or more of tobramycin, gentamicin, kanamycin a, amikacin, dibekacin, sisomicin, netilmicin, neomycin B, neomycin C, neomycin E (paromomycin), and streptomycin. In certain embodiments, the tetracycline antibiotic is selected from one or more of tetracycline, chlortetracycline, oxytetracycline, demeclocycline, lymecycline, meclocycline, methacycline, minocycline, rolitetracycline, and doxycyline. In certain embodiments, the β-lactam antibiotic is selected from one or more of carbapenems, penicillin derivatives (penams), cephalosporins (cephems), and monobactams.

In certain embodiments, the bacterium is *Burkholderia cepacia* (complex), the virulence factor is a biofilm formation protein encoded by one or more of cepI or suhB, and the antimicrobial agent is selected from one or more of ceftazidime, doxycycline, piperacillin, meropenem, chloramphenicol, and co-trimoxazole (trimethoprim/sulfamethoxazole).

In certain embodiments, the bacterium is *Burkholderia cepacia* (complex), the virulence factor is an acyl carrier protein associated with fatty acid biosynthesis encoded by one or more of acpP, and the antimicrobial agent is selected from one or more of ceftazidime, minocycline, doxycycline, piperacillin, meropenem, chloramphenicol, and co-trimoxazole (trimethoprim/sulfamethoxazole).

In some embodiments, the oligomer reduces the minimum inhibitory concentration (MIC) of the antimicrobial agent against the bacterium by at least about 10% relative to the antimicrobial agent alone. In certain embodiments, the oligomer increases the susceptibility of the bacterium to the antimicrobial agent by at least about 10% relative to the antimicrobial agent alone.

Also included are pharmaceutical compositions, comprising an antisense oligomer described herein and a pharmaceutically-acceptable carrier. Certain pharmaceutical compositions can further comprise one or more antimicrobial agents.

BRIEF DESCRIPTION OF THE FIGURES

FIG. 8A shows an untreated biofilm at 48 hours, FIG. 8B shows the 48-hour biofilm treated with 10 µM of the scramble PPMO control, and FIG. 8C shows the 48-hour biofilm treated with 10 µM of a cepI-targeted PPMO).

DETAILED DESCRIPTION

Definitions

Figure 1:
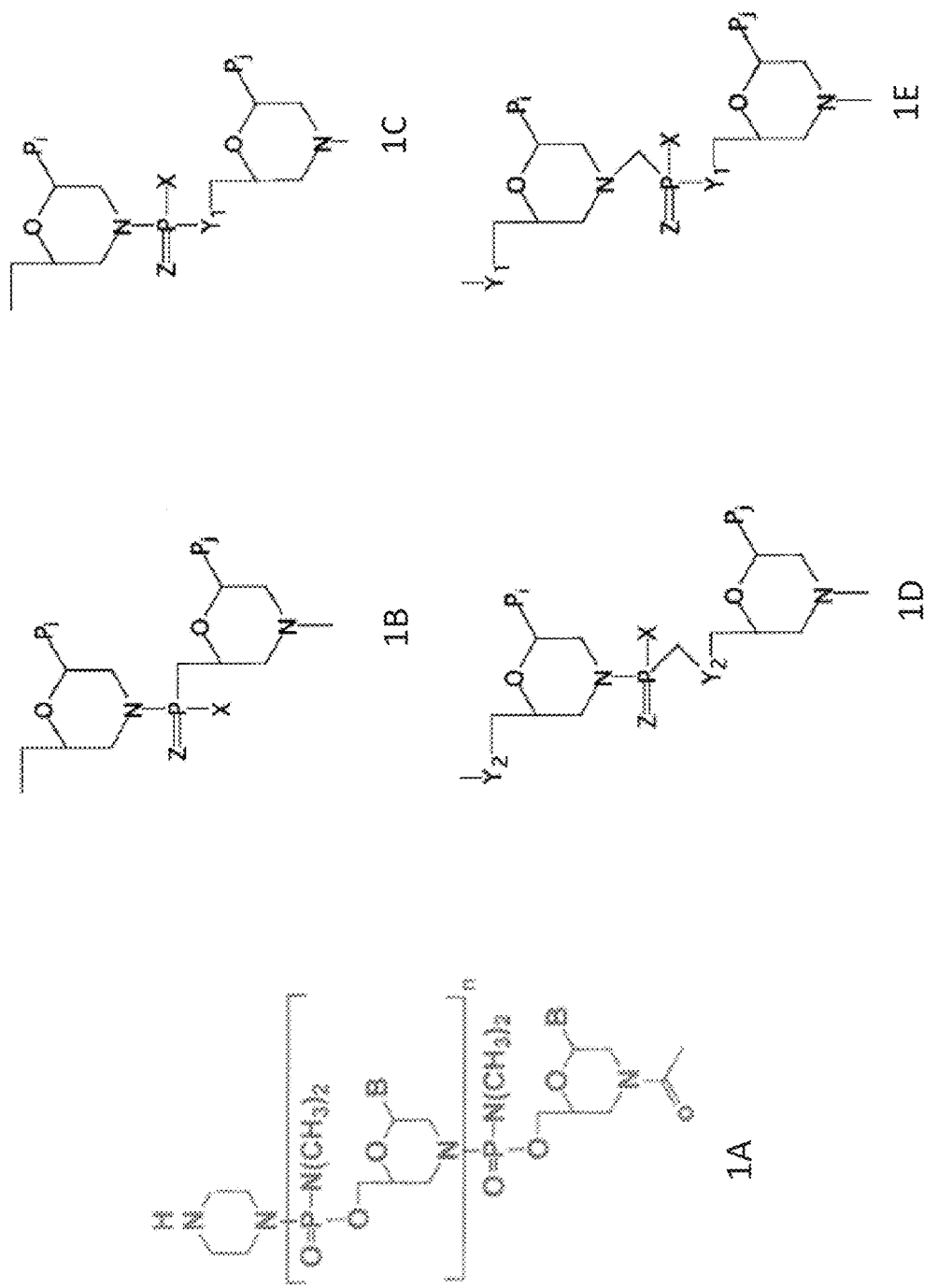
FIG. 1A shows an exemplary morpholino oligomer structure with a phosphorodiamidate linkage.
FIGS. 1B-E show the repeating subunit segment of exemplary morpholino oligomers, designated B through E.
FIGS. 1F-H show exemplary peptide PMO conjugates structures used in the exemplary PPMOs.
Figure 1:
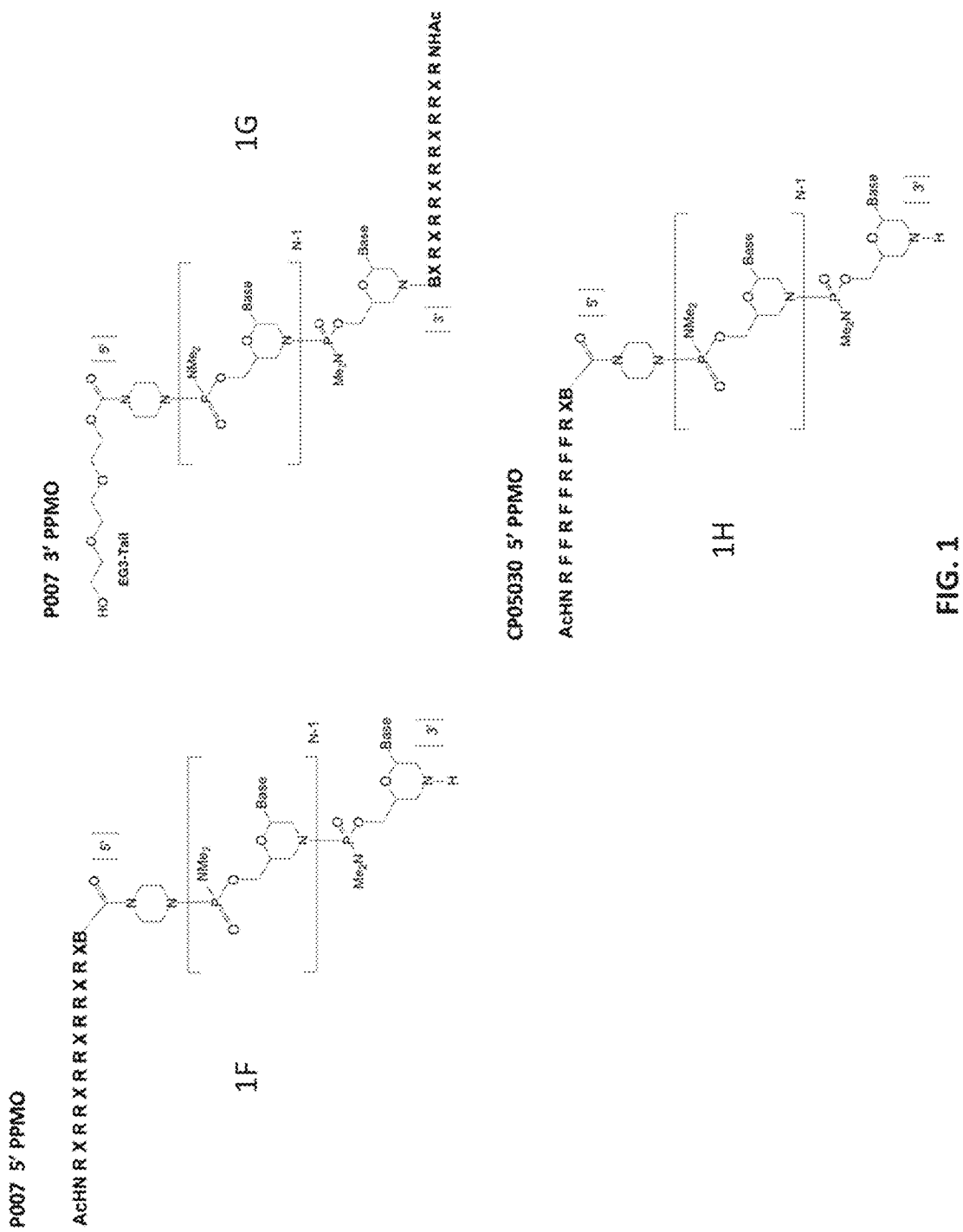

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight, or length that varies by as much as 30, 25, 20, 15, 10, 9, 8, 7, 6, 5, 4, 3, 2 or 1% to a reference quantity, level, value, number, frequency, percentage, dimension, size, amount, weight, or length.

By "coding sequence" is meant any nucleic acid sequence that contributes to the code for the polypeptide product of a gene. By contrast, the term "non-coding sequence" refers to any nucleic acid sequence that does not directly contribute to the code for the polypeptide product of a gene.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of:" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

As used herein, the terms "contacting a cell", "introducing" or "delivering" include delivery of the oligomers of this disclosure into a cell by methods routine in the art, e.g., transfection (e.g., liposome, calcium-phosphate, polyethyleneimine), electroporation (e.g., nucleofection), microinjection), transformation, and administration.

The terms "cell penetrating peptide" (CPP) or "a peptide moiety which enhances cellular uptake" are used interchangeably and refer to cationic cell penetrating peptides, also called "transport peptides", "carrier peptides", or "peptide transduction domains". In some aspects, the peptides have the capability of inducing cell penetration within about or at least about 30%, 40%, 50%, 60%, 70%, 80%, 90%, or 100% of cells of a given population and/or allow macromolecular translocation to or within multiple tissues in vivo upon systemic administration. Particular examples of CPPs include "arginine-rich peptides." CPPs are well-known in the art and are disclosed, for example, in U.S. Application No. 2010/0016215, which is incorporated by reference in its entirety.

"An electron pair" refers to a valence pair of electrons that are not bonded or shared with other atoms.

"Homology" refers to the percentage number of amino acids that are identical or constitute conservative substitutions. Homology may be determined using sequence comparison programs such as GAP (Deveraux et al., 1984, Nucleic Acids Research 12, 387-395) or BLAST. In this way sequences of a similar or substantially different length to those cited herein could be compared by insertion of gaps into the alignment, such gaps being determined, for example, by the comparison algorithm used by GAP.

By "isolated" is meant material that is substantially or essentially free from components that normally accompany it in its native state. For example, an "isolated polynucleotide" or "isolated oligomer," as used herein, may refer to a polynucleotide that has been purified or removed from the sequences that flank it in a naturally-occurring state, e.g., a DNA fragment that is removed from the sequences that are adjacent to the fragment in the genome. The term "isolating" as it relates to cells refers to the purification of cells (e.g., fibroblasts, lymphoblasts) from a source subject (e.g., a subject with a polynucleotide repeat disease). In the context of mRNA or protein, "isolating" refers to the recovery of mRNA or protein from a source, e.g., cells.

The term "modulate" includes to "increase" or "decrease" one or more quantifiable parameters, optionally by a defined and/or statistically significant amount. By "increase" or "increasing," "enhance" or "enhancing," or "stimulate" or "stimulating," refers generally to the ability of one or antisense compounds or compositions to produce or cause a greater physiological response (i.e., downstream effects) in a cell or a subject relative to the response caused by either no antisense compound or a control compound. Relevant physiological or cellular responses (in vivo or in vitro) will be apparent to persons skilled in the art. An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times) (including all integers and ranges between and above 1), e.g., 1.5, 1.6, 1.7, 1.8) the amount produced by no antisense compound (the absence of an agent) or a control compound. The term "reduce" or "inhibit" may relate generally to the ability of one or more antisense compounds or compositions to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include reductions in bacterial cell growth, reductions in the minimum inhibitory concentration (MIC) of an antimicrobial agent, and others. A "decrease" in a response may be "statistically significant" as compared to the response produced by no antisense compound or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers and ranges in between.

As used herein, an "antisense oligomer," "oligomer" or "oligomer" refers to a linear sequence of nucleotides, or nucleotide analogs, which allows the nucleobase (for example a purine or pyrimidine base-pairing moiety) to hybridize to a target sequence in an RNA by Watson-Crick base pairing, to form an oligomer:RNA heteroduplex within the target sequence. The terms "antisense oligomer", "antisense oligomer", "oligomer" and "compound" may be used interchangeably to refer to an oligomer. The cyclic subunits may be based on ribose or another pentose sugar or, in certain embodiments, a morpholino group (see description of morpholino oligomers below).

The term "oligomer," "oligomer," or "antisense oligomer" also encompasses an oligomer having one or more additional moieties conjugated to the oligomer, e.g., at its 3'- or 5'-end, such as a polyethylene glycol moiety or other hydrophilic polymer, e.g., one having 10-100 monomeric subunits, which may be useful in enhancing solubility, or a moiety such as a lipid or peptide moiety that is effective to enhance the uptake of the compound into target bacterial cells and/or enhance the activity of the compound within the cell, e.g., enhance its binding to a target polynucleotide.

A "nuclease-resistant" oligomers refers to one whose backbone is substantially resistant to nuclease cleavage, in non-hybridized or hybridized form; by common extracellular and intracellular nucleases in the body or in a bacterial cell (for example, by exonucleases such as 3'-exonucleases, endonucleases, RNase H); that is, the oligomer shows little or no nuclease cleavage under normal nuclease conditions to which the oligomer is exposed. A "nuclease-resistant heteroduplex" refers to a heteroduplex formed by the binding of an antisense oligomer to its complementary target, such that the heteroduplex is substantially resistant to in vivo degradation by intracellular and extracellular nucleases, which are capable of cutting double-stranded RNA/RNA or RNA/DNA complexes. A "heteroduplex" refers to a duplex between an antisense oligomer and the complementary portion of a target RNA.

As used herein, "nucleobase" (Nu), "base pairing moiety" or "base" are used interchangeably to refer to a purine or pyrimidine base found in native DNA or RNA (uracil, thymine, adenine, cytosine, and guanine), as well as analogs of the naturally occurring purines and pyrimidines, that confer improved properties, such as binding affinity to the oligomer. Exemplary analogs include hypoxanthine (the base component of the nucleoside inosine); 2,6-diaminopurine; 5-methyl cytosine; C5-propynyl-modified pyrimidines; 9-(aminoethoxy)phenoxazine (G-clamp) and the like.

A nucleobase covalently linked to a ribose, sugar analog or morpholino comprises a nucleoside. "Nucleotides" are composed of a nucleoside together with one phosphate group. The phosphate groups covalently link adjacent nucleotides to one another to form an oligomer.

An oligomer "specifically hybridizes" to a target sequence if the oligomer hybridizes to the target under physiological conditions, with a Tm substantially greater than 40° C. or 45° C., preferably at least 50° C., and typically 60° C.-80° C. or higher. Such hybridization preferably corresponds to stringent hybridization conditions. At a given ionic strength and pH, the Tm is the temperature at which 50% of a target sequence hybridizes to a complementary polynucleotide.

Such hybridization may occur with "near" or "substantial" complementarity of the antisense oligomer to the target sequence, as well as with exact complementarity.

As used herein, "sufficient length" includes an antisense oligomer that is complementary to at least about 8, more typically about 8-10, 8-11, 8-12, 8-13, 8-14, 8-15, 8-16, 8-17, 8-18, 8-19, 8-20, 8-30, 8-40, or 10-11, 10-12, 10-13, 10-14, 10-15, 10-16, 10-17, 10-18, 10-19, 10-20, 10-30, 10-40 (including all integers and ranges in between) contiguous or non-contiguous nucleobases in a region of a bacterial mRNA target sequence. An antisense oligomer of sufficient length has at least a minimal number of nucleotides to be capable of specifically hybridizing to a region of the bacterial mRNA target. In some embodiments, an oligomer of sufficient length is from 10 to 40 or 10 to 30 nucleotides in length, for example, about 10-11, 10-12, 10-13, 10-14, 10-15, 10-16, 10-17, 10-18, 10-19, 10-20, 10-25, 10-28, 10-30, 10-40, 11-12, 11-13, 11-14, 11-15, 11-16, 11-17, 11-18, 11-19, 11-20, 11-25, 11-28, 11-30, or 11-40 nucleotides in length, or about 10, 11, 12, 13, 14, 15, 16, 17, 18, 19, 20, 21, 22, 23, 24, 25, 26 27, 28, 29, 30, 31, 32, 33, 34, 35, 36, 37, 38, 39, or 40 nucleotides in length.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997.

A "subject" or a "subject in need thereof" includes a mammalian subject such as a human subject.

The terms "TEG," "EG3," or "triethylene glycol tail" refer to triethylene glycol moieties conjugated to the oligomer, e.g., at its 3'- or 5'-end. For example, in some embodiments, "TEG" includes, for example, wherein T of the compound of formula (I), (II), or (III) is of the formula:

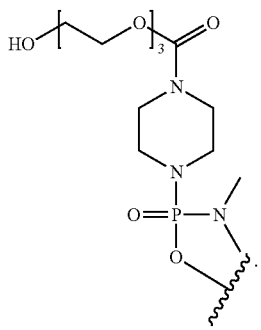

The term "pip-PDA" refers to a 5' terminal piperazine-phosphorodiamidate moiety that connects a G group, where the G group comprises a cell-penetrating peptide (CPP) and linker moiety further discussed below, to the 5' end of the oligomer by way of an amide bond between the G group linker and the piperazinyl nitrogen. For example, in some embodiments, "pip-PDA" includes wherein T of the compound of formula (I) or (II) is of the formula:

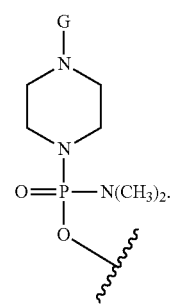

The term "target sequence" refers to a portion of the target RNA, for example, a bacterial mRNA, against which the antisense oligomer is directed, that is, the sequence to which the oligomer will hybridize by Watson-Crick base pairing of a complementary sequence. In certain embodiments, the target sequence may be a contiguous region of the translation initiation region of a bacterial gene.

The "translational start codon region" refers to a region that is 30 bases upstream or downstream of a translation initiation codon of a gene.

The term "targeting sequence" or "antisense targeting sequence" refers to the sequence in an oligomer that is complementary or substantially complementary to the target sequence in the RNA, e.g., the bacterial mRNA. The entire sequence, or only a portion, of the antisense compound may be complementary to the target sequence. For example, in an oligomer of about 10-30 bases, about 6, 7, 8, 9, 10, 11, 12, 13, 14, 15, 16, 17, 18, 19, 20, 21, 22, 23, 24, 25, 26, 27, 28, or 29 of the bases may be targeting sequences that are complementary to the target region. Typically, the targeting sequence is formed of contiguous bases, but may alternatively be formed of non-contiguous sequences that when placed together, e.g., from opposite ends of the oligomer, constitute sequence that spans the target sequence.

A "targeting sequence" may have "near" or "substantial" complementarity to the target sequence and still function for the purpose of the present disclosure, that is, still be "complementary." Preferably, the oligomer analog compounds employed in the present disclosure have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein.

As used herein, the term "quantifying", "quantification" or other related words refer to determining the quantity, mass, or concentration in a unit volume, of a nucleic acid, polynucleotide, oligomer, peptide, polypeptide, or protein.

As used herein, "treatment" of a subject (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

Sequences for Targeting Bacterial Virulence Factors

Certain embodiments relate to antisense oligomers, and related compositions and methods, which are of sufficient length and complementarity to specifically hybridize to a bacterial mRNA target sequence that encodes a virulence factor. General examples of virulence factors include antibiotic resistance genes, biofilm formation genes, genes associated with fatty acid biosynthesis and their encoded proteins. In addition, virulence factors include genes that encode regulatory proteins that control the expression (transcription and/or translation) of other genes which provide a benefit to the bacterium during the process of infection.

In certain embodiments, the target sequence contains all or a portion (e.g., 1 or 2 nucleotides) of a translational start codon of the bacterial mRNA. In some embodiments, the target sequence contains a sequence that is about or within about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 bases upstream or downstream of a translational start codon (e.g., ATG; AUG) of the bacterial mRNA target sequence. For example, in particular embodiments, the 5'-end of the target sequence is the adenine, uracil, or guanine nucleotide in a translational start codon of the bacterial mRNA. In some embodiments, the 5'-end or 3'-end of the target sequence begins at residue 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 downstream of the last nucleotide (e.g., guanine) of a translational start codon of the bacterial mRNA. In some embodiments, the 5'-end or 3'-end of the target sequence begins at residue 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 upstream of the first nucleotide (e.g., adenine) of a translational start codon of the bacterial mRNA In some embodiments, the virulence factor is an antibiotic resistance gene or its encoded protein, i.e., a gene or protein that is associated with resistance of the bacteria to at least one antimicrobial agent. General examples of antibiotic resistance genes include beta-lactamases, which can enzymatically deactivate certain antimicrobial agents, and proteins that increase the permeability or active efflux (pumping-out) of an antimicrobial agent. Particular examples of antibiotic resistance genes include New Delhi metallo-beta-lactamase (NDM-1) and resistance-nodulation-cell division (RND)-type multidrug efflux pump subunit AdeA (adeA). Exemplary translational start codon region sequences of the NDM-1 and AdeA resistance genes are provided in Table 1A below.

In some embodiments, the virulence factor is a biofilm formation gene or its encoded protein, i.e., a gene or protein that is associated with or contributes to the formation of biofilm. A biofilm can include any group of bacterial cells that adhere to each other on a surface, for example, a tissue surface or a surface of an implanted medical device. Such adherent cells are often embedded within a self-produced matrix of extracellular polymeric substance (EPS), a polymeric mixture composed, for example, of extracellular DNA, proteins, and polysaccharides. Bacteria form a biofilm in response to many factors, which may include cellular recognition of specific or non-specific attachment sites on a surface, nutritional cues, or in some cases, by exposure of cells to sub-inhibitory concentrations of antibiotics. The microbial cells growing in a biofilm are physiologically distinct from individual cells of the same organism. For example, when a bacterial cell switches to the biofilm mode of growth, it undergoes a phenotypic shift in behavior in which certain genes (e.g., biofilm formation-associated) are differentially regulated. Particular examples of biofilm formation genes include cepI, cepR, and suhB. In particular embodiments, the cepI gene is from a *Burkholderia* species or sub-species (e.g., *Burkholderia cepacia* complex, *Burkholderia cenocepacia*) and encodes an acylhomoserine lactone synthase. In some embodiments, the suhB gene is from a *Burkholderia* species or sub-species (e.g., *Burkholderia cepacia* complex, *Burkholderia cenocepacia*) and encodes a putative inositol-1-monophosphatase. In certain embodiments, the cepR gene is from a *Burkholderia* species or sub-species (e.g., *Burkholderia cepacia* complex, *Burkholderia cenocepacia*) and encodes an acylhomoserine lactone dependent regulatory protein. Exemplary translational start codon region sequences of biofilm formation genes from *Burkholderia* are provided in Table 1B below.

In some embodiments, the virulence factor is a gene or protein that is associated with biosynthesis of fatty acids. General examples of proteins associated with fatty acid biosynthesis include: acyl carrier protein (ACP), such as AcpP, that plays an essential role in stabilizing and shuttling the intermediate fatty acid chain to each of the enzymes in the fatty acid synthase complex; acyl carrier protein synthase (AcpS), an enzyme that transfers the 4'-phosphopantetheine prosthetic group to apo-ACP to form the functional holo-ACP; acetyl-CoA carboxylase, an enzyme composed of four proteins that catalyzes the conversion of acetyl-CoA to malonyl-CoA in the first committed step of fatty acid biosynthesis; fatty acid biosynthesis (Fab) enzymes, such as FabA, FabI, FabF, FabB, FabD, FabH, FabG and FabZ, that each catalyze either elongation or tailoring steps on the growing fatty acid chain. A particular example of a gene associated with fatty acid biosynthesis includes the acyl carrier protein acpP gene. An exemplary translational start codon region sequence of the acyl carrier protein acpP gene is provided in Table 1C below.

TABLE 1A

Exemplary Antibiotic Resistance Target Sequences

| Description | Sequence* | SEQ ID NO: |
|---|---|---|
| *E. coli* New Delhi Metallo-beta-lactamase-1 (NDM-1) | GTTTTTAATG CTGAATAAAA GGAAAACTTG ATGGAATTGC CCAATATTAT GCACCCGGTC | 1 |
| *Klebsiella pneumoniae* clone KPM_nasey | GTTTTTAATG CTGAATAAAA GGAAAACTTG ATGGAATTGC CCAATATTAT GCACCCGGTC | 2 |

TABLE 1A-continued

Exemplary Antibiotic Resistance Target Sequences

| Description | Sequence* | SEQ ID NO: |
|---|---|---|
| New Delhi metallo-beta-lactamase 1 (blaNDM-1) gene | | |
| Acinetobacter baumannii metallo-beta-lactamase | AACATCAAAA AGTCACTAGG TTTGGACAGT ATGCAAAAGC ATCTTTTACT TCCTTTATTT | 3 |
| Acinetobacter baumannii 1605 RND-type multidrug efflux pump subunit AdeA | AACATCAAAA AGTCACTAGG TTTGGACAGT ATGCAAAAGC ATCTTTTACT TCCTTTATTT | 4 |

TABLE 1B

Exemplary Biofilm Formation Target Sequences

| Description | Sequence* | SEQ ID NO: |
|---|---|---|
| cepI Burkholderia cenocepacia J2315 N-acylhomoserine lactone synthase | GCATACAAAA GCACAGATCC GAGGACATCC ATGCAGACCT TCGTTCACGA GGAAGGGCGG | 5 |
| cepI Actinetobacter baumannii AB307-0294 | TCACTTGAAA AATAAGTGGA AGCACTTGTA ATGAATATTA TTGCTGGATT TCAAAACAAT | 6 |
| suhB Actinetobacter baumannii AYE | TCTTCAAATT TGTATTGTAG TGGGTGTTCA ATGGAACCTA TGGTGGTGAT GGCTGCGCGT | 7 |
| SuhB Burkholderia cenocepacia J2315 Inositol-1-monophosphate | CCCGTGCCGC CGGCTACAGG ATCCAGGCTC ATGCATCCCA TGCTCAACAT TGCTGTCAAG | 8 |
| suhB Gene ID: 6932290 Locus Tag BCAL2157 | CCCGTGCCGCCGGCTACAGGATCCAGGCTCATGCATCCCATGCTCAACATTG CTGTCAAGGCTGCGCGCCGCGCCGGACAGATCATCAATCGCGCGTCCCTCGA TCTCGACCTGATCGAGATCCGCAAGAAGCAGCAGAACGACTTCGTCACCGAA GTGGACAAGGCCGCCGAAGACGCGATCATCGAGACGCTGAAGACCGCCTACC CCGACCACGCGATCCTCGCGGAGGAATCGGGCGAATCCGACAACGAATCCGA ATTCAAGTGGATCATCGATCCGCTCGACGGCACGACCAACTTCATCCACGGC TTCCCGTATTACTGCGTATCGATCGCGCTCGAGCACAAGGGCGTCGTCACGC AGGCCGTCGTCTACGATCCGAACAAGAACGACCTGTTCACGGCCACCCGCGG CCGCGGCGCATACCTGAACGACCGCCGCATCCGCGTCGGCCGCCGCGACCGC CTGGCAGACGCACTGGTCGGCACGGGCTTCCCGTTCCGCGAGAAGGACGGCC TCGACGCCTACGCGCCTCTTCACCGAAATGACGCAGGCCTGCACGGGCCT GCGCCGTCCGGGCGCGGCGGCGCTCGATCTCGCGAACGTCGCGGCCGGCCGC CTCGACGCGTTCTTCGAGCAAGGCATCAACGTGTGGGACATGGCAGCGGGCA GCCTGCTGATCACCGAGGCCGGCGGCCTCGTCGGGAACTACACGGGCGACGC CGATTTCCTGCATCGCCACGAGATCGTCGCCGCGAACCC | 9 |

TABLE 1C

Exemplary Fatty Acid Biosynthesis-Associated Target Sequence

| Description | Sequence* | SEQ ID NO: |
|---|---|---|
| acpP acyl carrier protein | GCGCACTTGTAAATCTGAACTTTCCCTCGGA GGGGTAATGACAACATCGAACAACGTGTCAA GCCGATGTCGCTGAACAA | 10 |

*The thymines (T) can be uracils (U)

Thus, in certain embodiments, antisense targeting sequences are designed to hybridize to a region of one or more of the target sequences listed in Table 1 or a target gene described herein. Selected antisense targeting sequences can be made shorter, e.g., about 8, 9, 10, 11, 12, 13, 14, or 15 bases, or longer, e.g., about 20, 30, or 40 bases, and include a small number of mismatches, as long as the sequence is sufficiently complementary to reduce transcription or translation upon hybridization to the target sequence, and optionally forms with the RNA a heteroduplex having a Tm of 45° C. or greater.

In certain embodiments, the degree of complementarity between the target sequence and antisense targeting sequence is sufficient to form a stable duplex. The region of complementarity of the antisense oligomers with the target RNA sequence may be as short as 8-9 bases, 8-10 bases, 8-11 bases, 8-12 bases, 10-11 bases, 10-12 bases, but can be 12-15 bases or more, e.g., 10-40 bases, 12-30 bases, 12-25 bases, 15-25 bases, 12-20 bases, or 15-20 bases, including all integers in between these ranges. An antisense oligomer of about 10-15 bases is generally long enough to have a unique complementary sequence. In certain embodiments, a minimum length of complementary bases may be required to achieve the requisite binding Tm, as discussed herein.

In certain embodiments, oligomers as long as 40 bases may be suitable, where at least a minimum number of bases, e.g., 10-12 bases, are complementary to the target sequence. In general, however, facilitated or active uptake in cells is optimized at oligomer lengths of less than about 30 or less than about 20 bases. Included are antisense oligomers that consist of about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases, in which at least about 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 contiguous or non-contiguous bases are complementary to a target gene described herein, for example, a target sequence of Table 1 (e.g., SEQ ID NOS: 1-10).

In certain embodiments, antisense oligomers may be 100% complementary to the target sequence, or may include mismatches, e.g., to accommodate variants, as long as a heteroduplex formed between the oligomer and target sequence is sufficiently stable to withstand the action of cellular nucleases and other modes of degradation which may occur in vivo, and reduce expression of the targeted mRNA. Hence, certain oligomers may have about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligomer and the target sequence. Oligomer backbones that are less susceptible to cleavage by nucleases are discussed herein. Mismatches, if present, are typically less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the target sequence, it is effective to stably and specifically bind to the target sequence, for example, such that translation of the target RNA is reduced.

The stability of the duplex formed between an oligomer and a target sequence is a function of the binding Tm and the susceptibility of the duplex to cellular enzymatic cleavage. The Tm of an oligomer with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligomer Hybridization Techniques, Methods Enzymol. Vol. 154 pp. 94-107. In certain embodiments, antisense oligomers may have a binding Tm, with respect to a complementary-sequence RNA, of greater than body temperature and preferably greater than about 45° C. or 50° C. Tm's in the range 60-80° C. or greater are also included. According to well-known principles, the Tm of an oligomer, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer.

Tables 2A-C below shows exemplary targeting sequences (in a 5'-to-3' orientation) of antisense oligomers described herein.

TABLE 2A

Exemplary Antibiotic Resistance Targeting Sequences

| Target Gene | Targeting Sequence (TS)* | TS SEQ ID NO: |
|---|---|---|
| NDM-1 | TCA AGT TTT CC | 11 |
| NDM-1 | TCC TTT TAT TC | 12 |
| NDM-1 | CCA TCA AGT TT | 13 |
| NDM-1 | GGC AAT TCC AT | 14 |
| adeA | ATA CTG TCC AA | 15 |

TABLE 2B

Exemplary Biofilm Formation Targeting Sequences

| Target Gene | Targeting Sequence (TS)* | TS SEQ ID NO: |
|---|---|---|
| cepI | AAG GTC TGC AT | 16 |
| cepI | TCG GAT CTG TG | 17 |
| cepI | CAT GGA TGT CC | 18 |
| cepI | CGT GAA CGA AG | 19 |
| cepI | CGT GTG GCA AC | 20 |
| cepI | GCC CGA GAT CC | 21 |

TABLE 2B-continued

Exemplary Biofilm Formation Targeting Sequences

| Target Gene | Targeting Sequence (TS)* | TS SEQ ID NO: |
|---|---|---|
| cepI | CTT TCG TTC GC | 22 |
| suhB | ATG CAT GAG CC | 23 |
| suhB | GGA TGC ATG AG | 24 |

TABLE 2C

Exemplary Fatty Acid Biosynthesis-Associated Targeting Sequences

| Target Gene | Targeting Sequence (TS)* | TS SEQ ID NO: |
|---|---|---|
| acpP | GTCCATTACCC | 25 |
| acpP | CATTACCCCTC | 26 |
| acpP | CCATTACCCCT | 27 |
| acpP | TCCATTACCCC | 28 |
| acpP | TGTCCATTACC | 29 |
| acpP | TTGTCCATTAC | 30 |
| acpP | GTTGTCCATTA | 31 |
| acpP | TGTTGTCCATT | 32 |
| acpP | ATGTTGTCCAT | 33 |
| acpP | TTTACAAGTGC | 34 |
| acpP | CCTCCGAGGGA | 35 |
| acpP | ACACGTTGTTC | 36 |
| acpP | AGTTCAGCGAC | 37 |

*The thymines (T) can be uracils (U).

Certain antisense oligomers thus comprise, consist, or consist essentially of a targeting sequence in Table 2 (e.g., SEQ ID NOS: 11-37) or a variant or contiguous or non-contiguous portion(s) thereof. For instance, certain antisense oligomers comprise about or at least about 6, 7, 8, 9, 10, 11, 12, 13, 14, 15, 16, 17, 18, 19, 20, 21, 22, 23, 24, 25, 26, or 27 contiguous or non-contiguous nucleotides of any of the targeting sequences in Table 2 (e.g., SEQ ID NOS: 11-37). For non-contiguous portions, intervening nucleotides can be deleted or substituted with a different nucleotide, or intervening nucleotides can be added. Additional examples of variants include oligomers having about or at least about 70% sequence identity or homology, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity or homology, over the entire length of any of the targeting sequences in Table 2 (e.g., SEQ ID NOS: 11-37).

The activity of antisense oligomers and variants thereof can be assayed according to routine techniques in the art (see, e.g., the Examples).

I. Antisense Oligomer Compounds

The antisense oligomers typically comprises a base sequence of sufficient length and complementarity to specifically hybridize to a bacterial mRNA target sequence that encodes a virulence factor, and thereby reduce expression (e.g., translation) of the virulence factor protein. This requirement is optionally met when the oligomer compound has the ability to be actively taken up by bacterial cells, and once taken up, form a stable duplex (or heteroduplex) with the target mRNA, optionally with a Tm greater than about 40° C. or 45° C.

A. Antisense Oligomer Chemical Features

In certain embodiments, the backbone of the antisense oligomer is substantially uncharged, and is optionally recognized as a substrate for active or facilitated transport across a cell wall and/or cell membrane. The ability of the oligomer to form a stable duplex with the target RNA may also relate to other features of the backbone, including the length and degree of complementarity of the antisense oligomer with respect to the target, the ratio of G:C to A:T base matches, and the positions of any mismatched bases. The ability of the antisense oligomer to resist cellular nucleases may promote survival and ultimate delivery of the agent to the cell. Exemplary antisense oligomer targeting sequences are listed in Table 2 (supra).

In certain embodiments, the antisense oligomer is a morpholino-based oligomer, for example, a phosphorodiamidate morpholino oligomer (PMO). Morpholino-based oligomers refer to an oligomer comprising morpholino subunits supporting a nucleobase and, instead of a ribose, contains a morpholine ring. Exemplary internucleoside linkages include, for example, phosphoramidate or phosphorodiamidate internucleoside linkages joining the morpholine ring nitrogen of one morpholino subunit to the 4' exocyclic carbon of an adjacent morpholino subunit. Each morpholino subunit comprises a purine or pyrimidine nucleobase effective to bind, by base-specific hydrogen bonding, to a base in an oligonucleotide.

Morpholino-based oligomers (including antisense oligomers) are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; and PCT Publication No. WO/2009/064471 and WO/2012/043730 and Summerton et al. 1997, Antisense and Nucleic Acid Drug Development, 7, 187-195, which are hereby incorporated by reference in their entirety.

Within the oligomer structure, the phosphate groups are commonly referred to as forming the "internucleoside linkages" of the oligomer. The naturally occurring internucleoside linkage of RNA and DNA is a 3' to 5' phosphodiester linkage. A "phosphoramidate" group comprises phosphorus having three attached oxygen atoms and one attached nitrogen atom, while a "phosphorodiamidate" group comprises phosphorus having two attached oxygen atoms and two attached nitrogen atoms. In the uncharged or the cationic internucleoside linkages of the morpholino-based oligomers described herein, one nitrogen is always pendant to the linkage chain. The second nitrogen, in a phosphorodiamidate linkage, is typically the ring nitrogen in a morpholine ring structure.

Accordingly, various embodiments of the disclosure include a substantially uncharged antisense morpholino oligomer, composed of morpholino subunits and phosphorus-containing intersubunit linkages joining a morpholino nitrogen of one subunit to a 5'-exocyclic carbon of an adjacent subunit, and having (a) about 10-40 nucleotide bases, and (b) a targeting sequence of sufficient length and complementarity to specifically hybridize to a bacterial mRNA target sequence that encodes a virulence factor; where the oligomer is conjugated to a cell-penetrating peptide (CPP). In particular embodiments, the morpholino subunits are joined by phosphorous-containing intersubunit linkages in accordance with the structure:

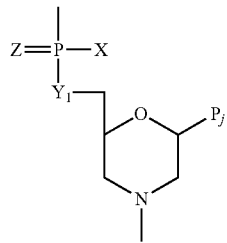

where $Y_1$=oxygen (O) or sulfur, nitrogen, or carbon; Z=oxygen or sulfur, preferably oxygen; Pj is a purine or pyrimidine base-pairing moiety effective to bind, by base-specific hydrogen bonding, to a base in a polynucleotide, and X is —NRR' where R and R' are the same or different and are either H or alkyl. In particular embodiments, X is —NRR', where R and R' are the same or different and are either H or methyl.

Also included are antisense oligomer that comprise a sequence of nucleotides of the formula in FIGS. 1A-1E. In FIG. 1A, B is a purine or pyrimidine base-pairing moiety effective to bind, by base-specific hydrogen bonding, to a base in a polynucleotide. $Y_1$ or $Y_2$ may be oxygen, sulfur, nitrogen, or carbon, preferably oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy include 1-6 carbon atoms. The Z moieties may be sulfur or oxygen, and are preferably oxygen.

In various aspects, an antisense oligomer of the disclosure includes a compound of formula (I):

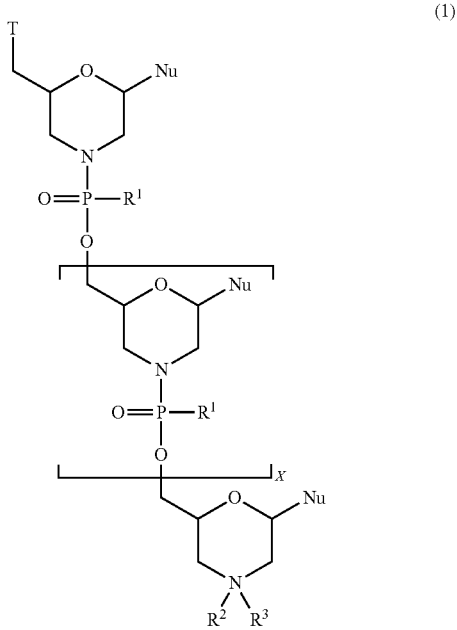

(I)

or a pharmaceutically acceptable salt thereof, where each Nu is a nucleobase which taken together forms a targeting sequence;

X is an integer from 9 to 38;

T is selected from OH and a moiety of the formula:

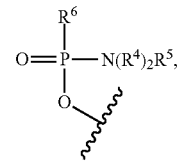

where each $R^4$ is independently $C_1$-$C_6$ alkyl, and $R^5$ is selected from an electron pair and H, and $R^6$ is selected from OH, —N($R^7$)$CH_2$C(O)$NH_2$, and a moiety of the formula:

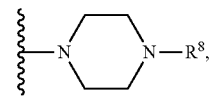

where:

$R^7$ is selected from H and $C_1$-$C_6$ alkyl, and $R^8$ is selected from G, —C(O)—$R^9$OH, acyl, trityl, and 4-methoxytrityl, where:

$R^9$ is of the formula —(O-alkyl)$_y$- wherein y is an integer from 3 to 10 and each of the y alkyl groups is independently selected from $C_2$-$C_6$ alkyl;

each instance of $R^1$ is —N($R^{10}$)$_2$$R^{11}$ wherein each $R^{10}$ is independently $C_1$-$C_6$ alkyl, and $R^{11}$ is selected from an electron pair and H;

$R^2$ is selected from H, G, acyl, trityl, 4-methoxytrityl, benzoyl, stearoyl, and a moiety of the formula:

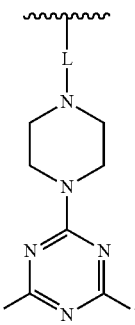

where L is selected from —C(O)(CH$_2$)$_6$C(O)— and —C(O)(CH$_2$)$_2$S$_2$(CH$_2$)$_2$C(O)—, and each $R^{12}$ is of the formula —(CH$_2$)$_2$OC(O)N($R^{14}$)$_2$ wherein each $R^{14}$ is of the formula —(CH$_2$)$_6$NHC(=NH)NH$_2$; and $R^3$ is selected from an electron pair, H, and $C_1$-$C_6$ alkyl, wherein G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

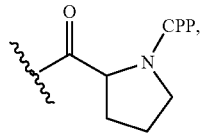

wherein the CPP is attached to the linker moiety by an amide bond at the CPP carboxy terminus, with the proviso that only one instance of G is present, wherein the targeting sequence specifically hybridizes to a bacterial mRNA target sequence that encodes a virulence factor.

In some embodiments, X is from 9 to 18. In certain embodiments, X is 9, 10, 11, 12, 13, 14, 15, 16, 17, 18, 19, 20, 21, 22, 23, 24, 25, 26, 27, 28, 29 or 30.

In certain embodiments, T is selected from:

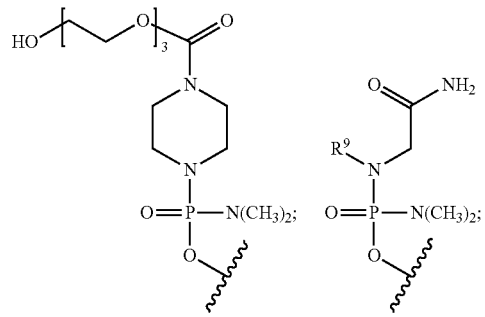

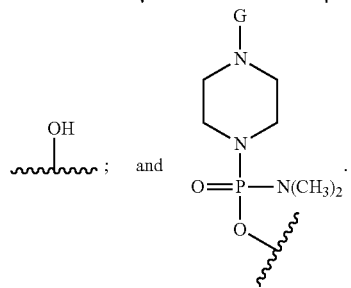

In some embodiments, $R^2$ is selected from H, G, acyl, trityl, 4-methoxytrityl, benzoyl, and stearoyl.

In various embodiments, T is selected from:

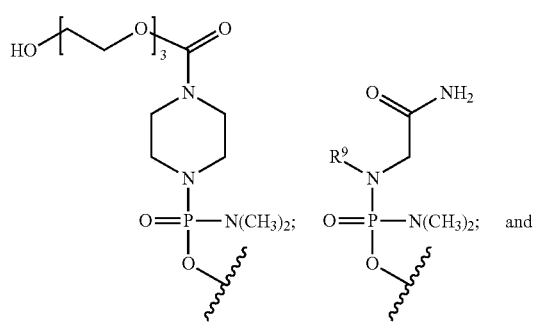

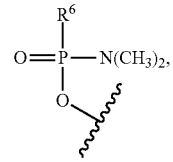

and $R^2$ is G.

In some embodiments, T is of the formula:

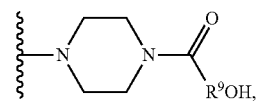

$R^6$ is of the formula:

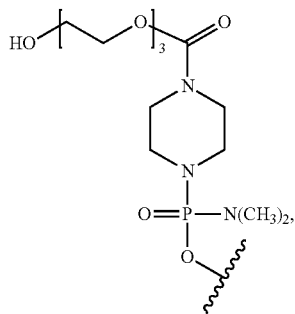

and $R^2$ is G.

In certain embodiments, T is of the formula:

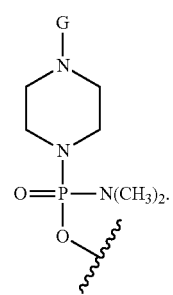

and $R^2$ is G.

In certain embodiments, T is of the formula:

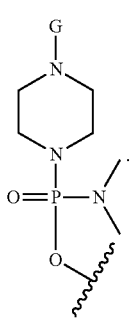

In some embodiments, $R^2$ is G or T is of the formula:

In some embodiments, $R^2$ is selected from H, acyl, trityl, 4-methoxytrityl, benzoyl, and stearoyl.

In various embodiments, $R^2$ is selected from H or G, and $R^3$ is selected from an electron pair or H. In a particular embodiment, $R^2$ is G. In some embodiments, $R^2$ is H or acyl. In some embodiments, each $R^1$ is —$N(CH_3)_2$. In some embodiments, at least one instance of $R^1$ is —$N(CH_3)_2$. In certain embodiments, each instance of $R^1$ is —$N(CH_3)_2$.

In various embodiments of the disclosure, an antisense oligomer of the disclosure includes a compound of formula (II):

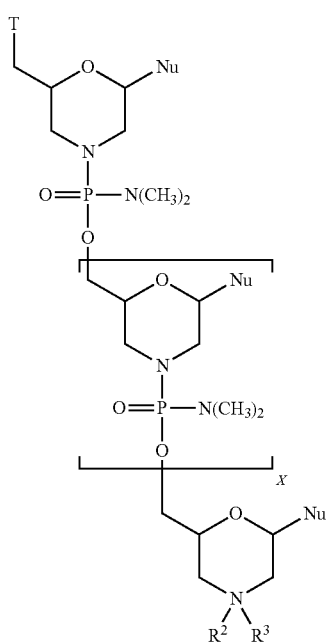

or a pharmaceutically acceptable salt thereof, where each Nu is a nucleobase which taken together forms a targeting sequence;

X is an integer from 9 to 28;

T is selected from:

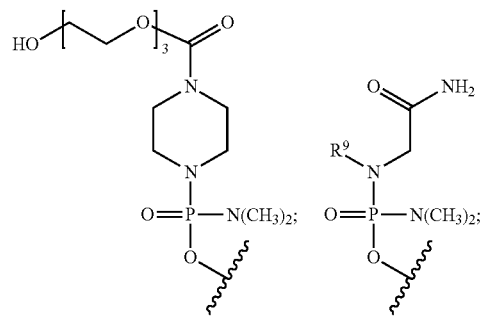

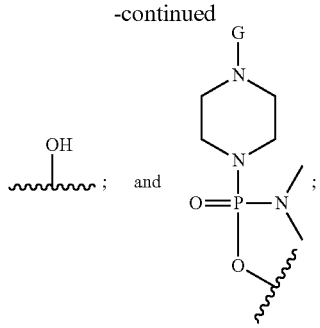

$R^2$ is selected from H, G, acyl, trityl, 4-methoxytrityl, benzoyl, and stearoyl; and $R^3$ is selected from an electron pair, H, and $C_1$-$C_6$ alkyl, wherein G is a cell penetrating peptide ("CPP") and linker moiety selected from —C(O)(CH_2)_5NH—CPP, —C(O)(CH_2)_2NH—CPP, —C(O)(CH_2)_2NHC(O)(CH_2)_5NH—CPP, and —C(O)CH_2NH—CPP, or G is of the formula:

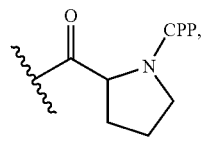

wherein the CPP is attached to the linker moiety by an amide bond at the CPP carboxy terminus, with the proviso that only one instance of G is present. In various embodiments, $R^2$ is G or T is of the formula:

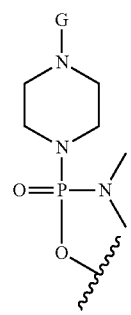

In some embodiments, T is TEG as defined above, $R^2$ is G, and $R^3$ is an electron pair or H. In certain embodiments, $R^2$ is selected from H, acyl, trityl, 4-methoxytrityl, benzoyl, and stearoyl and T is of the formula:

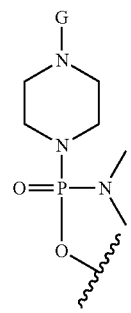

In various aspects, an antisense oligomer of the disclosure includes a compound of formula (III):

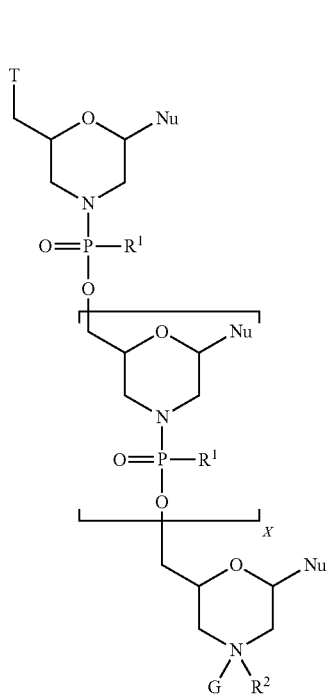

(III)

or a pharmaceutically acceptable salt thereof, where each Nu is a nucleobase which taken together forms a targeting sequence;

X is an integer from 9 to 28;

T is selected from:

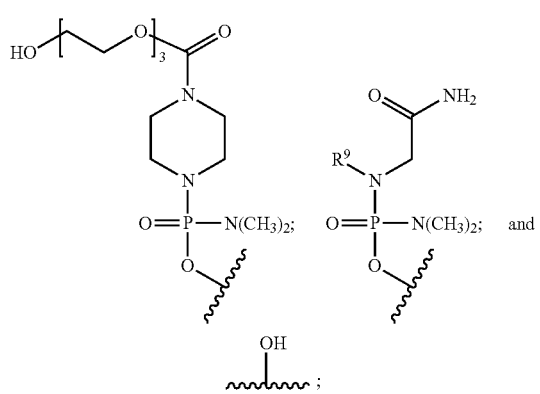

each instance of $R^1$ is —$N(R^{10})_2R^{11}$ wherein each $R^{10}$ is independently $C_1$-$C_6$ alkyl, and $R^{11}$ is selected from an electron pair and H;

$R^2$ is selected from an electron pair, H, and $C_1$-$C_6$ alkyl; and

G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

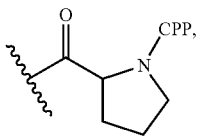

wherein the CPP is attached to the linker moiety by an amide bond at the CPP carboxy terminus.

In some embodiments, at least one instance of $R^1$ is —$N(CH_3)_2$. In certain embodiments, each instance of $R^1$ is —$N(CH_3)_2$.

In various aspects, an antisense oligomer of the disclosure includes a compound of formula (IV):

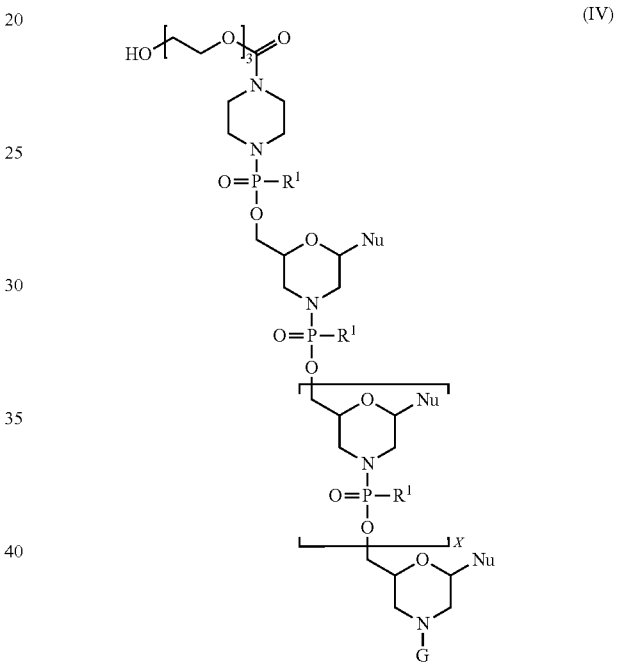

(IV)

or a pharmaceutically acceptable salt thereof, wherein:

X is an integer from 9 to 28;

each Nu is a nucleobase which taken together forms a targeting sequence;

each instance of $R^1$ is —$N(R^{10})_2R^{11}$ wherein each $R^{10}$ is independently $C_1$-$C_6$ alkyl, and $R^{11}$ is selected from an electron pair and H; and G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

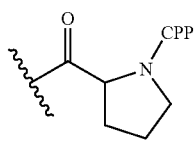

wherein the CPP is attached to the linker moiety by an amide bond at the CPP carboxy terminus. In some embodi- In various aspects, an antisense oligomer of the disclosure can be a compound of formula (V):

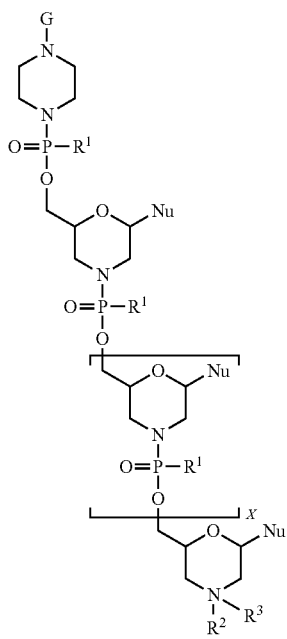

(V)

wherein:

X is an integer from 9 to 18;

each Nu is a nucleobase which taken together forms a targeting sequence;

each instance of $R^1$ is $-N(R^{10})_2R^{11}$ wherein each $R^{10}$ is independently $C_1$-$C_6$ alkyl, and $R^{11}$ is selected from an electron pair and H;

$R^2$ is selected from H, trityl, 4-methoxytrityl, acyl, benzoyl, and stearoyl; and $R^3$ is selected from an electron pair, H, and $C_1$-$C_6$ alkyl, wherein G is a cell penetrating peptide ("CPP") and linker moiety selected from $-C(O)(CH_2)_3NH-CPP$, $-C(O)(CH_2)_2NH-CPP$, $-C(O)(CH_2)_2NHC(O)(CH_2)_3NH-CPP$, and $-C(O)CH_2NH-CPP$, or G is of the formula:

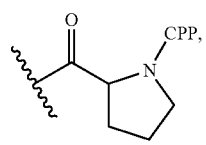

wherein the CPP is attached to the linker moiety by an amide bond at the CPP carboxy terminus. In some embodiments, at least one instance of $R^1$ is $-N(CH_3)_2$. In certain embodiments, each instance of $R^1$ is $-N(CH_3)_2$.

In various aspects, an antisense oligomer of the disclosure includes a compound of formula (VI):

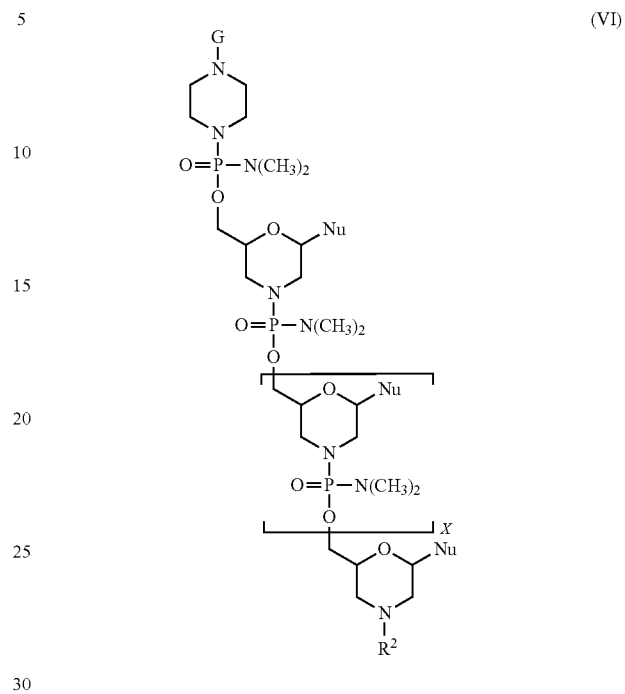

(VI)

or a pharmaceutically acceptable salt thereof, wherein:

X is an integer from 9 to 28;

each Nu is a nucleobase which taken together forms a targeting sequence;

$R^2$ is selected from H or acyl; and

G is a cell penetrating peptide ("CPP") and linker moiety selected from $-C(O)(CH_2)_5NH-CPP$, $-C(O)(CH_2)_2NH-CPP$, $-C(O)(CH_2)_2NHC(O)(CH_2)_5NH-CPP$, and $-C(O)CH_2NH-CPP$, or G is of the formula:

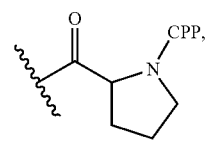

wherein the CPP is attached to the linker moiety by an amide bond at the CPP carboxy terminus.

The antisense oligomers can be prepared by stepwise solid-phase synthesis, employing methods known in the art and described in the references cited herein.

B. Cell-Penetrating Peptides

In certain embodiments, the antisense oligomer is conjugated to a cell-penetrating peptide (CPP). In some embodiments, the CPP is an arginine-rich peptide. By "arginine-rich carrier peptide" is meant that the CPP has at least 2, and preferably 2, 3, 4, 5, 6, 7, or 8 arginine residues, each optionally separated by one or more uncharged, hydrophobic residues, and optionally containing about 6-14 amino acid residues. FIGS. 1F-1H show exemplary chemical structures of CPP-PMO conjugates used in the Examples, including 5' and 3' PMO conjugates.

Exemplary CPPs are provided in Table C1 (SEQ ID NOS: 38-42).

TABLE C1

Exemplary Cell-Penetrating Peptides

| Name | Sequence | SEQ ID NO: |
|---|---|---|
| (RXR)₄ | RXRRXRRXRRXR | 38 |
| (RFF)₃R | RFFRFFRFFR | 39 |
| (RXR)₄XB | RXRRXRRXRRXRXB | 40 |
| (RFF)₃RXB | RFFRFFRFFRXB | 41 |
| (RFF)₃RG | RFFRFFRFFR | 42 |

X is 6-aminohexanoic acid;
B is β-alanine;
F is phenylalanine

CPPs, their synthesis, and methods of conjugating a CPP to an oligomer are detailed, for example, in International Patent Application Publication Nos. WO 2004/097017, WO 2009/005793, and WO 2012/150960, which are all incorporated by reference in their entirety.

In some embodiments, the CPP is linked at its C-terminus to the 3'-end or the 5'-end of the oligomer via a 1, 2, 3, 4, or 5 amino acid linker. In particular embodiments, including antisense oligomer compounds of formula (I)-(VI), the linkers can include: —C(O)(CH₂)₅NH—CPP (X linker), —C(O)(CH₂)₂NH—CPP (B linker), —C(O)(CH₂)₂NHC(O)(CH₂)₅NH—CPP (XB peptide linker), and —C(O)CH₂NH—CPP (Gly linker), or G is of the formula:

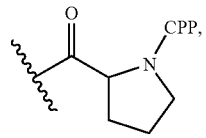

wherein the CPP is attached to the linker moiety by an amide bond at the CPP carboxy terminus. In some embodiments of the disclosure, including antisense oligomer compounds of formula (I)-(VI), G is selected from SEQ ID NOS: 40 to 42.

In various embodiments, including antisense oligomer compounds of formula (I)-(VI), the CPP is selected from SEQ ID NO: 38 and 39, and the linker is selected from the group described above.

In some embodiments, including antisense oligomer compounds of formula (I)-(VI), the CPP is selected from:

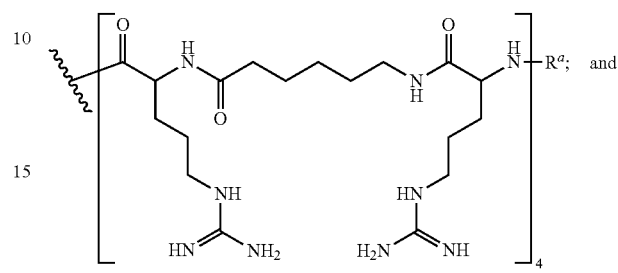

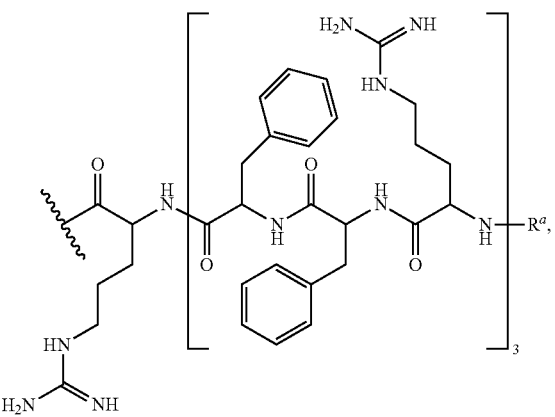

wherein $R^a$ is selected from H, acetyl, benzoyl, and stearoyl.

In some embodiments, including antisense oligomer compounds of formula (I)-(VI), G is selected from:

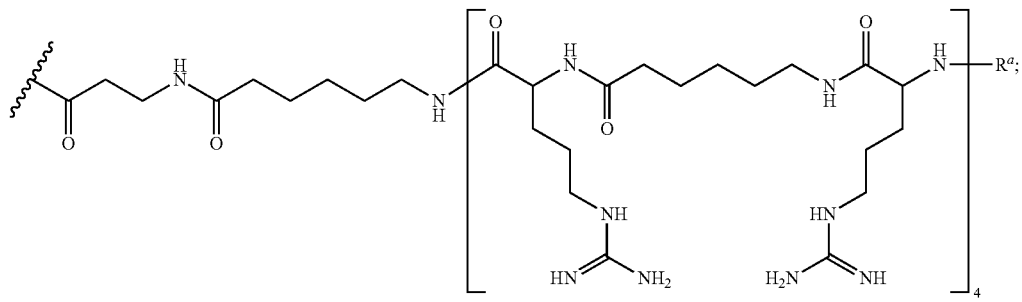

-continued
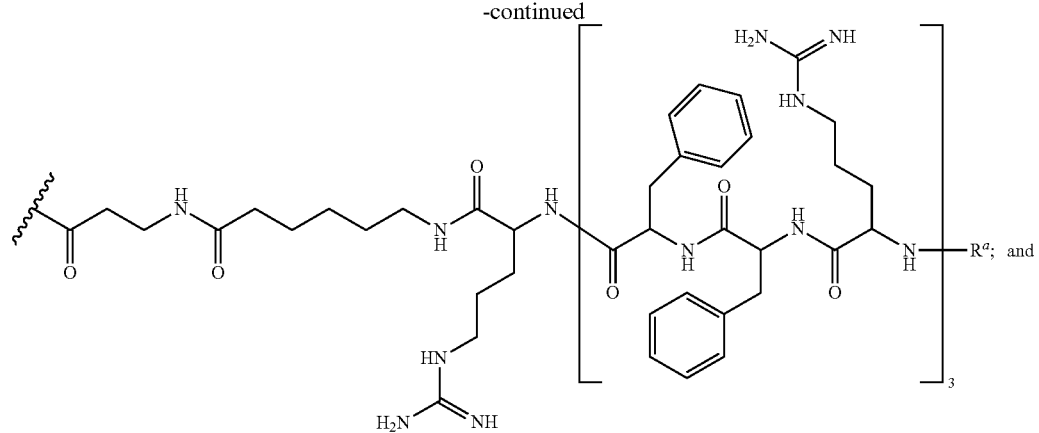
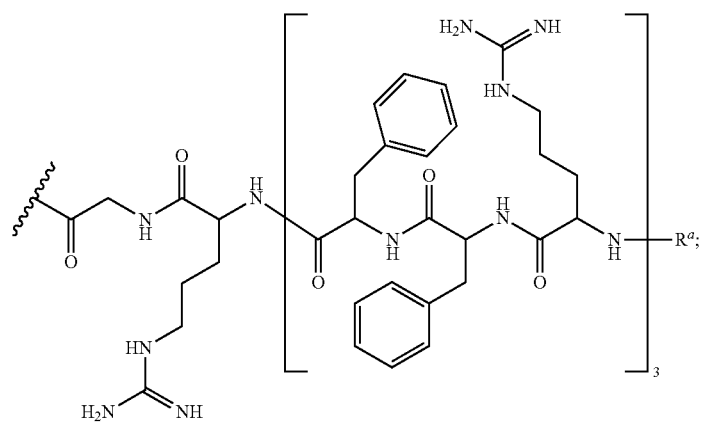
wherein R$^a$ is selected from H, acetyl, benzoyl, and stearoyl.
In various aspects, an antisense oligomer of the disclosure, or a pharmaceutically acceptable salt thereof, includes an antisense oligomer of the formula (VII) selected from:

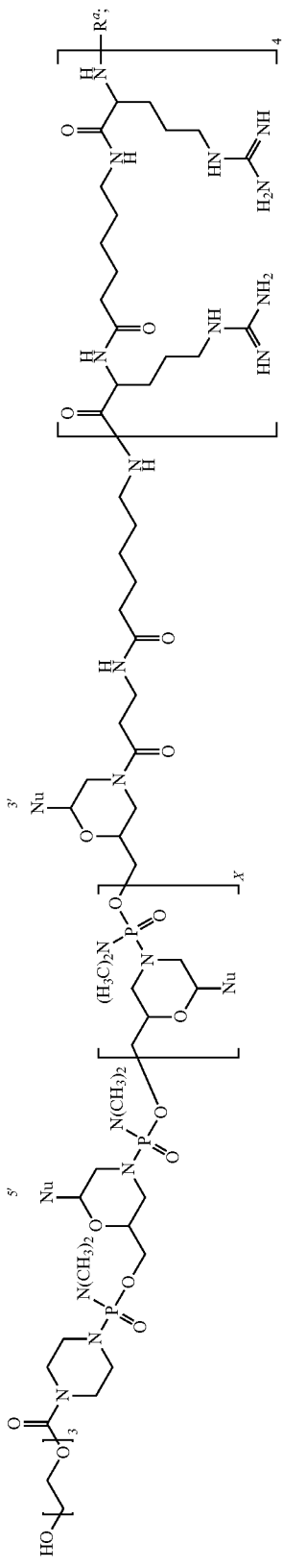
(VII A)
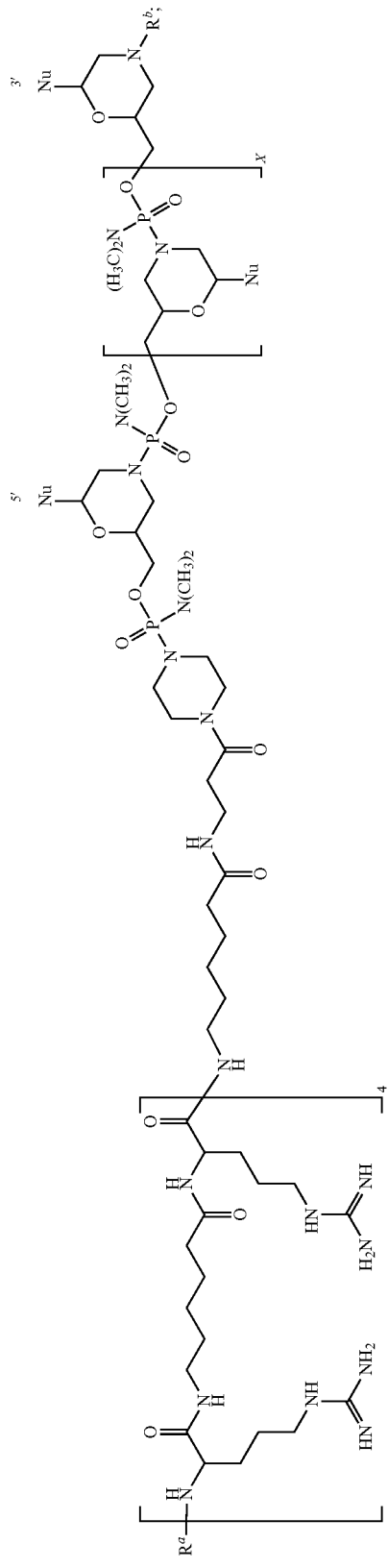
(VII B)

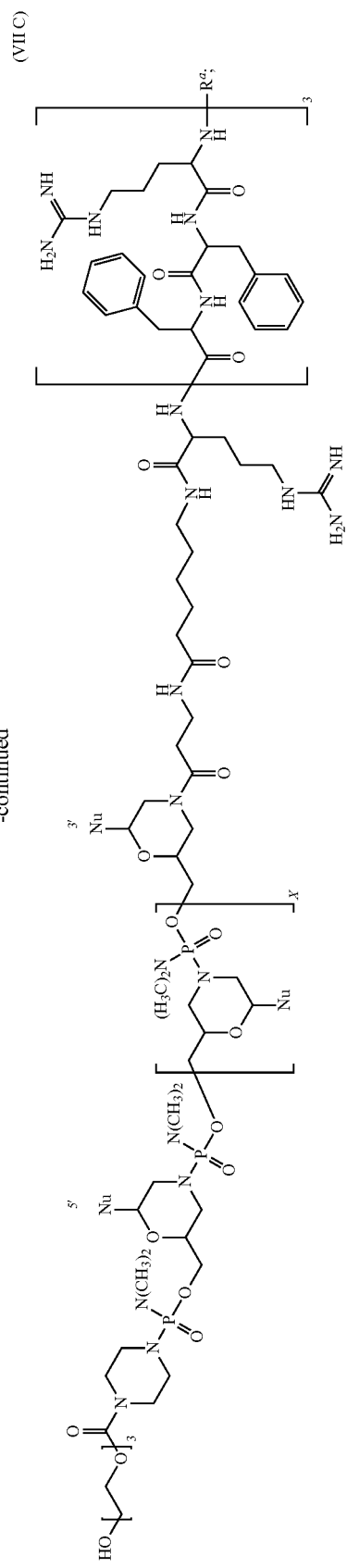
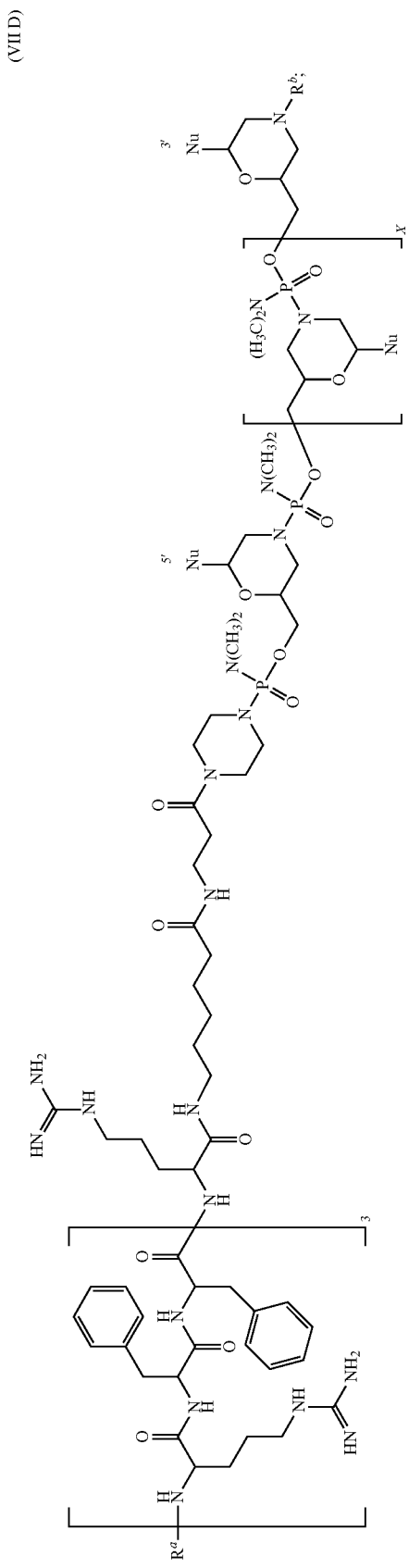

-continued
(VIIE)
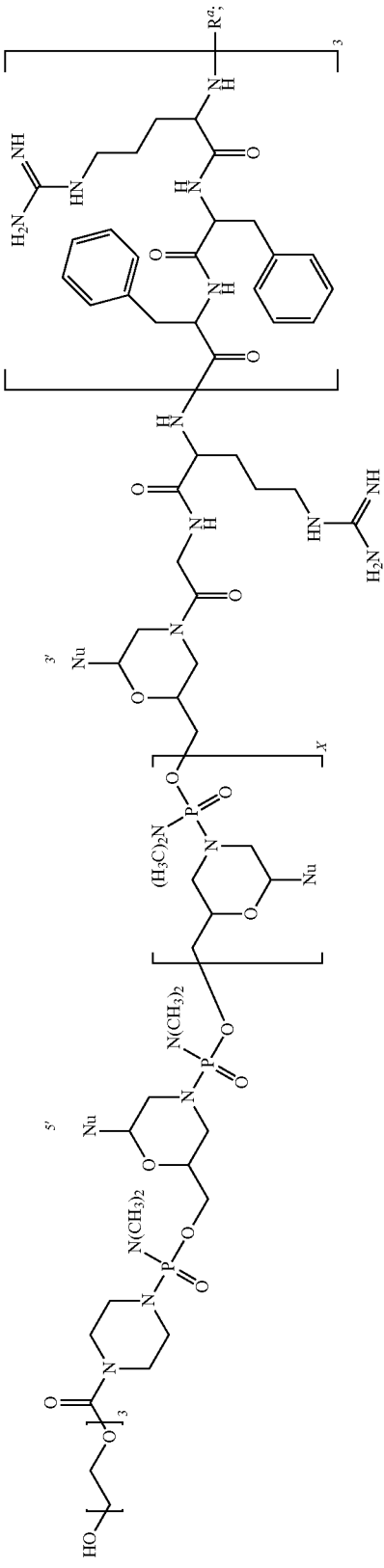
(VIIF)
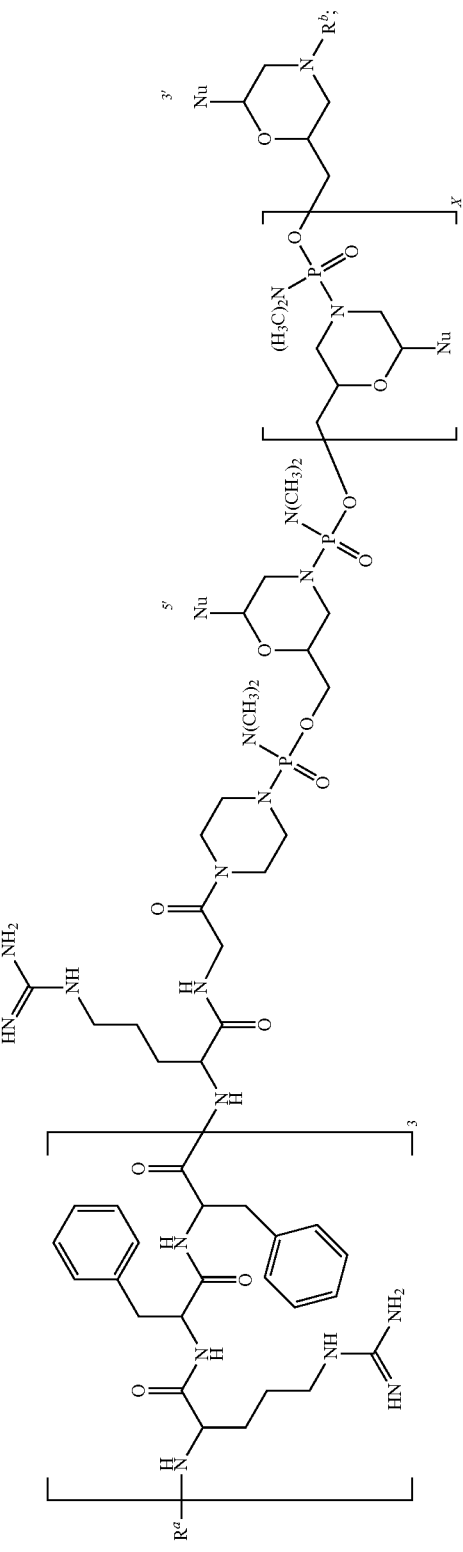

wherein X is an integer from 9 to 38, $R^a$ is selected from H, acetyl, benzoyl, and stearoyl, $R^b$ is selected from H, acetyl, benzoyl, stearoyl, trityl, and 4-methoxytrityl, and each Nu is a purine or pyrimidine base-pairing moiety which taken together form a targeting sequence described above.

C. Antisense Oligomer Targeting Sequence

In various embodiments of the antisense oligomers of the disclosure, including the antisense oligomer compounds of formulas (I)-(VII), the targeting sequence can specifically hybridizes to a bacterial mRNA target sequence that encodes a virulence factor. In some embodiments, the target sequence comprises a translational start codon of the bacterial mRNA and/or a sequence within about 30 bases upstream or downstream of the translational start codon of the bacterial mRNA. In certain embodiments, the virulence factor can be an antibiotic resistance protein or a biofilm formation protein. In some embodiments, the antibiotic resistance protein may be selected from at least one of New Delhi metallo-beta-lactamase (NDM-1) and resistance-nodulation-cell division (RND)-type multidrug efflux pump subunit AdeA (adeA). In some embodiments, the target sequence can be selected from SEQ ID NOS: 1-4, wherein thymine bases (T) are optionally uracil bases (U). In certain embodiments, the targeting sequence may be one of the targeting sequences set forth in SEQ ID NOS: 11-15, may comprise a fragment of at least 10 contiguous nucleotides of SEQ ID NOS: 11-15, or may comprise a variant having at least 80% sequence identity to SEQ ID NOS: 11-15, wherein thymine bases (T) are optionally uracil bases (U). In some embodiments, the biofilm formation protein may be encoded by at least one of CepI or SuhB. In certain embodiments, the target sequence can be selected from SEQ ID NOS: 5-9, wherein thymine bases (T) are optionally uracil bases (U). In some embodiments, the targeting sequence may be one of the targeting sequences set forth in SEQ ID NOS: 16-24, may comprise a fragment of at least 10 contiguous nucleotides of SEQ ID NOS: 16-24, or may comprise a variant having at least 80% sequence identity to SEQ ID NOS: 16-24, wherein thymine bases (T) are optionally uracil bases (U). In various embodiments, the virulence factor is an acyl carrier protein associated with fatty acid biosynthesis encoded by one or more of acpP. In certain embodiments, the acyl carrier protein may be AcpP. In some embodiments, the target sequence may be SEQ ID NO: 10, wherein thymine bases (T) are optionally uracil bases (U). In certain embodiments, the targeting sequence may be one of the targeting sequences set forth in SEQ ID NOS: 25-37, may comprise a fragment of at least 10 contiguous nucleotides of SEQ ID NOS: 25-37, or may comprise a variant having at least 80% sequence identity to SEQ ID NOS: 25-37, wherein thymine bases (T) are optionally uracil bases (U). In some embodiments of the disclosure, including the antisense oligomer compounds of formulas (I)-(VII), the targeting sequence is selected from:

a) SEQ ID NO: 11 (TCA AGT TTT CC);

b) SEQ ID NO: 12 (TCC TTT TAT TC);

c) SEQ ID NO: 13 (CCA TCA AGT TT);

d) SEQ ID NO: 14 (GGC AAT TCC AT); and e) SEQ ID NO: 15 (ATA CTG TCC AA), wherein X is 9, and thymine bases (T) may be uracil bases (U).

In various embodiments of the disclosure, including the antisense oligomer compounds of formulas (I)-(VII), the targeting sequence is selected from:

a) SEQ ID NO: 16 (AAG GTC TGC AT);

b) SEQ ID NO: 17 (TCG GAT CTG TG);

c) SEQ ID NO: 18 (CAT GGA TGT CC);

d) SEQ ID NO: 19 (CGT GAA CGA AG);

e) SEQ ID NO: 20 (CGT GTG GCA AC);

f) SEQ ID NO: 21 (GCC CGA GAT CC);

g) SEQ ID NO: 22 (CTT TCG TTC GC);

h) SEQ ID NO: 23 (ATG CAT GAG CC); and i) SEQ ID NO: 24 (GGA TGC ATG AG), wherein X is 9, and thymine bases (T) may be uracil bases (U).

In certain embodiments of the disclosure, including the antisense oligomer compounds of formulas (I)-(VII), the targeting sequence is selected from:

a) SEQ ID NO: 25 (GTCCATTACCC);

b) SEQ ID NO: 26 (CATTACCCCTC);

c) SEQ ID NO: 27 (CCATTACCCCT);

d) SEQ ID NO: 28 (TCCATTACCCC);

e) SEQ ID NO: 29 (TGTCCATTACC);

f) SEQ ID NO: 30 (TTGTCCATTAC);

g) SEQ ID NO: 31 (GTTGTCCATTA);

h) SEQ ID NO: 32 (TGTTGTCCATT);

i) SEQ ID NO: 33 (ATGTTGTCCAT);

j) SEQ ID NO: 34 (TTTACAAGTGC);

k) SEQ ID NO: 35 (CCTCCGAGGGA);

l) SEQ ID NO: 36 (ACACGTTGTTC);

m) SEQ ID NO: 37 (AGTTCAGCGAC), wherein X is 9, and thymine bases (T) may be uracil bases (U).

D. Exemplary Antisense Oligomers

Exemplary antisense oligomers (AONs) of the disclosure include those described in Tables 3A-3C below.

TABLE 3A

Exemplary Antibiotic Resistance Targeting Sequences AONs

| PMO Name | Target Gene | Targeting Sequence (TS)* | TS SEQ ID NO: | 5' Attachment | 3' Attachment ** | CPP SEQ ID NO. |
|---|---|---|---|---|---|---|
| PPMO#1 | NDM-1 | TCA AGT TTT CC | 11 | TEG | (RXR)$_4$XB- | 40 |
| PPMO#2 | NDM-1 | TCC TTT TAT TC | 12 | TEG | (RXR)$_4$XB- | 40 |
| PPMO#3 | NDM-1 | CCA TCA AGT TT | 13 | TEG | (RXR)$_4$XB- | 40 |
| PPMO#4 | NDM-1 | GGC AAT TCC AT | 14 | TEG | (RXR)$_4$XB- | 40 |
| PPMO#5 | adeA | ATA CTG TCC AA | 15 | TEG | (RXR)$_4$XB- | 40 |

\* The thymines (T) can be uracils (U);
\*\* X is 6-aminohexanoic acid, B is beta-alanine, G is glycine, F is phenylalanine, and TEG is defined above.

TABLE 3B

Exemplary Biofilm Formation Targeting AONs

| PMO Name | Target Gene | Targeting Sequence (TS)* | TS SEQ ID NO: | 5' Attachment *** | 3' Attachment ** | CPP SEQ ID NO. |
|---|---|---|---|---|---|---|
| PPMO#6 | cepI | AAG GTC TGC AT | 16 | (RFF)$_3$RXB- | H | 41 |
| PPMO#7 | cepI | TCG GAT CTG TG | 17 | TEG | (RFF)$_3$RXB- | 41 |
| PPMO#8 | cepI | CAT GGA TGT CC | 18 | TEG | (RFF)$_3$RXB- | 41 |
| PPMO#9 | cepI | CGT GAA CGA AG | 19 | TEG | (RFF)$_3$RXB- | 41 |
| PPMO#10 | cepI | CGT GTG GCA AC | 20 | TEG | (RFF)$_3$RXB- | 41 |
| PPMO#11 | cepI | GCC CGA GAT CC | 21 | TEG | (RFF)$_3$RXB- | 41 |
| PPMO#12 | cepI | CTT TCG TTC GC | 22 | TEG | (RFF)$_3$RXB- | 41 |
| PPMO#13 | suhB | ATG CAT GAG CC | 23 | TEG | (RFF)$_3$RXB- | 41 |
| PPMO#14 | suhB | GGA TGC ATG AG | 24 | TEG | (RFF)$_3$RXB- | 41 |

\* The thymines (T) can be uracils (U);
\*\* X is 6-aminohexanoic acid, B is beta-alanine, G is glycine, F is phenylalanine, and TEG is defined above.
\*\*\* X is 6-aminohexanoic acid, B is beta-alanine, G is glycine, F is phenylalanine, and a 5' CPP is linked through a pip-PDA moiety described above.

TABLE 3C

Exemplary Fatty Acid Biosynthesis-Associated Targeting Sequences AONs

| PMO Name | Target Gene | Targeting Sequence (TS)* | TS SEQ ID NO: | 5' Attachment *** | 3' Attachment ** | CPP SEQ ID NO. |
|---|---|---|---|---|---|---|
| PPMO#15 | acpP | GTCCATTACCC | 25 | (RFF)$_3$RXB- | H | 41 |
| PPMO#16 | acpP | GTCCATTACCC | 25 | TEG | (RFF)$_3$RXB- | 41 |
| PPMO#17 | acpP | GTCCATTACCC | 25 | (RFF)$_3$RG- | H | 42 |
| PPMO#18 | acpP | CATTACCCCTC | 26 | (RFF)$_3$RXB- | H | 41 |
| PPMO#19 | acpP | CCATTACCCCT | 27 | (RFF)$_3$RXB- | H | 41 |
| PPMO#20 | acpP | TCCATTACCCC | 28 | (RFF)$_3$RXB- | H | 41 |
| PPMO#21 | acpP | TGTCCATTACC | 29 | (RFF)$_3$RXB- | H | 41 |
| PPMO#22 | acpP | TTGTCCATTAC | 30 | (RFF)$_3$RXB- | H | 41 |
| PPMO#23 | acpP | GTTGTCCATTA | 31 | (RFF)$_3$RXB- | H | 41 |
| PPMO#24 | acpP | TGTTGTCCATT | 32 | (RFF)$_3$RXB- | H | 41 |

TABLE 3C-continued

Exemplary Fatty Acid Biosynthesis-Associated Targeting Sequences AONs

| PMO Name | Target Gene | Targeting Sequence (TS)* | TS SEQ ID NO: | 5' Attachment *** | 3' Attachment ** | CPP SEQ ID NO. |
|---|---|---|---|---|---|---|
| PPMO#25 | acpP | ATGTTGTCCAT | 33 | (RFF)₃RXB- | H | 41 |
| PPMO#26 | acpP | TTTACAAGTGC | 34 | TEG | (RFF)₃RXB- | 41 |
| PPMO#27 | acpP | CCTCCGAGGGA | 35 | TEG | (RFF)₃RXB- | 41 |
| PPMO#28 | acpP | ACACGTTGTTC | 36 | TEG | (RFF)₃RXB- | 41 |
| PPMO#29 | acpP | AGTTCAGCGAC | 37 | TEG | (RFF)₃RXB- | 41 |

* The thymines (T) can be uracils (U);
** X is 6-aminohexanoicacid, B is beta-alanine, G is glycine, F is phenylalanine, and TEG is defined above.
*** X is 6-aminohexanoic acid, B is beta-alanine, G is glycine, F is phenylalanine, and a 5' CPP is linked through a pip-PDA moiety described above.

II. Methods of Use and Formulations

Embodiments of the present disclosure include methods of using the antisense oligomers described herein to reduce the expression and activity of one or more bacterial virulence factors. Certain embodiments include methods of using the antisense oligomers to reduce replication, proliferation, virulence factors, or growth of bacteria, for example, to treat bacterial infections in a subject, either alone or in combination with one or more additional antimicrobial agents. In some instances, the antisense oligomers increase the susceptibility of the bacterium to antibiotics. Certain embodiments include methods of using the antisense oligomers described herein to reduce the formation or existence of bacterial biofilms, for instance, to treat bacterial infections in a subject, either alone or in combination with one or more additional antimicrobial agents.

Also included are pharmaceutical compositions comprising the antisense oligomers, typically in combination with a pharmaceutically-acceptable carrier. The methods provided herein can be practiced in vitro or in vivo.

For example, certain embodiments include methods of treating a bacterial infection in a subject, comprising administering to a subject in need thereof (e.g., subject having or at risk for having a bacterial infection) an antisense oligomer or pharmaceutical composition described herein. Also included are methods of reducing virulence and/or biofilm formation of a bacteria or bacterium which comprises a gene encoding a virulence factor, comprising contacting the bacteria or bacterium with an antisense oligomer described herein.

In some embodiments, the bacterium is selected from the genus Escherichia, Acinetobacter, Klebsiella, Burkholderia, and Pseudomonas.

Escherichia is a genus of Gram-negative, non-spore forming, facultatively anaerobic, rod-shaped bacteria from the family Enterobacteriaceae, and includes the species Escherichia coli, which is responsible for the vast majority of Escherichia-related pathogenesis.

Acinetobacter is a genus of Gram-negative bacteria belonging to the class of Gammaproteobacteria. Examples of clinically-relevant Acinetobacter complexes include the Acinetobacter calcoaceticus-baumanii complex (glucose-oxidizing nonhemolytic), Acinetobacter lwoffii (glucose-negative nonhemolytic), and Acinetobacter haemolyticus (hemolytic). Specific examples include Acinetobacter baumannii.

Klebsiella is a genus of non-motile, Gram-negative, oxidase-negative, rod-shaped bacteria with a prominent polysaccharide-based capsule. Klebsiella organisms can lead to a wide range of disease states, such as pneumonia, urinary tract infections, septicemia, meningitis, diarrhea, and soft tissue infections. The majority of human infections are caused by Klebsiella pneumoniae and Klebsiella oxytoca.

Burkholderia (previously part of Pseudomonas) refers to a group of near ubiquitous gram-negative, motile, obligately aerobic rod-shaped bacteria. These protobacteria include pathogenic bacteria such as Burkholderia mallei, responsible for glanders; Burkholderia pseudomallei, causative agent of melioidosis; and Burkholderia cepacia, a significant pathogen of pulmonary infections, for example, in subjects with cystic fibrosis (CF). Burkholderia cepacia (or Burkholderia cepacia complex) is a Gram-negative bacterium composed of many different sub-species, including, for example, Burkholderia cenocepacia, Burkholderia multivorans, Burkholderia vietnamiensis, Burkholderia stabilis, Burkholderia anthina, Burkholderia pyrrocinia, Burkholderia dolosa, and/or Burkholderia ambifaria.

Pseudomonas is a genus of Gram-negative aerobic gammaproteobacteria, belonging to the family Pseudomonadaceae. Pseudomonas aeruginosa is increasingly recognized as an emerging opportunistic pathogen of clinical relevance. It has low antibiotic susceptibility and can form biofilms. Pseudomonas spp. are naturally resistant to penicillin and the majority of related beta-lactam antibiotics, but some are sensitive to piperacillin, imipenem, ticarcillin, and/or ciprofloxacin. Aminoglycosides such as tobramycin, gentamicin, and amikacin are other potential microbial agents for the treatment of Pseudomonas infections.

Thus, in some embodiments, the bacterium is any of the foregoing members of the genera Escherichia, Acinetobacter, Klebsiella, Burkholderia, and Pseudomonas. In specific embodiments, the bacterium is one or more of Escherichia coli, Acinetobacter baumannii, Klebsiella pneumoniae, Burkholderia cepacia (complex), or Pseudomonas aeruginosa.

In certain embodiments, the bacterium is multi-drug resistance (MDR) bacteria or bacterium. Multiple drug resistance (MDR), multi-drug resistance or multiresistance is a condition enabling disease-causing microorganisms (bacteria, viruses, fungi or parasites) to resist distinct antimicrobials such as antibiotics, antifungal drugs, antiviral medications, antiparasitic drugs, and others. In particular embodiments, the bacterium is extensively-drug resistant (XDR) or pan-drug resistant (PDR). In some embodiments, the bacterium is an extended-spectrum β-lactamase (ESBLs) producing Gram-negative bacteria, *Klebsiella pneumoniae* carbapenemase (KPC) producing Gram-negative bacteria, or a multi-drug-resistant gram negative rod (MDR GNR) MDRGN bacteria. In specific embodiments, the bacterium is MDR *Escherichia coli*, MDR *Acinetobacter baumannii*, MDR *Klebsiella pneumoniae*, MDR *Burkholderia cepacia* (complex), or MDR *Pseudomonas aeruginosa*.

As noted above, the bacteria or bacterium described herein typically comprise (e.g., encode) one or more virulence factors such as antibiotic resistance genes, biofilm formation genes and/or genes associated with fatty acid biosynthesis. General examples of antibiotic resistance genes (and their related proteins) include beta-lactamases, which can enzymatically deactivate certain antimicrobial agents, and genes/proteins which increase the permeability or active efflux (pumping out) of an antimicrobial agent. Particular examples of antibiotic resistance genes include New Delhi metallo-beta-lactamase (NDM-1) and resistance-nodulation-cell division (RND)-type multidrug efflux pump subunit AdeA (adeA). In specific embodiments, the bacterium is *Escherichia coli, Acinetobacter baumannii*, or *Klebsiella pneumoniae*, which comprises or expresses at least one antibiotic resistance gene selected from NDM-1 and adeA.

Examples of biofilm formation genes (and their related proteins) include cepI, cepR, and/or suhB genes, for example, from *Burkholderia*. In particular embodiments, the bacterium comprises or expresses the cepI gene, which encodes an acylhomoserine lactone synthase. In some embodiments, the bacterium comprises or expresses the suhB gene, which encodes an inositol-1-monophosphate. In specific embodiments, the bacterium that comprises or expresses one more biofilm formation genes is a *Burkholderia* species, for example, *Burkholderia cepacia* or *Burkholderia cepacia* (complex). In some of these and related embodiments, the subject in need thereof is immunocompromised and has an underlying lung disease, such as cystic fibrosis (CF) or chronic granulomatous disease (CGD).

Examples of genes associated with fatty acid biosynthesis (and their related proteins) include acpP, acpS, and/or fob genes, for example, from *Burkholderia*. In particular embodiments, the bacterium comprises or expresses the acpP gene, which encodes an acyl carrier protein. In specific embodiments, the bacterium that comprises or expresses one or more genes associated with fatty acid biosynthesis is a *Burkholderia* species, for example, *Burkholderia cepacia* or *Burkholderia cepacia* (complex). In some of these and related embodiments, the subject in need thereof is immunocompromised and has an underlying lung disease, such as cystic fibrosis (CF) or chronic granulomatous disease (CGD).

In some embodiments, the antisense oligomer reduces or inhibits the growth of the bacterium. For instance, in some embodiments, the antisense oligomer reduces growth of the bacterium by about or at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to a control (e.g., absence of the antisense oligomer, scrambled oligomer, prior to contacting with the oligomer), or by about or at least about 2, 3, 4, 5, 6, 7, 8, 9, 10, 15, 20, 25, 30, 35, 40, 45, 50, 55, 60, 65, 70, 75, 80, 85, 90, 95, or 100-fold or more (including all integers and ranges in between), relative to a control. Bacterial growth can be measured in vitro (see, e.g., the Examples) or in vivo. In some embodiments, as described herein, the antisense oligomer is employed in combination with one or more antimicrobial agents.

In some embodiments, the antisense oligomer reduces beta-lactamase (e.g., carbapenemase) activity in the periplasm of the bacterium by about or at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to a control, or by at least about 2, 3, 4, 5, 6, 7, 8, 9, 10, 15, 20, 25, 30, 35, 40, 45, 50, 55, 60, 65, 70, 75, 80, 85, 90, 95, or 100-fold or more (including all integers and ranges in between), relative to a control. In some embodiments, the antisense oligomer reduces meropenemase enzymatic activity in the periplasm of the bacterium. In particular embodiments, the antisense oligomer that reduces beta-lactamase (e.g., carbapenemase) activity is targeted against NDM-1, and the bacterium is an *Acinetobacter, Escherichia*, or *Klebsiella* species, for example, *Escherichia coli, Acinetobacter baumannii*, or *Klebsiella pneumoniae* which comprises or expresses NDM-1. These are exemplary bacterial species and it is expected that any bacterium expressing the NDM-1 gene is susceptible to the compounds and methods described herein. Beta-lactamase (e.g., carbapenemase) activity can be measured according to routine techniques in the art.

In some embodiments, the antisense oligomer reduces biofilm formation and/or the levels of existing biofilm relative to a control (e.g., absence of the oligomer). For instance, in some embodiments, the antisense oligomer reduces biofilm formation and/or the levels of existing biofilm by at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to a control, or by at least about 2, 3, 4, 5, 6, 7, 8, 9, 10, 15, 20, 25, 30, 35, 40, 45, 50, 55, 60, 65, 70, 75, 80, 85, 90, 95, or 100-fold or more (including all integers and ranges in between), relative to a control. In particular embodiments, the antisense oligomer that reduces biofilm formation and/or the levels of existing biofilm is targeted against cepI, cepR, suhB, and/or acpP, and the bacterium is a *Burkholderia* species, for example, *Burkholderia cepacia* (complex) or a sub-species thereof (e.g., *Burkholderia cenocepacia, Burkholderia multivorans, Burkholderia vietnamiensis, Burkholderia stabilis, Burkholderia anthina, Burkholderia pyrrocinia, Burkholderia dolosa, Burkholderia ambifaria*), which comprises or expresses cepI, cepR, suhB and/or acpP. Biofilm formation and/or the levels of existing biofilm can be measured in vitro (see, e.g., the Examples) or in vivo.

In some embodiments, the methods are practiced in vivo, and comprise administering the antisense oligomer to a subject in need thereof, for example, a subject in need thereof that is infected or at risk for being infected by one or more of the bacteria or bacterium described herein. The antisense oligomers of the disclosure can thus be administered to subjects to treat (prophylactically or therapeutically) an infection by any of the bacteria or bacterium described herein. In conjunction with such treatment, pharmacogenomics (e.g., the study of the relationship between an individual's genotype/phenotype and that individual's response to a foreign compound or drug) may be considered. Differences in metabolism of therapeutics can lead to severe toxicity or therapeutic failure by altering the relation between dose and blood concentration of the pharmacologically active drug.

Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

Effective delivery of the antisense oligomer to the target nucleic acid is one aspect of treatment. Routes of antisense oligomer delivery include, but are not limited to, various systemic routes, including oral and parenteral routes, e.g., intravenous, subcutaneous, intraperitoneal, and intramuscular, as well as inhalation, transdermal, and topical delivery. The antisense oligomer may be aerosolized for delivery. The appropriate route may be determined by one of skill in the art, as appropriate to the condition of the subject under treatment. Vascular or extravascular circulation, the blood or lymph system, and the cerebrospinal fluid are some non-limiting sites where the antisense oligomers may be introduced. Direct CNS delivery may be employed, for instance, intracerebral, intraventricular, or intrathecal administration may be used as routes of administration.

In certain embodiments, the antisense oligomers of the disclosure can be delivered by transdermal methods (e.g., via incorporation of the antisense oligomers into, e.g., emulsions, with such antisense oligomers optionally packaged into liposomes). Such transdermal and emulsion/liposome-mediated methods of delivery are described for delivery of antisense oligomers in the art, e.g., in U.S. Pat. No. 6,965,025, the contents of which are incorporated in their entirety by reference herein.

In certain embodiments, the antisense oligomers of this disclosure can be delivered by aerosolization. Advantages to administering medications to the lung as an aerosol include: a more rapid onset of action compared to oral therapy; high local concentration by delivery directly to the airways; needle-free systemic delivery of drugs with poor oral bioavailability; and pain- and needle-free delivery for drugs that require subcutaneous or intravenous injection. Traditional aerosol therapies with the lung as the target consist of short-acting β2-adrenergic agonists and long-acting β2-adrenergic agonists (LABA), anticholinergics, inhaled corticosteroids (ICSs), nonsteroidal antiinflammatories, antibiotics and mucolytics. Devices that deliver these drugs include pressurized metered-dose inhalers (pMDIs), used either alone, or attached to spacers, or valved holding chambers (VHCs), breathactuated (BA)-pMDIs, dry powder inhalers (DPIs), jet nebulizers, vibrating mesh nebulizers and soft mist inhalers. Well-established treatment guidelines for the management of asthma and chronic obstructive pulmonary disease (COPD) each recommend inhaled therapy as the primary route to administer these medications. Treatment guidelines for cystic fibrosis (CF) also include recommendations for inhalation of aerosolized medications.

The antisense oligomers described herein may also be delivered via an implantable device. Design of such a device is an art-recognized process, with, e.g., synthetic implant design described in, e.g., U.S. Pat. No. 6,969,400, the contents of which are incorporated by reference.

Antisense oligomers can be introduced into cells using art-recognized techniques (e.g., transfection, electroporation, fusion, liposomes, colloidal polymeric particles and viral and non-viral vectors as well as other means known in the art). The method of delivery selected will depend at least on the oligomer chemistry, the cells to be treated and the location of the cells and will be apparent to the skilled artisan. For instance, localization can be achieved by liposomes with specific markers on the surface to direct the liposome, direct injection into tissue containing target cells, specific receptor-mediated uptake, or the like.

As known in the art, antisense oligomers may be delivered using, e.g., methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (see, e.g., Dokka and Rojanasakul, Advanced Drug Delivery Reviews 44:35-49, incorporated by reference in its entirety).

The antisense oligomers may be administered in any convenient vehicle or carrier which is physiologically and/or pharmaceutically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration. "Pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions The compounds (e.g., antisense oligomers, antimicrobial agents) described herein may generally be utilized as the free acid or free base. Alternatively, the compounds of this disclosure may be used in the form of acid or base addition salts. Acid addition salts of the free amino compounds of the present disclosure may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids.

Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" is intended to encompass any and all acceptable salt forms.

In addition, prodrugs are also included within the context of this disclosure. Prodrugs are any covalently bonded carriers that release a compound in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this disclosure wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the antisense oligomers of the disclosure. Further, in the case of a carboxylic acid (—COOH), esters may be employed, such as methyl esters, ethyl esters, and the like.

In some instances, liposomes may be employed to facilitate uptake of the antisense oligomer into cells (see, e.g., Williams, S. A., Leukemia 10(12):1980-1989, 1996; Lappalainen et al., Antiviral Res. 23:119, 1994; Uhlmann et al., antisense oligomers: a new therapeutic principle, Chemical Reviews, Volume 90, No. 4, 25 pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligomers may be administered in microspheres or microparticles. (See, e.g., Wu, G. Y. and Wu, C. H., J. Biol. Chem. 262:4429-4432, 30 1987). Alternatively, the use of gas-filled microbubbles complexed with the antisense oligomers can enhance delivery to target tissues, as described in U.S. Pat. No. 6,245,747. Sustained release compositions may also be used. These may include semipermeable polymeric matrices in the form of shaped articles such as films or microcapsules.

In certain embodiments, the antisense oligomer is administered to a mammalian subject, e.g., human or domestic animal, exhibiting the symptoms of a bacterial infection (e.g., antibiotic resistance or MDR bacterial infection), in a suitable pharmaceutical carrier. In some aspects, the subject is a human subject, e.g., a patient diagnosed as having a bacterial infection. In particular embodiments, the antisense oligomer is contained in a pharmaceutically acceptable carrier, and is delivered orally. In some embodiments, the antisense oligomer is contained in a pharmaceutically acceptable carrier, and is delivered intravenously (i.v.).

In some embodiments, the antisense oligomer is administered in an amount and manner effective to result in a peak blood concentration of at least 200-400 nM antisense oligomer. Typically, one or more doses of antisense oligomer are administered, generally at regular intervals, for a period of about one to two weeks. Certain doses for oral administration are from about 1-1000 mg oligomer per 70 kg. In some cases, doses of greater than 1000 mg oligomer/patient may be necessary. For i.v. administration, some doses are from about 0.5 mg to 1000 mg oligomer per 70 kg. The antisense oligomer may be administered at regular intervals for a short time period, e.g., daily for two weeks or less. However, in some cases the antisense oligomer is administered intermittently over a longer period of time. Administration may be followed by, or concurrent with, administration of an antimicrobial (e.g., antibiotic) or other therapeutic treatment, as described herein. The treatment regimen may be adjusted (dose, frequency, route, etc.) as indicated, based on the results of immunoassays, other biochemical tests and physiological examination of the subject under treatment.

An effective in vivo treatment regimen using the antisense oligomers of the disclosure may vary according to the duration, dose, frequency and route of administration, as well as the condition of the subject under treatment (i.e., prophylactic administration versus administration in response to localized or systemic infection). Accordingly, such in vivo therapy will often include monitoring by tests appropriate to the particular type of disorder or bacterial infection under treatment, and corresponding adjustments in the dose or treatment regimen, in order to achieve an optimal therapeutic outcome.

Treatment may be monitored, e.g., by general indicators of disease known in the art. The efficacy of an in vivo administered antisense oligomer of the disclosure may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of a mutant mRNA in relation to a reference normal mRNA or protein as determined by standard techniques such as RT-PCR, Northern blotting, ELISA or Western blotting.

III. Combination Therapies

Certain embodiments include combination therapies, for example, the administration of antisense oligomers in combination with antimicrobial agents such as antibiotics. Combination therapies can be employed, for example, to increase the sensitivity or susceptibility of a given bacteria to one or more antimicrobial agents, and thereby improve the therapeutic outcome (e.g., resolution of the infection). Likewise, certain combination therapies can be employed, for example, to reduce or reverse the antibiotic resistance of a given bacteria to one or more antimicrobial agents. In particular embodiments, the antisense oligomer reduces the minimum inhibitory concentration (MIC) of an antibiotic against a bacterium. Also included are pharmaceutical compositions, as described herein, which comprise an antisense oligomer and an antimicrobial agent such as antibiotic.

In some embodiments, the antisense oligomer and the antimicrobial agent are administered separately. In certain embodiments, the antisense oligomer and the antimicrobial agent are administered sequentially. In some embodiments, the antisense oligomer and the antimicrobial agent are administered concurrently, for example, as part of the same or different pharmaceutical composition.

Examples of antimicrobial agents (e.g., antibiotics) that can be administered in combination with an antisense oligomer include beta-lactam antibiotics such as carbapenems, penicillin and penicillin derivatives (or penams), cephalosporins (e.g., Cefacetrile (cephacetrile), Cefadroxil (cefadroxyl; Duricef), Cephalexin (cefalexin; Keflex), Cefaloglycin (cephaloglycin), Cefalonium (cephalonium), Cefaloridine (cephaloradine), Cefalotin (cephalothin; Keflin), Cefapirin (cephapirin; Cefadryl), Cefatrizine, Cefazaflur, Cefazedone, Cefazolin (cephazolin; Ancef, Kefzol), Cefradine (cephradine; Velosef), Cefroxadine, Ceftezole, Cefaclor (Ceclor, Distaclor, Keflor, Raniclor), Cefonicid (Monocid), Cefprozil (cefproxil; Cefzil), Cefuroxime (Zefu, Zinnat, Zinacef, Ceftin, Biofuroksym, Xorimax), Cefuzonam, Cefmetazole, Cefotetan, Cefoxitin, loracarbef (Lorabid); Cephamycins: cefbuperazone, cefmetazole (Zefazone), cefminox, cefotetan (Cefotan), cefoxitin (Mefoxin), Cefotiam (Pansporin), Cefcapene, Cefdaloxime, Cefdinir (Sefdin, Zinir, Omnicef, Kefnir), Cefditoren, Cefetamet, Cefixime (Fixx, Zifi, Suprax), Cefmenoxime, Cefodizime, Cefotaxime (Claforan), Cefovecin (Convenia), Cefpimizole, Cefpodoxime (Vantin, PECEF), Cefteram, Ceftibuten (Cedax), Ceftiofur, Ceftiolene, Ceftizoxime (Cefizox), Ceftriaxone (Rocephin), Cefoperazone (Cefobid), Ceftazidime (Meezat, Fortum, Fortaz), latamoxef (moxalactam), Cefclidine, cefepime (Maxipime), cefluprenam, cefoselis, Cefozopran, Cefpirome (Cefrom), Cefquinome, flomoxef, Ceftobiprole, Ceftaroline, Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftioxide, Cefuracetime), and monobactams (e.g., aztreonam, tigemonam, nocardin A, tabtoxin); aminoglycosides such as tobramycin, gentamicin, kanamycin a, amikacin, dibekacin, sisomicin, netilmicin, neomycin B, neomycin C, neomycin E (paromomycin), and streptomycin; tetracyclines such as tetracycline, chlortetracycline, oxytetracycline, demeclocycline, lymecycline, meclocycline, methacycline, minocycline, rolitetracycline, and doxycyline; sulfonamides such as sulfacetamide, sulfadiazine, sulfadimidine, sulfafurazole, sulfisomidine, sulfadoxine, sulfamethoxazole, sulfamoxole, sulfadimethoxine, sulfamethoxypyridazine, sulfametoxydiazine, sulfadoxine, and sulfametopyrazine; quinolones such as cinoxacin, nalidixic acid, oxolinic acid (Uroxin), piromidic acid (Panacid), pipemidic acid (Dolcol) rosoxacin (Eradacil), ciprofloxacin (Alcipro, Ciprobay, Cipro, Ciproxin, ultracipro), enoxacin (Enroxil, Penetrex), fleroxacin (Megalone, Roquinol), lomefloxacin (Maxaquin), nadifloxacin (Acuatim, Nadoxin, Nadixa), norfloxacin (Lexinor, Noroxin, Quinabic, Janacin), ofloxacin (Floxin, Oxaldin, Tarivid), pefloxacin (Peflacine), rufloxacin (Uroflox), balofloxacin (Baloxin), grepafloxacin (Raxar), levofloxacin (Cravit, Levaquin, Tavanic), pazufloxacin (Pasil, Pazucross), sparfloxacin (Zagam), temafloxacin (Omniflox), tosufloxacin (Ozex, Tosacin), clinafloxacin, gatifloxacin (Zigat, Tequin) (Zymar-opth.), gemifloxacin (Factive), moxifloxacin (Acflox Woodward, Avelox, Vigamox, sitafloxacin (Gracevit), trovafloxacin (Trovan), prulifloxacin (Quisnon); oxazolidinones such as eperezolid, linezolid, posizolid, radezolid, ranbezolid, sutezolid, and tedizolid; polymyxins such as polysporin, neosporin, polymyxin B, polymyxin E (colistin); rifamycins such as rifampicin or rifampin, rifabutin, rifapentine, and rifaximin; lipiarmycins such as fidaxomicin; macrolides such as azithromycin, clarithromycin, dirithromycin, erythromycin, roxithromycin, telithromycin, carbomycin A, josamycin, kitasamycin, midecamycin/midecamycin acetate, oleandomycin, solithromycin, spiramycin, and troleandomycin; lincosamides such as lincomycin, clindamycin, and pirlimycin; cyclic lipopeptides such as daptomycin; glycopeptides such as vancomycin and teichoplanin; glycylcyclines such as tigecycline. Thus, any one or more of the foregoing antibiotics can be combined with any of the antisense oligomers described herein, for the treatment of any of the bacteria described herein.

In some embodiments, the antimicrobial agent is a beta-lactam antibiotic, as described herein. In certain of these and related embodiments, the bacterium comprises or expresses a beta-lactamase such as NDM-1, and the antisense oligomer is targeted against the beta-lactamase. In particular embodiments, the antimicrobial agent is a carbapenem. Examples of carbapenems include meropenem, imipenem, ertapenem, doripenem, panipenem, biapenem, razupenem, tebipenem, lenapenem, and tomopenem. In certain of these and related embodiments, the bacterium comprises or expresses a carbapenemase such as NDM-1, and the antisense oligomer is targeted against the carbapenemase. In specific embodiments, the bacterium is *Escherichia coli, Acinetobacter baumannii*, or *Klebsiella pneumoniae*.

In some embodiments, the antimicrobial agent is an aminoglycoside such as tobramycin or gentamicin or a tetracycline, as described herein. In some of these and related embodiments, the bacterium comprises or expresses the antibiotic resistance gene adeA, and the antisense oligomer is targeted against the antibiotic resistance gene. In specific embodiments, the bacterium is *Escherichia coli, Acinetobacter baumannii*, or *Klebsiella pneumoniae*.

In certain embodiments, the antimicrobial agent includes one or more of ceftazidime, doxycycline, piperacillin, meropenem, chloramphenicol, and/or co-trimoxazole (trimethoprim/sulfamethoxazole). In some of these and related embodiments, the bacterium is a *Burkholderia* species that comprises or expresses one or more biofilm formation genes such as cepI, cepR, and/or suhB, and the antisense oligomer is targeted against the biofilm formation gene(s). In specific embodiments, the bacterium is *Burkholderia cepacia* or a *Burkholderia cepacia* complex. In specific embodiments, the subject is immunocompromised and has an underlying lung disease, such as cystic fibrosis (CF) or chronic granulomatous disease (CGD).

In certain embodiments, the antimicrobial agent includes one or more of ceftazidime, doxycycline, piperacillin, minocycline, meropenem, chloramphenicol, and/or co-trimoxazole (trimethoprim/sulfamethoxazole). In some of these and related embodiments, the bacterium is a *Burkholderia* species that comprises or expresses one or more genes associated with fatty acid biosynthesis such as acpP, and the antisense oligomer is targeted against the gene(s) encoding an acyl carrier protein. In specific embodiments, the bacterium is *Burkholderia cepacia* or a *Burkholderia cepacia* complex. In specific embodiments, the subject is immunocompromised and has an underlying lung disease, such as cystic fibrosis (CF) or chronic granulomatous disease (CGD).

In some embodiments, the antisense oligomer increases the sensitivity of a given bacteria to the antimicrobial agent, relative to the antimicrobial agent alone. For example, in certain embodiments, the antisense oligomer increases the sensitivity of the bacterium to the antimicrobial agent by increasing the bactericidal (cell-killing) and/or bacteriostatic (growth-slowing) activity of the antimicrobial agent against the bacterium being targeted, relative to the antimicrobial agent alone. In particular embodiments, the antisense increases the sensitivity by about or at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to the antimicrobial agent alone, or by about or at least about 2, 3, 4, 5, 6, 7, 8, 9, 10, 15, 20, 25, 30, 35, 40, 45, 50, 55, 60, 65, 70, 75, 80, 85, 90, 95, or 100-fold or more (including all integers and ranges in between), relative to the antimicrobial agent alone.

In some embodiments, the antisense oligomer reduces the minimum inhibitory concentration (MIC) of an antimicrobial agent against the bacterium being targeted, relative to the antimicrobial agent alone. The "minimum inhibitory concentration" or "MIC" refers to the lowest concentration of an antimicrobial agent that will inhibit the visible growth of a microorganism after overnight (in vitro) incubation. Minimum inhibitory concentrations are important in diagnostic laboratories to confirm resistance of microorganisms to an antimicrobial agent and also to monitor the activity of new antimicrobial agents. The MIC is generally regarded as the most basic laboratory measurement of the activity of an antimicrobial agent against a bacterial organism. Thus, in certain embodiments, the oligomer reduces the minimum inhibitory concentration (MIC) of an antimicrobial agent against the bacterium by at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to the antimicrobial agent alone. In certain embodiments, the oligomer reduces the minimum inhibitory concentration (MIC) of an antimicrobial agent against the bacterium by about or at least about 2, 3, 4, 5, 6, 7, 8, 9, 10, 15, 20, 25, 30, 35, 40, 45, 50, 55, 60, 65, 70, 75, 80, 85, 90, 95, or 100-fold or more (including all integers and ranges in between), relative to the antimicrobial agent alone.

In some embodiments, the antisense oligomer that increases the sensitivity or reduces the MIC is targeted against NDM-1, the bacterium is *Escherichia coli, Acinetobacter baumannii*, or *Klebsiella pneumoniae* that comprises or expresses NDM-1, and the antimicrobial agent is a carbapenem such as meropenem, imipenem, ertapenem, doripenem, panipenem, biapenem, razupenem, tebipenem, lenapenem, or tomopenem.

In particular embodiments, the antisense oligomer that increases the sensitivity or reduces the MIC is targeted against adeA, the bacterium is *Escherichia coli, Acinetobacter baumannii*, or *Klebsiella pneumoniae* that comprises or expresses adeA, and the antimicrobial agent is an aminoglycoside antibiotic (e.g., tobramycin, gentamicin, kanamycin a, amikacin, dibekacin, sisomicin, netilmicin, neomycin B, neomycin C, neomycin E (paromomycin), streptomycin), a tetracycline antibiotic (e.g., tetracycline, chlortetracycline, oxytetracycline, demeclocycline, lymecycline, meclocycline, methacycline, minocycline, rolitetracycline, doxycyline), or a β-lactam antibiotic (e.g., carbapenem, penicillin derivative (penam), cephalosporin (cephem), monobactam).

In particular embodiments, the antisense oligomer that increases the sensitivity or reduces the MIC is targeted against cepI, the bacterium is a *Burkholderia* species, for example, *Burkholderia cepacia* (complex) or a sub-species thereof (e.g., *Burkholderia cenocepacia, Burkholderia multivorans, Burkholderia vietnamiensis, Burkholderia stabilis, Burkholderia anthina, Burkholderia pyrrocinia, Burkholderia dolosa, Burkholderia ambifaria*), which comprises or expresses cepI, and the antimicrobial agent is selected from one or more of ceftazidime, doxycycline, piperacillin, meropenem, chloramphenicol, and co-trimoxazole (trimethoprim/sulfamethoxazole).

In particular embodiments, the antisense oligomer that increases the sensitivity or reduces the MIC is targeted against suhB, the bacterium is a *Burkholderia* species, for example, *Burkholderia cepacia* (complex) or a sub-species thereof (e.g., *Burkholderia cenocepacia, Burkholderia multivorans, Burkholderia vietnamiensis, Burkholderia stabilis, Burkholderia anthina, Burkholderia pyrrocinia, Burkholderia dolosa, Burkholderia ambifaria*), which comprises or expresses suhB, and the antimicrobial agent is selected from one or more of ceftazidime, doxycycline, piperacillin, meropenem, chloramphenicol, and co-trimoxazole (trimethoprim/sulfamethoxazole).

In particular embodiments, the antisense oligomer that increases the sensitivity or reduces the MIC is targeted against acpP, the bacterium is a *Burkholderia* species, for example, *Burkholderia cepacia* (complex) or a sub-species thereof (e.g., *Burkholderia cenocepacia, Burkholderia multivorans, Burkholderia vietnamiensis, Burkholderia stabilis, Burkholderia anthina, Burkholderia pyrrocinia, Burkholderia dolosa, Burkholderia ambifaria*), which comprises or expresses acpP, and the antimicrobial agent is selected from one or more of ceftazidime, doxycycline, piperacillin, minocycline, meropenem, chloramphenicol, and co-trimoxazole (trimethoprim/sulfamethoxazole).

IV. Treatment Monitoring Methods

The efficacy of a given therapeutic regimen involving the methods described herein may be monitored, for example, by general indicators of bacterial infection, such as complete blood count (CBC), nucleic acid detection methods, immunodiagnostic tests, or bacterial culture.

In some aspects, identification and monitoring of bacterial infection involves one or more of (1) nucleic acid detection methods, (2) serological detection methods, i.e., conventional immunoassay, (3) culture methods, and (4) biochemical methods. Such methods may be qualitative or quantitative.

Nucleic acid probes may be designed based on publicly available bacterial nucleic acid sequences, and used to detect target genes or metabolites (i.e., toxins) indicative of bacterial infection, which may be specific to a particular bacterial type, e.g., a particular species or strain, or common to more than one species or type of bacteria (i.e., Gram positive or Gram negative bacteria). Nucleic amplification tests (e.g., PCR) may also be used in such detection methods.

Serological identification may be accomplished using a bacterial sample or culture isolated from a biological specimen, e.g., stool, urine, cerebrospinal fluid, blood, etc. Immunoassay for the detection of bacteria is generally carried out by methods routinely employed by those of skill in the art, e.g., ELISA or Western blot. In addition, monoclonal antibodies specific to particular bacterial strains or species are often commercially available.

Culture methods may be used to isolate and identify particular types of bacteria, by employing techniques including, but not limited to, aerobic versus anaerobic culture, growth and morphology under various culture conditions. Exemplary biochemical tests include Gram stain (Gram, 1884; Gram positive bacteria stain dark blue, and Gram negative stain red), enzymatic analyses, and phage typing.

It will be understood that the exact nature of such diagnostic, and quantitative tests as well as other physiological factors indicative of bacterial infection will vary dependent upon the bacterial target, the condition being treated and whether the treatment is prophylactic or therapeutic.

In cases where the subject has been diagnosed as having a particular type of bacterial infection, the status of the bacterial infection is also monitored using diagnostic techniques typically used by those of skill in the art to monitor the particular type of bacterial infection under treatment.

The PMO or PPMO treatment regimen may be adjusted (dose, frequency, route, etc.), as indicated, based on the results of immunoassays, other biochemical tests and physiological examination of the subject under treatment.

From the foregoing, it will be appreciated how various objects and features of the disclosure are met. The method provides an improvement in therapy against bacterial infection, for example, multi-drug resistant (MDR) bacteria and/or biofilm-forming bacteria, using anti-virulence antisense oligomers to achieve enhanced cell uptake and anti-bacterial action. As a result, drug therapy is more effective and less expensive, both in terms of cost and amount of compound required.

One exemplary of the disclosure is that compounds effective against virtually any pathogenic bacterial can be readily designed and tested, e.g., for rapid response against new drug-resistant strains.

The following examples are intended to illustrate but not to limit the disclosure. Each of the patent and non-patent references referred to herein is incorporated by reference in its entirety.

EXAMPLES

Example 1

Activity of PPMOs Targeted Against adeA

A cell-penetrating peptide-conjugated phosphorodiamidate morpholino oligomer (PPMOs) targeted against the resistance-nodulation-cell division (RND)-type multidrug efflux pump subunit adeA (adeA) was prepared and tested for the ability to reduce the minimum inhibitory concentration (MIC) of various antibiotics against adeA-expressing *Acinetobacter baumanii*.

The adeA-targeted PPMO has the following sequence: ATACTGTCCAA (SEQ ID NO: 15; PPMO#5). The PPMO was conjugated at its 3'-end to the C-terminal β-alanine residue of (RXR)₄XB (SEQ ID NO: 40).

The MIC of the antibiotics gentamicin, tobramycin, and tetracycline was measured using the microdilution method of the Clinical Laboratory Standards Institute in a 96-well microtiter plate format. Multiple, identical dilution series of each antibiotic were included on each microtiter plate. In each dilution series of antibiotic, a fixed amount of PPMO was added. Each dilution series of antibiotic included a different concentration of PPMO.

Figure 2:
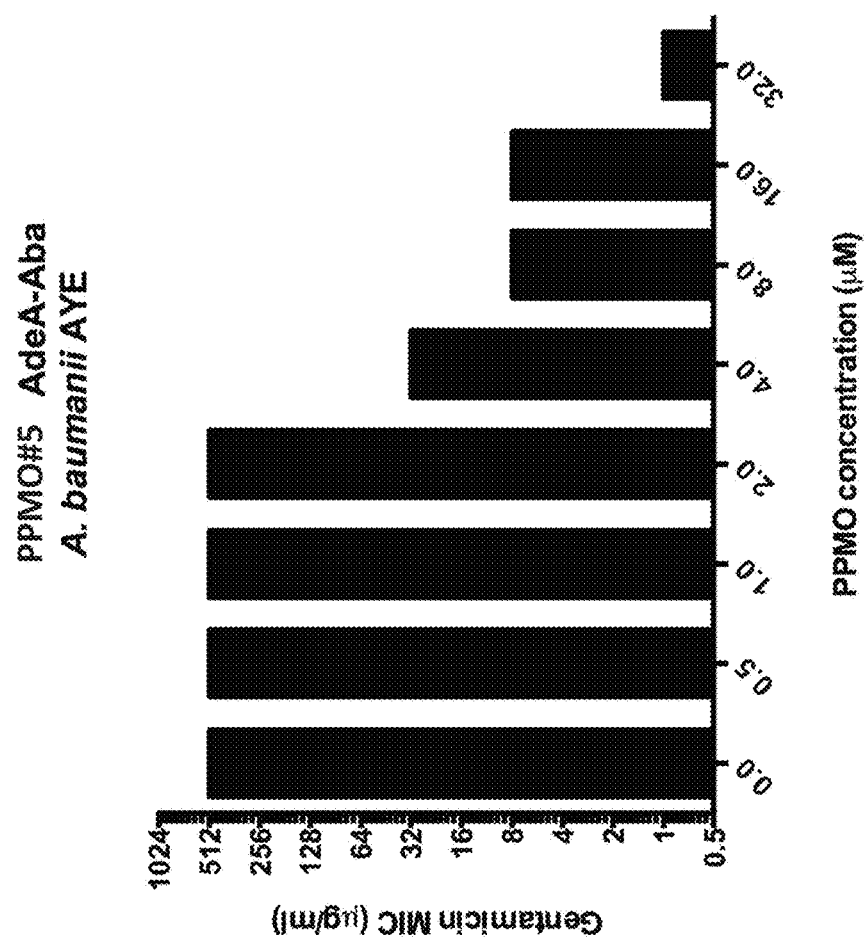
FIG. 2 shows that treatment of AdeA (efflux pump)-expressing *Acinetobacter baumanii* with a PPMO targeted against adeA significantly reduced the MIC of the aminoglycoside antibiotic gentamicin.
Figure 3:
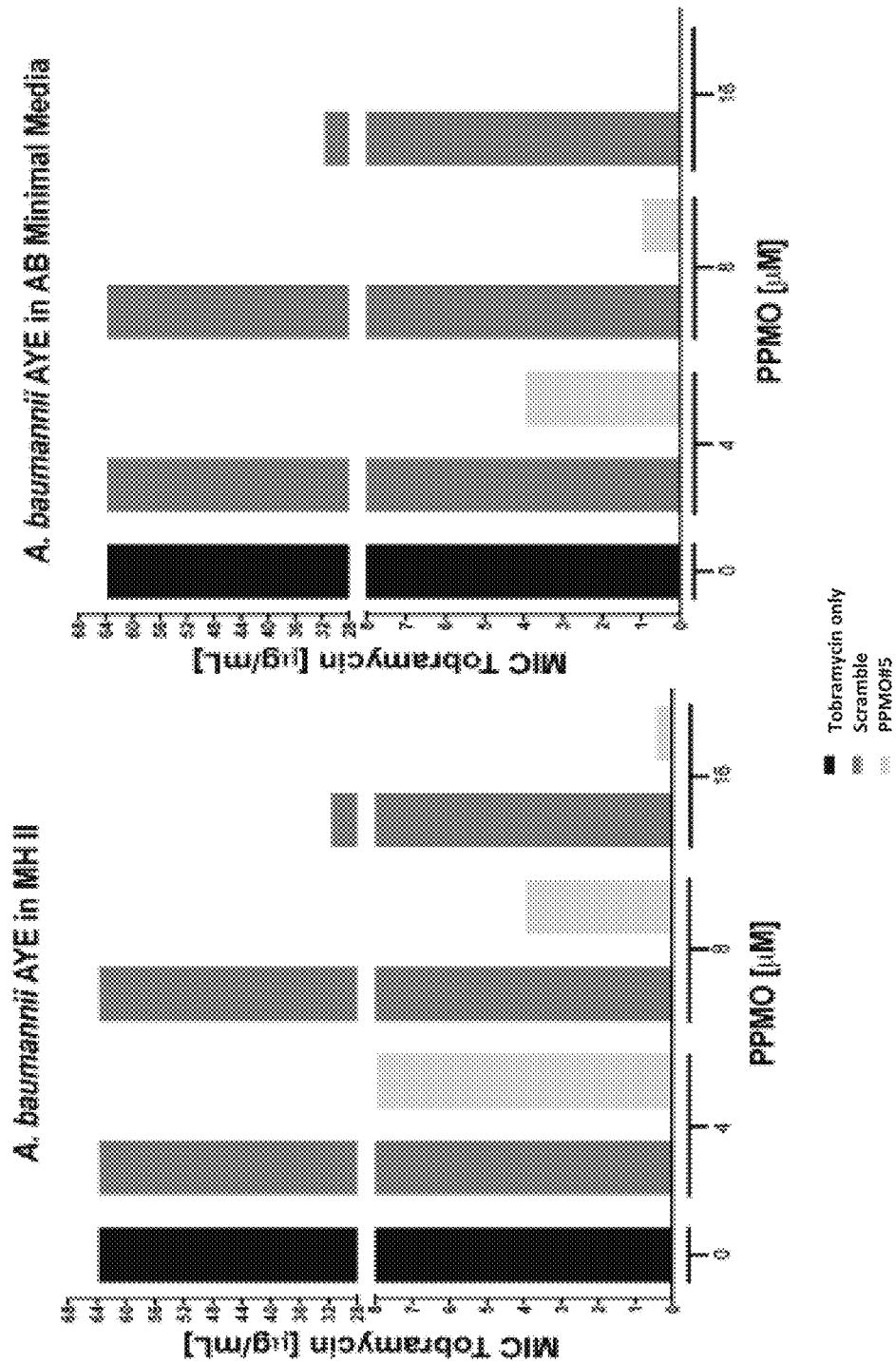
FIG. 3 shows that treatment of AdeA-expressing *Acinetobacter baumanii* with a PPMO targeted against adeA significantly reduced the MIC of the aminoglycoside antibiotic tobramycin.
Figure 4:
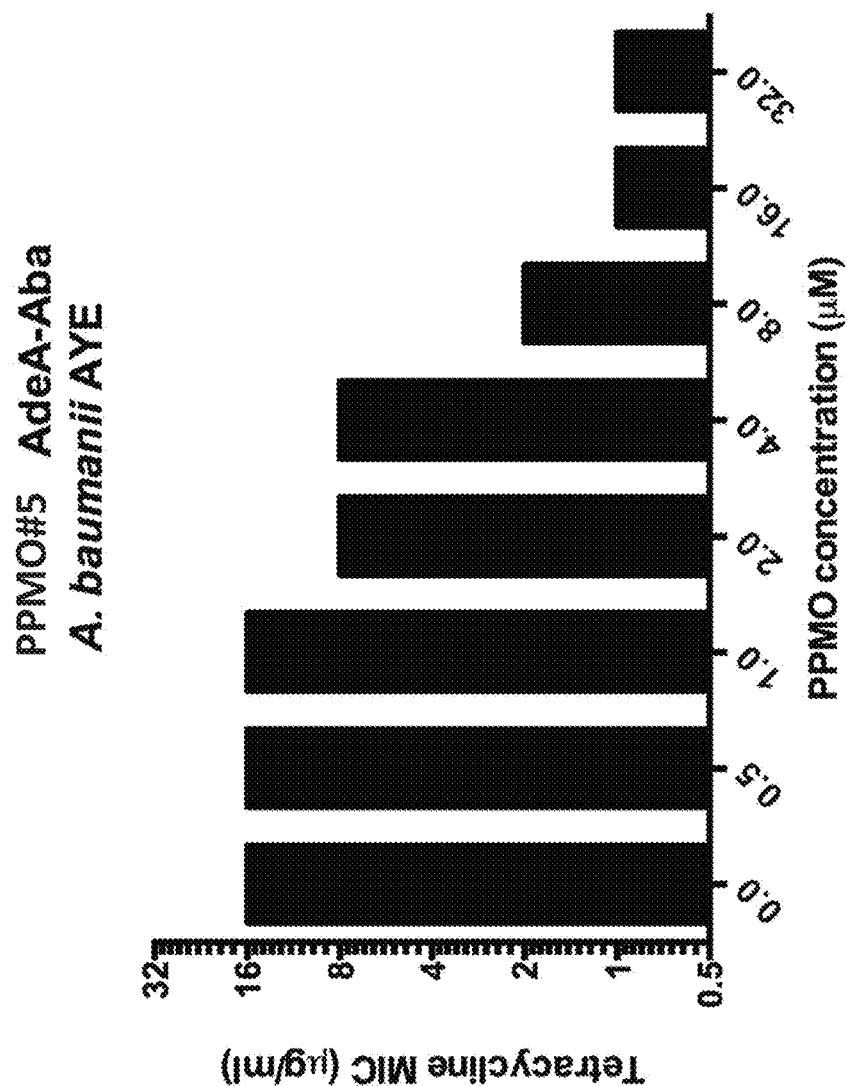
FIG. 4 shows that treatment of AdeA-expressing *Acinetobacter baumanii* with a PPMO targeted against adeA significantly reduced the MIC of tetracycline.

The results are shown in FIGS. 2-4. These figures show that treatment of adeA (efflux pump)-expressing *Acinetobacter baumanii* with the adeA-targeted PPMO significantly reduced the MIC of gentamicin (FIG. 2), tobramycin (FIG. 3), and tetracycline (FIG. 4), each in a concentration dependent manner.

Example 2

Activity of PPMOs Targeted Against NDM-1

Peptide-conjugated phosphorodiamidate morpholino oligomers (PPMOs) targeted against the New Delhi metallo-beta-lactamase (NDM-1) were prepared and tested for the ability to reduce the minimum inhibitory concentration (MIC) of meropenem against NDM-1-expressing *Acinetobacter baumanii* and *E. coli*.

The NDM-1 targeted PPMOs have the following sequences: TCAAGTTTTCC (SEQ ID NO: 11; PPMO#1); TCCTTTTATTC (SEQ ID NO: 12; PPMO#2); CCATCAAGTTT (SEQ ID NO: 13; PPMO#3); and GGCAATTCCAT (SEQ ID NO: 14; PPMO#4). Each of the PPMOs was conjugated at its 3'-end to the C-terminal β-alanine residue of (RXR)₄XB (SEQ ID NO: 40).

The MIC of meropenem was measured using the microdilution method of the Clinical Laboratory Standards Institute in a 96-well microtiter plate format. Multiple, identical dilution series of meropenem were included on each microtiter plate. In each dilution series of meropenem, a fixed amount of PPMO was added. Each dilution series of meropenem included a different concentration of PPMO.

Figure 5A:
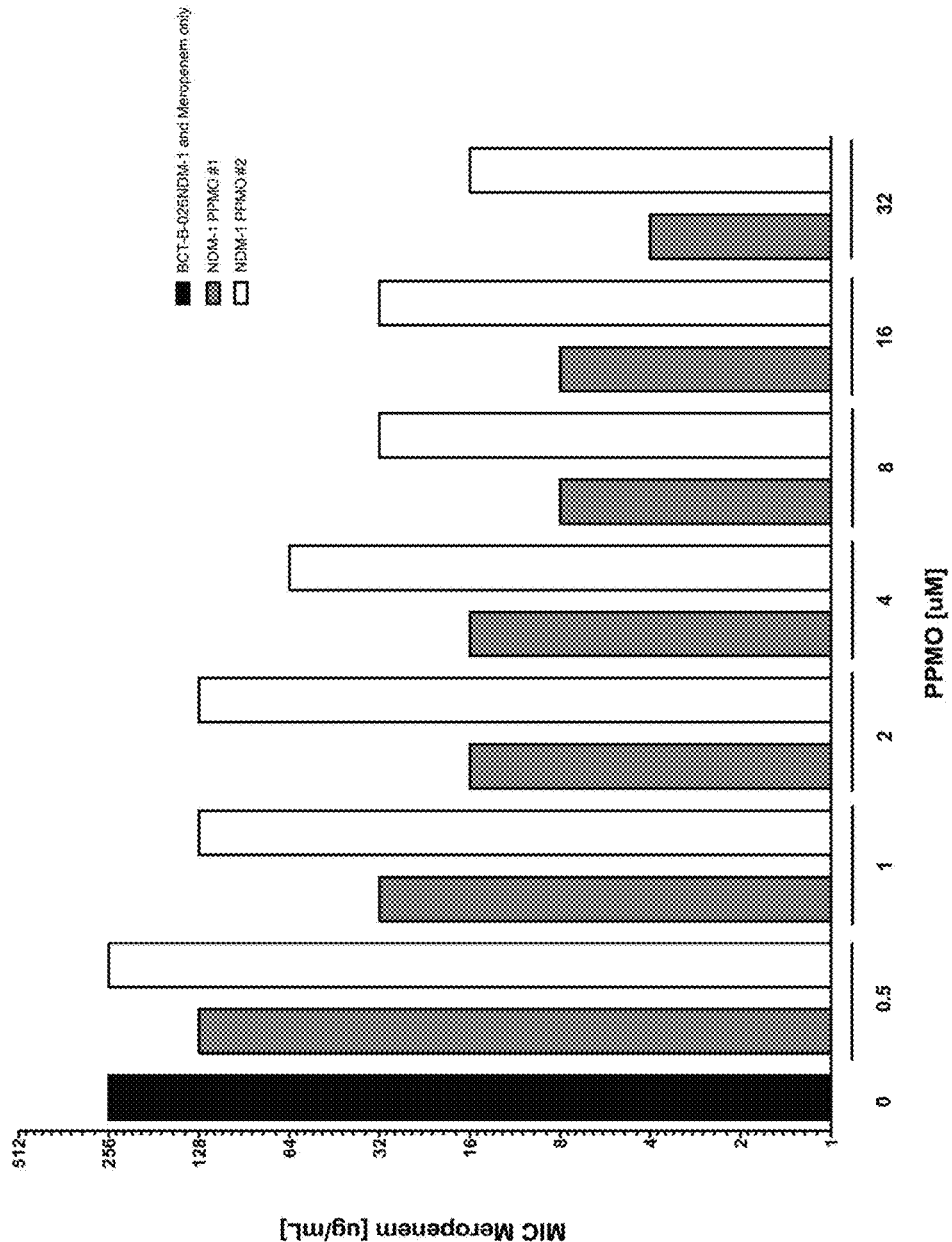
FIG. 5A shows that treatment of NDM-1-expressing *Acinetobacter baumanii* with a PPMO targeted against NDM-1 significantly reduced the MIC of the carbapenem antibiotic meropenem.
Figure 5B:
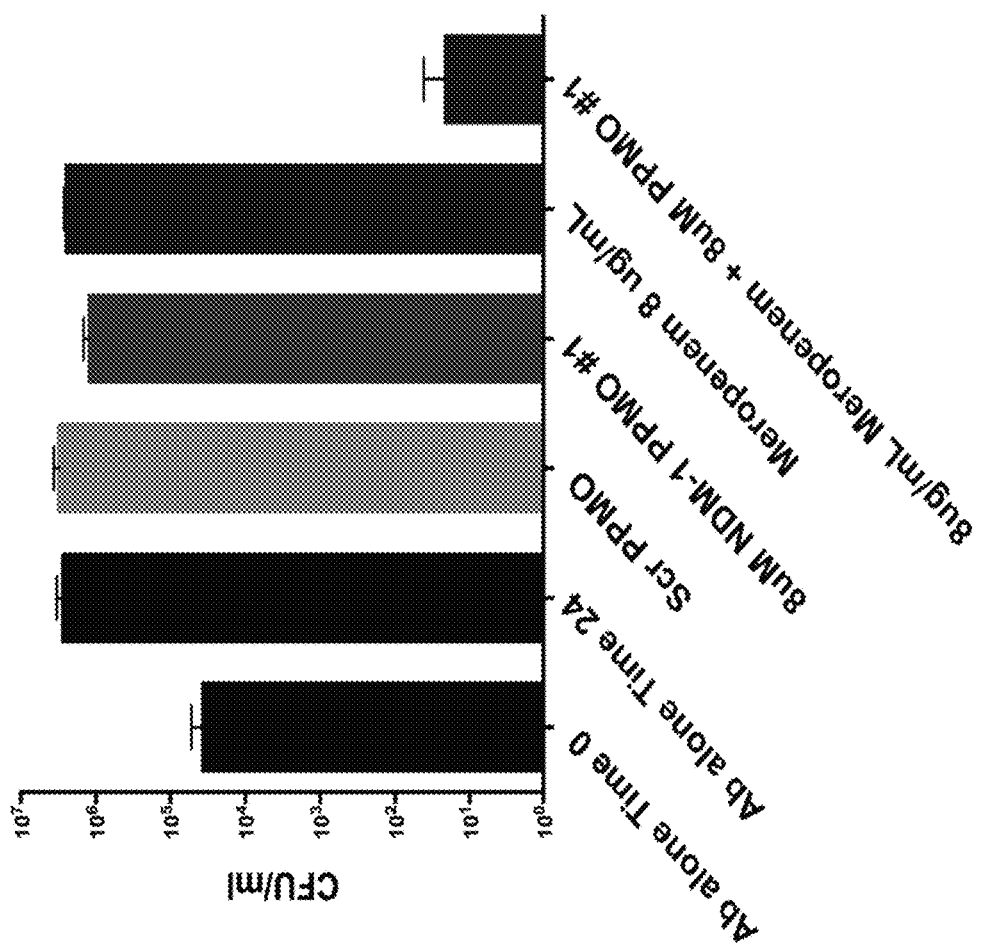
FIG. 5B shows that the NDM-1 targeted PPMO and meropenem synergistically reduced the number of colony-forming units (CFUs) of NDM-1-expressing *Acinetobacter baumanii*.
Figure 6:
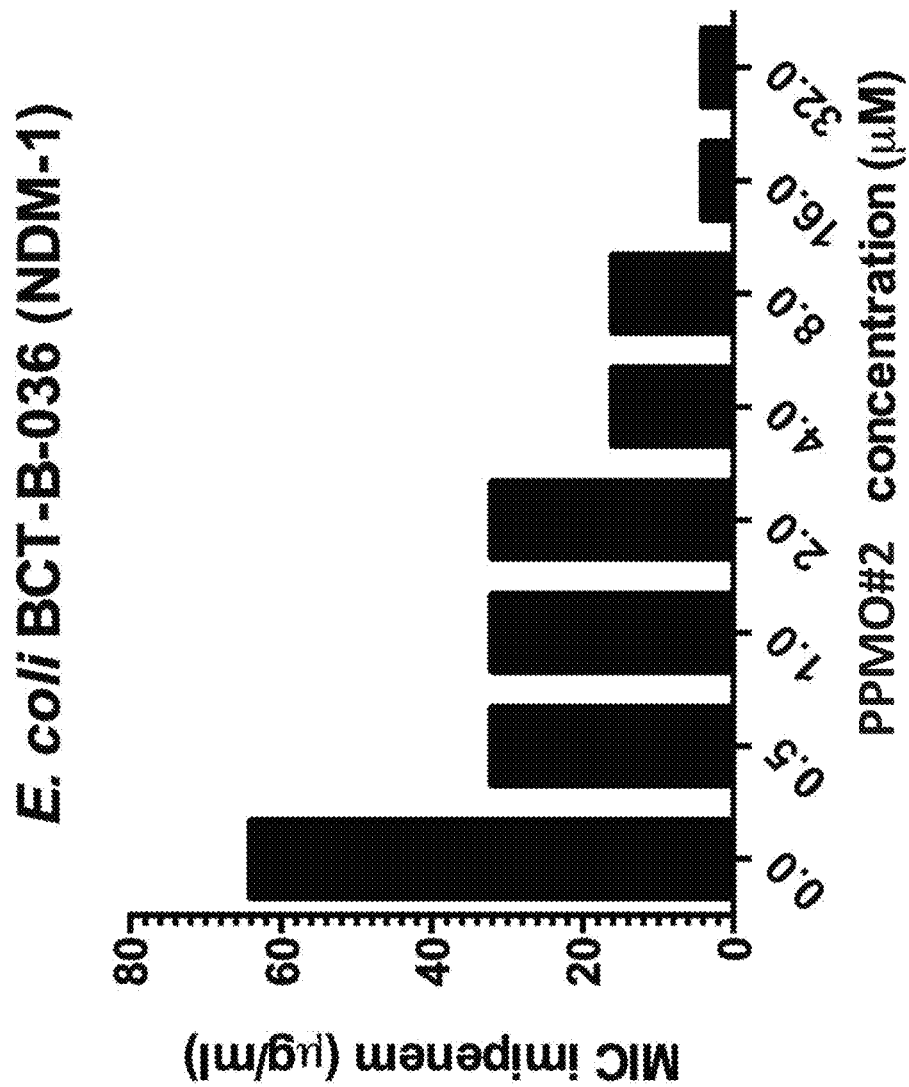
FIG. 6 shows that treatment of NDM-1-expressing *Escherichia coli* with a PPMO targeted against NDM-1 significantly reduced the MIC of the carbapenem antibiotic meropenem.

As shown in FIGS. 5A-5B and 6, NDM-1-targeted PPMOs reduced the MIC of meropenem from about 8 to 32-fold, depending on the bacterium. These figures show that treatment of NDM-1-expressing *Acinetobacter baumanii* (FIG. 5A) and NDM-1-expressing *E. coli* (FIG. 6) with NDM-1-targeted PPMOs significantly reduced the MIC of meropenem in a concentration dependent manner. FIG. 5B shows that the NDM-1 targeted PPMO and meropenem synergistically reduced the number of colony-forming units (CFUs) of NDM-1-expressing *Acinetobacter baumanii*. Meropenemase enzymatic activity in the periplasm of PPMO-treated cells was thus observed to be inversely proportional to the amount of PPMO added.

Similar effects were shown for *Klebsiella pneuomoniae*; at a concentration of 8 µM, the most effective NDM-1-targeted PPMO reduced the MIC of meropenem from about 64 µM to about 4 µM (data not shown).

Thus, the NDM-1-targeted PPMOs silenced expression of NDM-1 and reduced the MIC of meropenem to susceptible concentrations in three multidrug-resistant pathogens.

Example 3

Activity of PPMOs Targeted Against Biofilm and Acyl Carrier Protein Genes

Peptide-conjugated phosphorodiamidate morpholino oligomers (PPMOs) targeted against the biofilm formation genes suhB and cepI and the acyl carrier protein acpP gene were prepared and tested for the ability to reduce biofilm formation and to break down established biofilm in *Burkholderia cenocepacia* J2315.

The suhB-targeted PPMOs have the following sequences: ATGCATGAGCC (SEQ ID NO: 23; PPMO#13); and GGATGCATGAG (SEQ ID NO: 24; PPMO#14).

The cepI-targeted PPMOs have the following sequences: AAGGTCTGCAT (SEQ ID NO: 16; PPMO#6); TCGGATCTGTG (SEQ ID NO: 17; PPMO#7); CATGGATGTCC (SEQ ID NO: 18; PPMO#8); CGTGAACGAAG (SEQ ID NO: 19; PPMO#9); CGTGTGGCAAC (SEQ ID NO: 20; PPMO#10); GCCCGAGATCC (SEQ ID NO: 21; PPMO#11); and CTTTCGTTCGC (SEQ ID NO: 22; PPMO#12).

Each of the suhB-targeted and cepI-targeted PPMOs was conjugated at its 3'-end to the C-terminal β-alanine residue of (RFF)₃RXB (SEQ ID NO: 41).

The acpP-targeted PPMOs have the sequences and peptide conjugations as shown in Table 3C (PPMO #s 15-29).

Figure 8A:
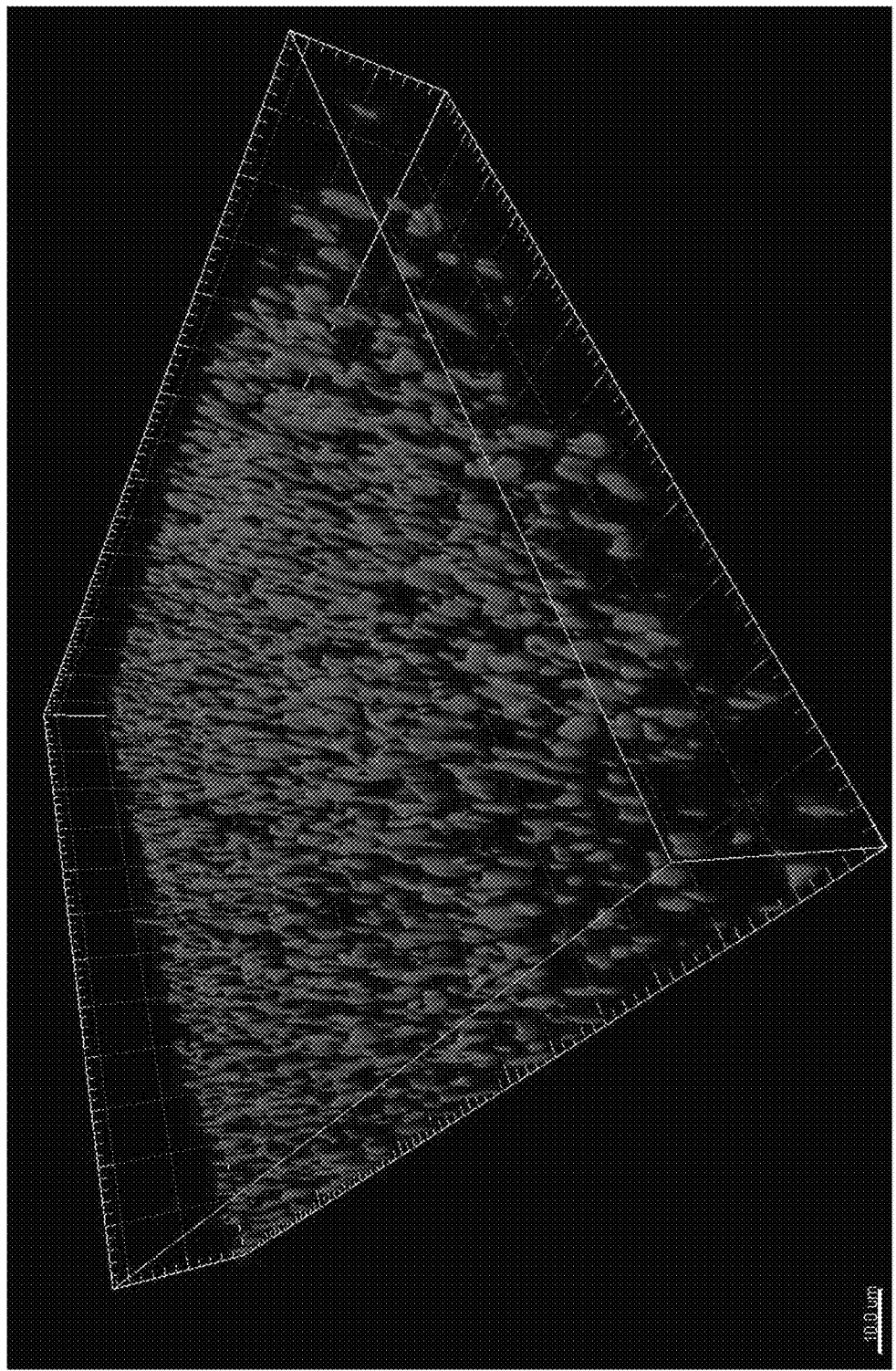
FIGS. 8A-8C visually demonstrate the reduction of biofilm formation on MBEC pegs using fluorescent-expressing *Burkholderia* and utilizing confocal microscopy.
Figure 8B:
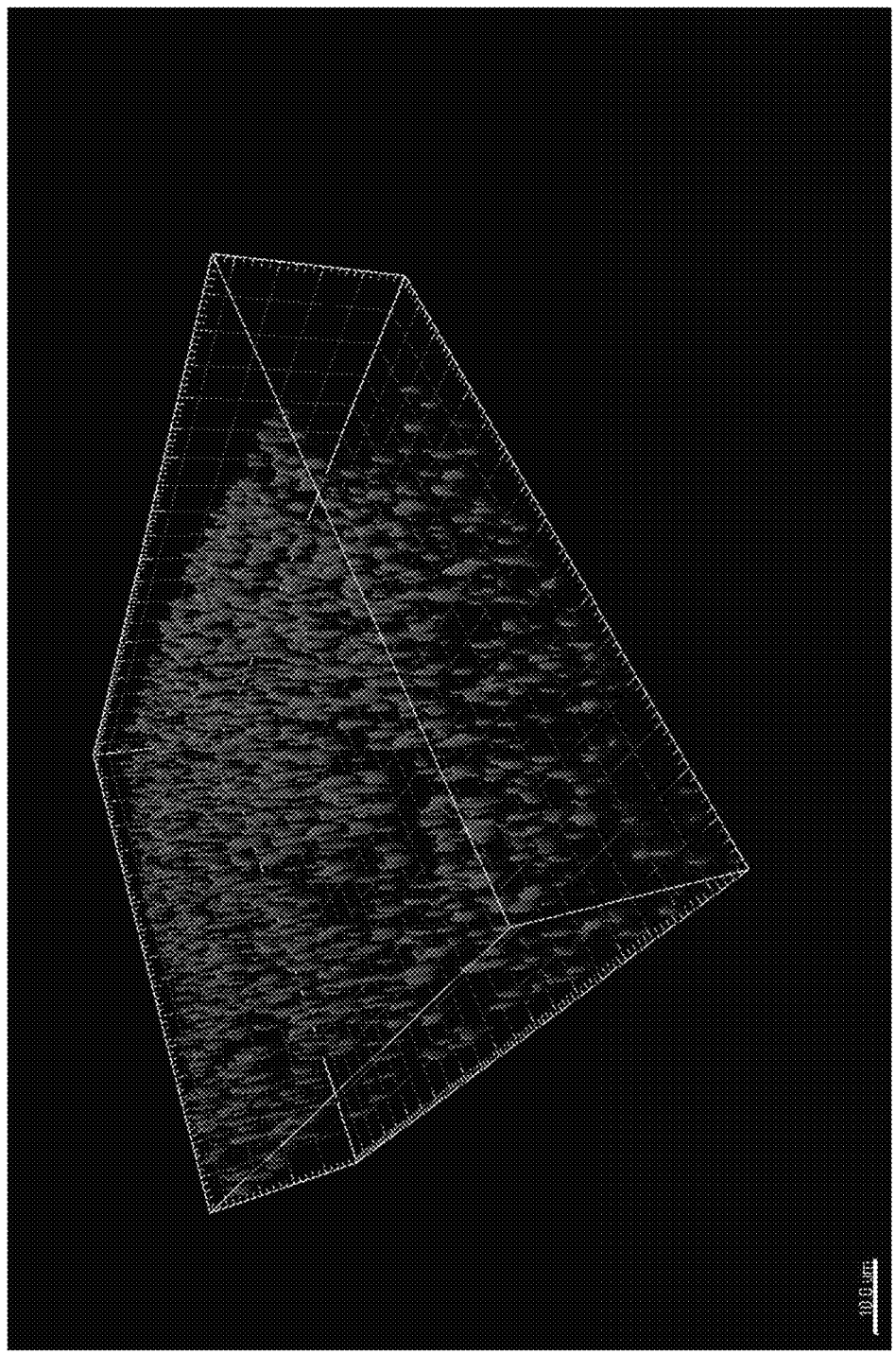
Figure 8C:
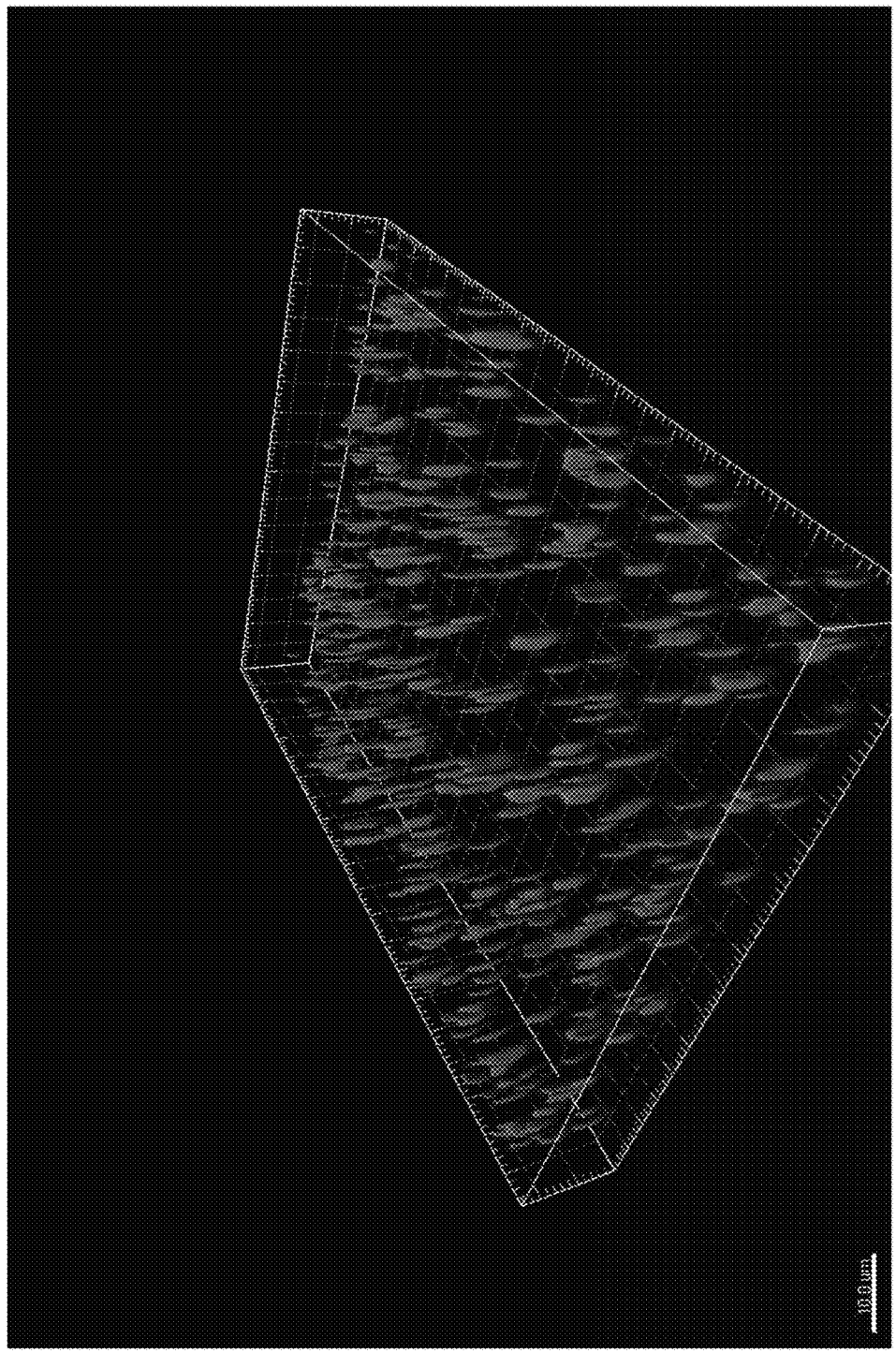

Biofilms were formed in 150 µl cultures of *Burkholderia cenocepacia* J2315, using 96-well polystyrene microtiter plates. To test the ability of PPMOs to reduce biofilm formation, PPMOs (1-10 µM) were added to bacterial cultures prior to biofilm formation and incubated with bacteria for 48 hours. To test the ability of PPMOs to reduce established biofilms, bacterial cultures were grown for 48 hours and allowed to form biofilms prior to addition of PPMOs (1-10 µM), and then incubated for an additional 48 hours in the presence of PPMOs. For analysis, the liquid cultures were removed and the biofilms that adhered to the microtiter plate were stained with crystal violet. The amount of crystal violet stain in the biofilm was measured, and found to be proportional to the amount of biofilm. Confocal laser scanning microscopy (CLSM) and dsRed expressing *Burkholderia cenocepacia* J2315 were used to visualize biofilm structural changes (see FIGS. 8A-8C).

Figure 7A:
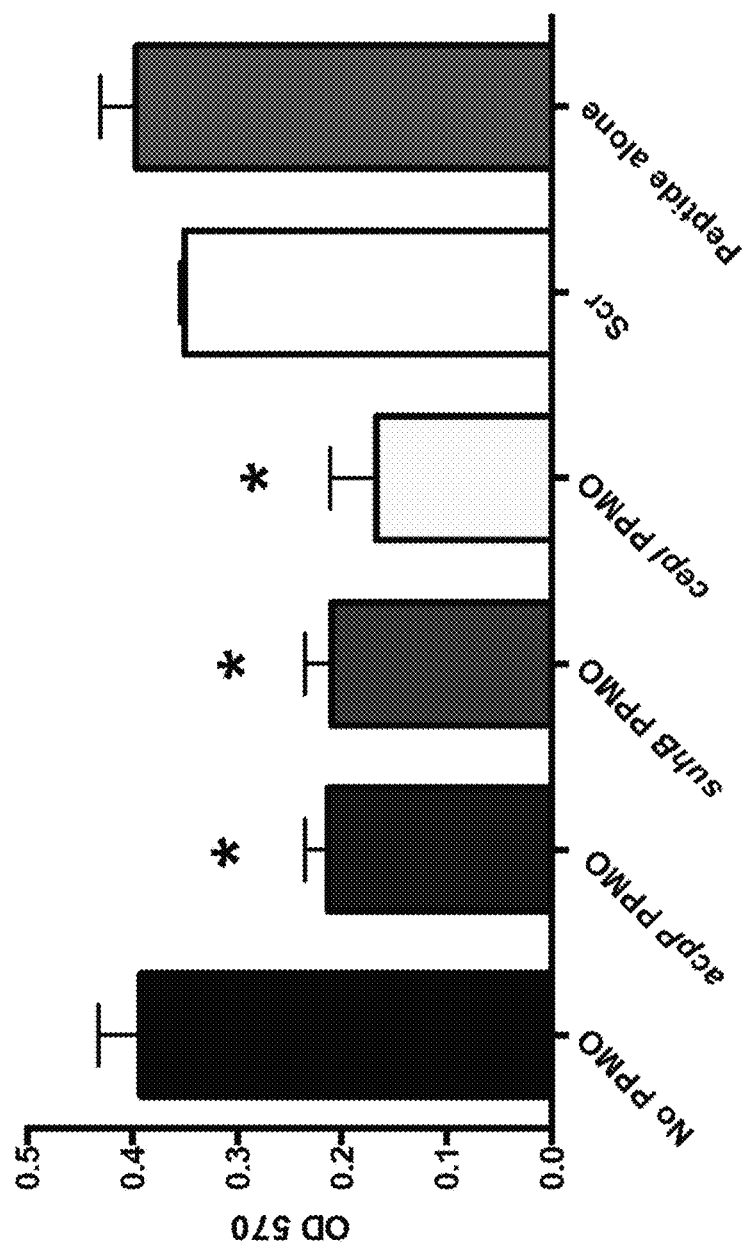
FIGS. 7A-7B show that treatment of biofilm-forming *Burkholderia* with PPMOs targeted against acpP, suhB or cepI not only disrupted the formation of biofilm (7A; PPMOs were added prior to biofilm formation and incubated for 48 hours) but also broke down established biofilms (7B; biofilm was grown for 48 hours prior to 48-hour incubation with PPMOs).
Figure 7B:
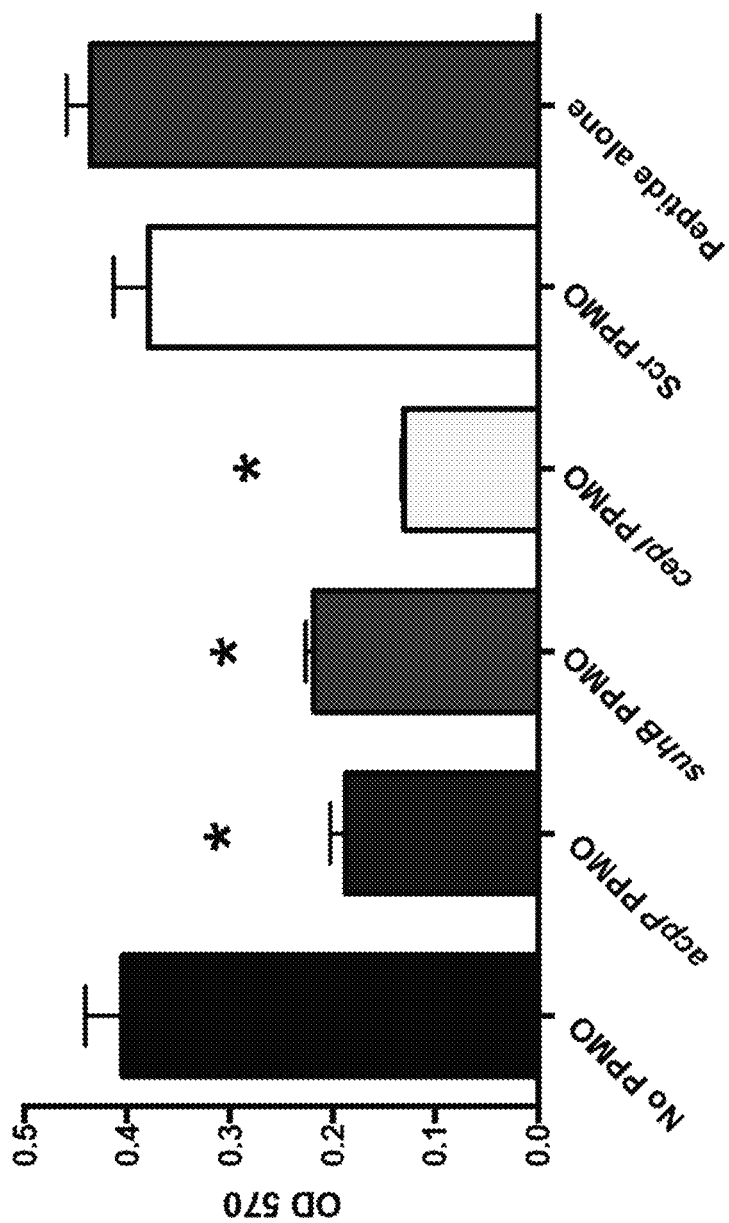

As shown in FIGS. 7A-7B, treatment of biofilm-forming *Burkholderia* with PPMOs targeted against acpP, suhB or cepI not only disrupted the formation of biofilm (7A; PPMOs were added prior to biofilm formation and incubated for 48 hours) but also broke down established biofilms (7B; biofilm was grown for 48 hours prior to 48-hour incubation with PPMOs). A 10 µM concentration of acpP-targeted PPMO reduced biofilm formation by about 45% and reduced existing biofilm by about 50%. A 10 µM concentration of cepI-targeted PPMO reduced biofilm formation by about 52% and reduced existing biofilm by about 65%. A 10 µM concentration of suhB-targeted PPMO reduced biofilm formation by about 40% and reduced existing biofilm by about 42%. Thus, when biofilms were visualized with CLSM there was a dramatic reduction in biofilm formation in the presence of cepI-targeted and suhB-targeted PPMOs.

Example 4

PPMOs Act Synergistically with Antibiotics to Reduce Bacterial Growth in Established Biofilms PPMOs targeted against the biofilm formation gene cepI were prepared and tested for the ability to reduce bacterial growth in established biofilms in combination with the aminoglycoside antibiotic Tobramycin in *Burkholderia cenocepacia* J2315.

The cepI-targeted PPMOs have the following sequences: PPMO#s 6-12 in Table 3B.

Each of the PPMOs was conjugated at the 3' terminus with (RFF)$_3$RXB (SEQ ID NO: 41).

To test the ability of cepI PPMOs and Tobramycin to reduce bacterial growth in established biofilms, bacterial cultures were grown for 48 hours and allowed to form biofilms prior to addition of PPMOs or PPMO and Tobramycin, and then incubated for an additional 48 hours in the presence of no PPMOs, scrambled control PPMO, scrambled control PPMO with Tobramycin at either 64 μg/mL or 128 μg/mL, cepI PPMO, and cepI PPMO with Tobramycin at either 64 μg/mL or 128 μg/mL. Bacterial growth was measured as CFU/mL.

Figure 9:
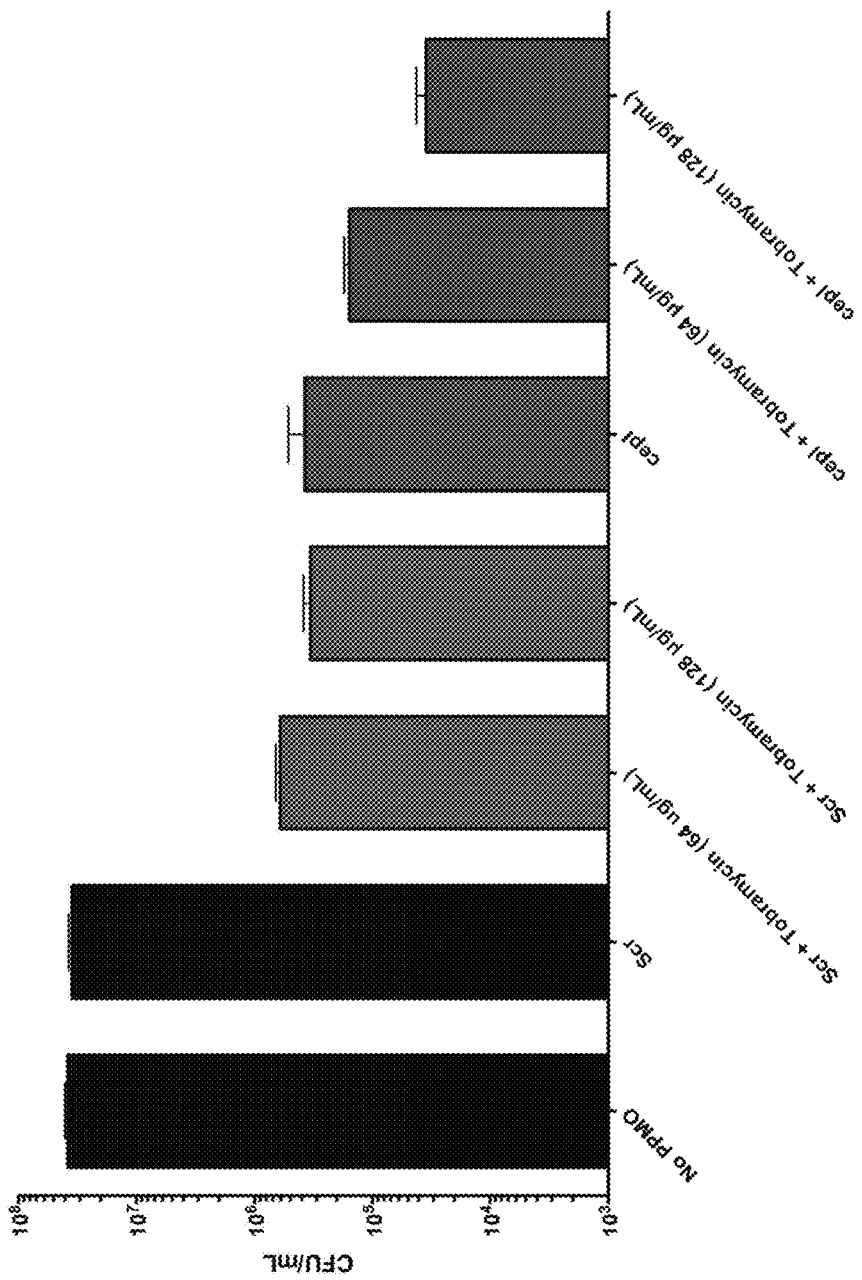
FIG. 9 shows that cepI PPMO and the aminoglycoside antibiotic Tobramycin are synergistic in reducing biofilm organism burden.

As shown in FIG. 9, cepI PPMO alone or scrambled PPMO with Tobramycin was able to inhibit bacterial growth significantly about 2 logs compared to the untreated biofilm. cepI PPMO in combination with Tobramycin, however, was further able to significantly inhibit bacterial growth on the established biofilm, and at the higher concentration of Tobramycin (128 μg/mL), was able to reduce the bacterial CFU/mL by another log compared to cepI PPMO alone.

Example 5

PPMOs Inhibit Members of the Bcc

Figure 10:
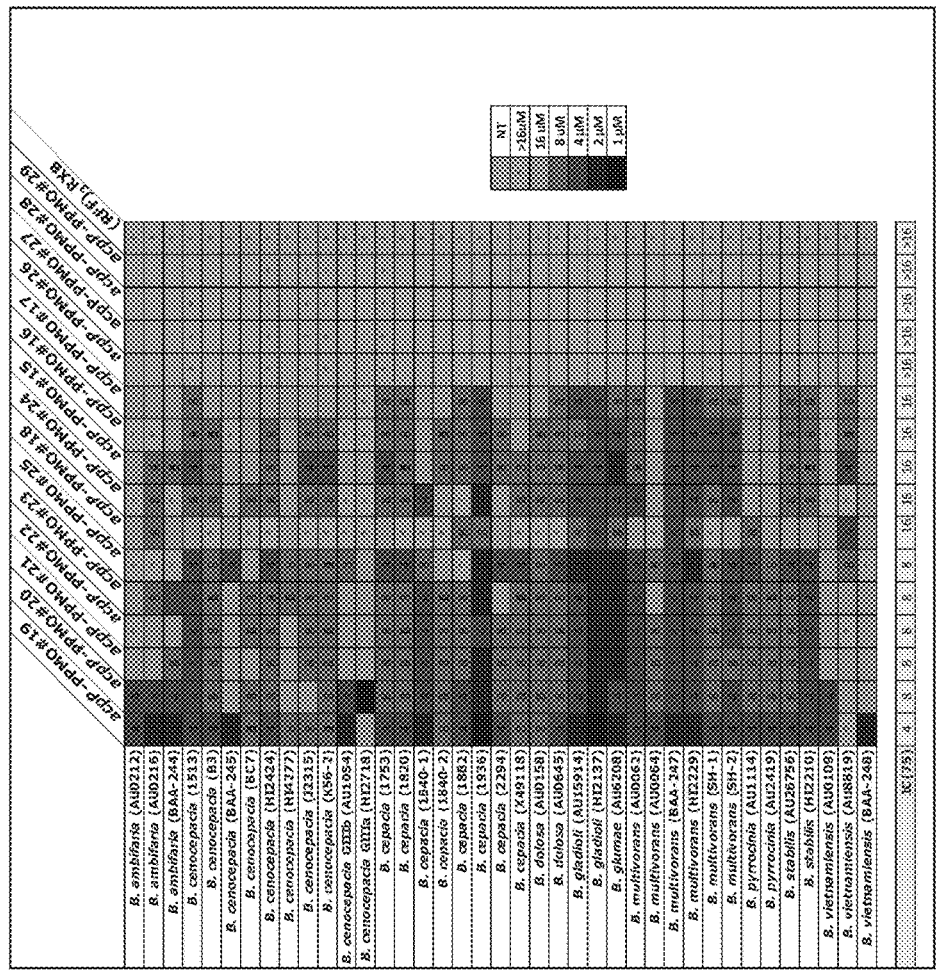
FIG. 10 shows a heat map of the minimal inhibitory concentration (MIC) values for various PPMOs including ones listed in Table 2C. The PPMOs were tested against a panel of 39 Bcc clinical isolates with varying levels of antibiotic resistance.

A variety of Bcc isolates were tested, including clinical isolates obtained from various body sites with varying levels of antibiotic resistance. The strain bank included 39 isolates that comprised the most frequently encountered species that have been reported to cause human disease. As shown in FIG. 10, 6 PPMOs (PPMO#s 19-23 and 25) achieved IC$_{73}$ values of 8 μM or less. All 6 of these PPMOs targeted AcpP (an acyl carrier protein associated with fatty acid biosynthesis). Differences in the 6 PPMOs related to alternative positioning sites on the target mRNA. The most potent PPMO (PPMO#19) had an IC$_{73}$ of 4 μM. acpP PPMO targeting sequences are listed in Table 3C.

Example 6

PPMOs are Bactericidal in Bcc

Figure 11:
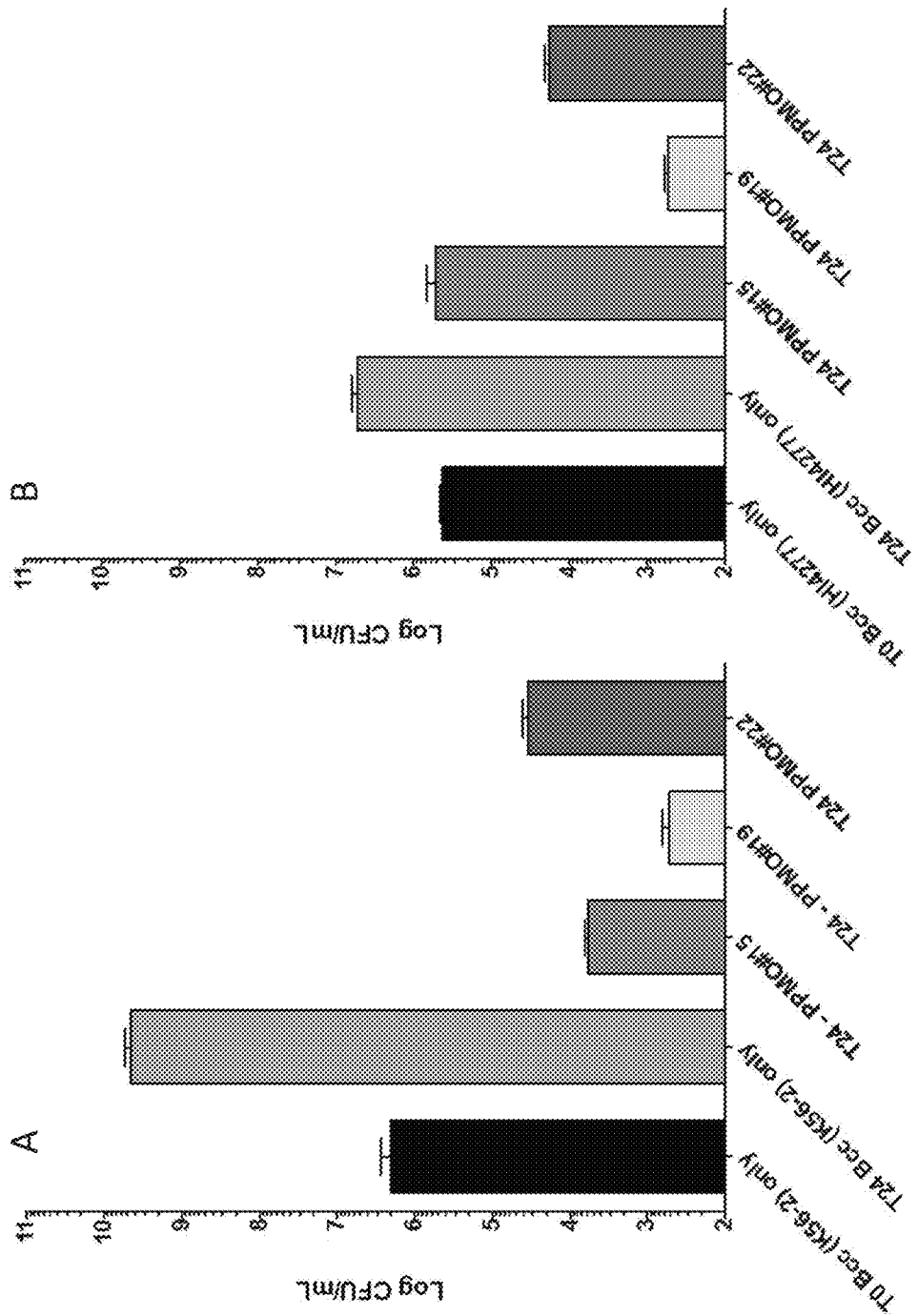
FIG. 11 shows that PPMOs are bactericidal in Bcc. Two different isolates of *B. cenocepacia* were incubated for 24 hours in the presence or absence of different acpP PPMOs. All three acpP PPMOs caused a significant reduction of growth in the clinical CF isolate *B. cenocepacia* K56-2 (Panel A) and this effect was also seen for the pan-resistant strain *B. cenocepacia* HI4277 (Panel B).

Many members of the Bcc are intrinsically antibiotic resistant making treatment difficult. *B. cenocepacia* is one of the most common species encountered by cystic fibrosis (CF) patients. Two different isolates of *B. cenocepacia* were incubated for 24 hours in the presence or absence of different acpP PPMOs (FIG. 11).

The acpP-targeted PPMOs have the following sequences: GTCCATTACCC (PPMO#15; SEQ ID NO: 25); CCATTACCCCT (PPMO#19; SEQ ID NO: 27); and TTGTCCATTAC (PPMO#22; SEQ ID NO: 30).

Each of the PPMOs was conjugated at its 5'-end to the C-terminal β-alanine residue of (RFF)$_3$RXB (SEQ ID NO: 41).

In *B. cenocepacia* K56-2 (a genome-sequenced clinical CF isolate; Panel A) all three PPMOs caused a significant reduction of growth with one PPMO (PPMO#19; SEQ ID NO: 27; 16 μM) causing >3-log reduction of growth compared to the starting inoculum, a strong bactericidal effect. Importantly, this effect was seen even in pan-resistant strains of *B. cenocepacia* (HI4277, a pan-resistant outbreak isolate from CF patients; FIG. 11, Panel B). Even though this strain demonstrated resistance to all traditional antibiotics, PPMO#19 was bactericidal. The MIC of PPMO#19 was 8 μM in HI4277 (FIG. 10), illustrating that PPMOs' ability to inhibit growth is not dependent on the underlying level of antibiotic resistance in any particular strain, an important finding with positive implications for this approach.

Example 7

PPMOs Inhibit Bcc Growth in Sputum

Chronic infections in the CF patient usually manifest in the lung. In addition, members of the Bcc and *P. aeruginosa* are known to form biofilms. These biofilms and the thick sputum formed by CF patients makes treatment with antibiotics particularly difficult and these pathogens become virtually impossible to completely eradicate from the lung environment.

Figure 12:
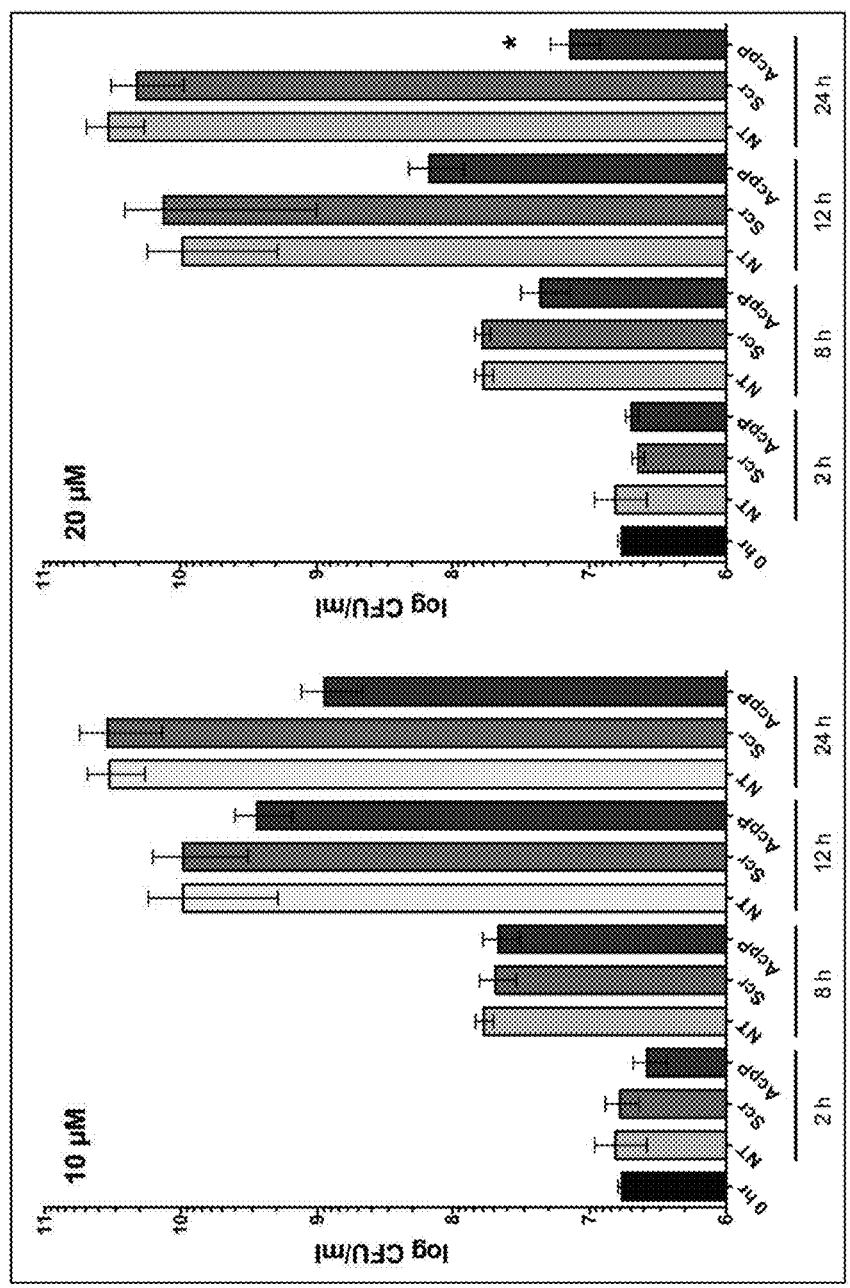
FIG. 12 shows that acpP PPMO inhibits Bcc growth in artificial CF sputum. *B. cenocepacia* K56-2 was incubated alone or in the presence of either a scrambled sequence (Scr) placebo PPMO or acpP PPMO (PPMO#15, Table 2C) at 10 µM or 20 µM concentration. Media or PPMO was dosed at 2, 8 and 12 hours. Samples were plated at 24 hours and CFU/ml was determined.

PPMOs were tested to determine whether they retained their activity in sputum. Using a well-described method for making "artificial CF sputum," experiments were conducted to see whether a PPMO could reduce the burden of Bcc in this environment (FIG. 12). *B. cenocepacia* K56-2 was incubated alone or in the presence of either a scrambled-sequence (Scr) placebo PPMO or acpP PPMO (PPMO#15). The acpP-targeted PPMO has the following sequence: GTCCATTACCC (PPMO#15; SEQ ID NO: 25). The PPMO was conjugated at its 5' end to the C-terminal β-alanine residue of (RFF)$_3$RXB (SEQ ID NO: 41). Media or PPMO was dosed at 2, 8 and 12 hours. Samples were plated at 24 hours and CFU/ml was determined. The acpP PPMO was able to reduce the organism burden (both at 10 and 20 μM dosing). At 10 μM dosing, there was an approximately 2-log reduction in CFU/ml by 24-hours compared to no treatment control. At 20 μM dosing, there was a >3-log reduction seen. This reduction was apparent as early as 8 hours in the 20 μM group and 12 hours in the 10 μM group. These experiments indicate that PPMOs remain active even in the thick viscous sputum that is seen in CF patients. This is the first time that activity of PPMOs has been tested in sputum.

Example 8 acpP PPMOs can Both Prevent Biofilm Formation and Deconstruct Existing Biofilms

Figure 13:
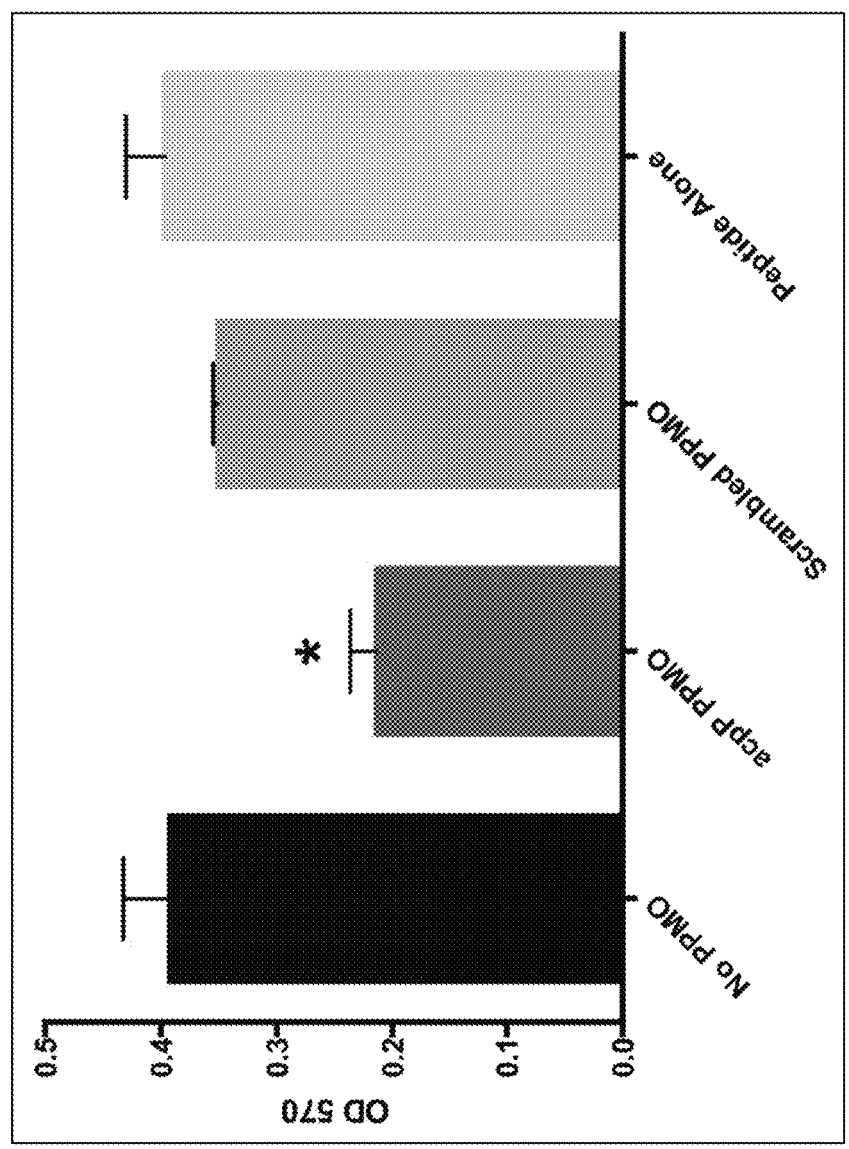
FIG. 13 shows that acpP PPMO prevents biofilm formation in *B. cenocepacia* J2315. *B. cenocepacia* J2315 was grown utilizing MBEC biofilm assay plates for 48 hours in the presence of either acpP PPMO (10 µM), scrambled PPMO (10 µM), peptide or media alone. Biofilm production was measure utilizing a crystal violet method.
Figure 14A:
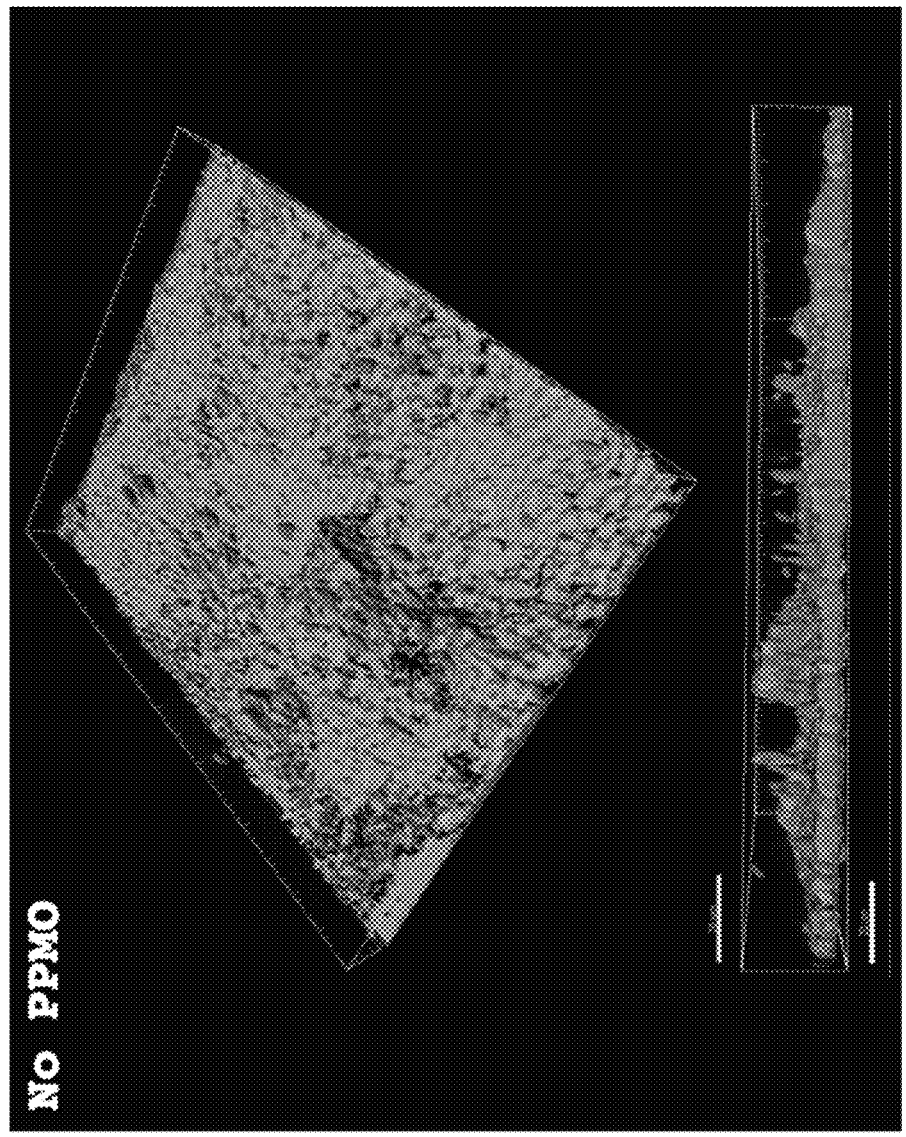
FIGS. 14A-14C show that acpP PPMO can break down an existing *B. cenocepacia* biofilm. dsRed-expressing *B. cenocepacia* J2315 was grown on MBEC pegs for 48 hours. The pegs were moved to fresh media containing either nothing, the Scrambled (Scr) control PPMO at 10 µM concentration, or the acpP PPMO at 10 µM concentration. The MBEC pegs were incubated for another 48 hours and then stained with fluorescent green peanut-agglutinin stain for the biofilm and imaged on confocal microscopy. While no PPMO (FIG. 14A) or Scr PPMO (FIG. 14B) displayed thick biofilms, the acpP PPMO-treated pegs (FIG. 14C) showed biofilm with pockets of no visible organisms.
Figure 14B:
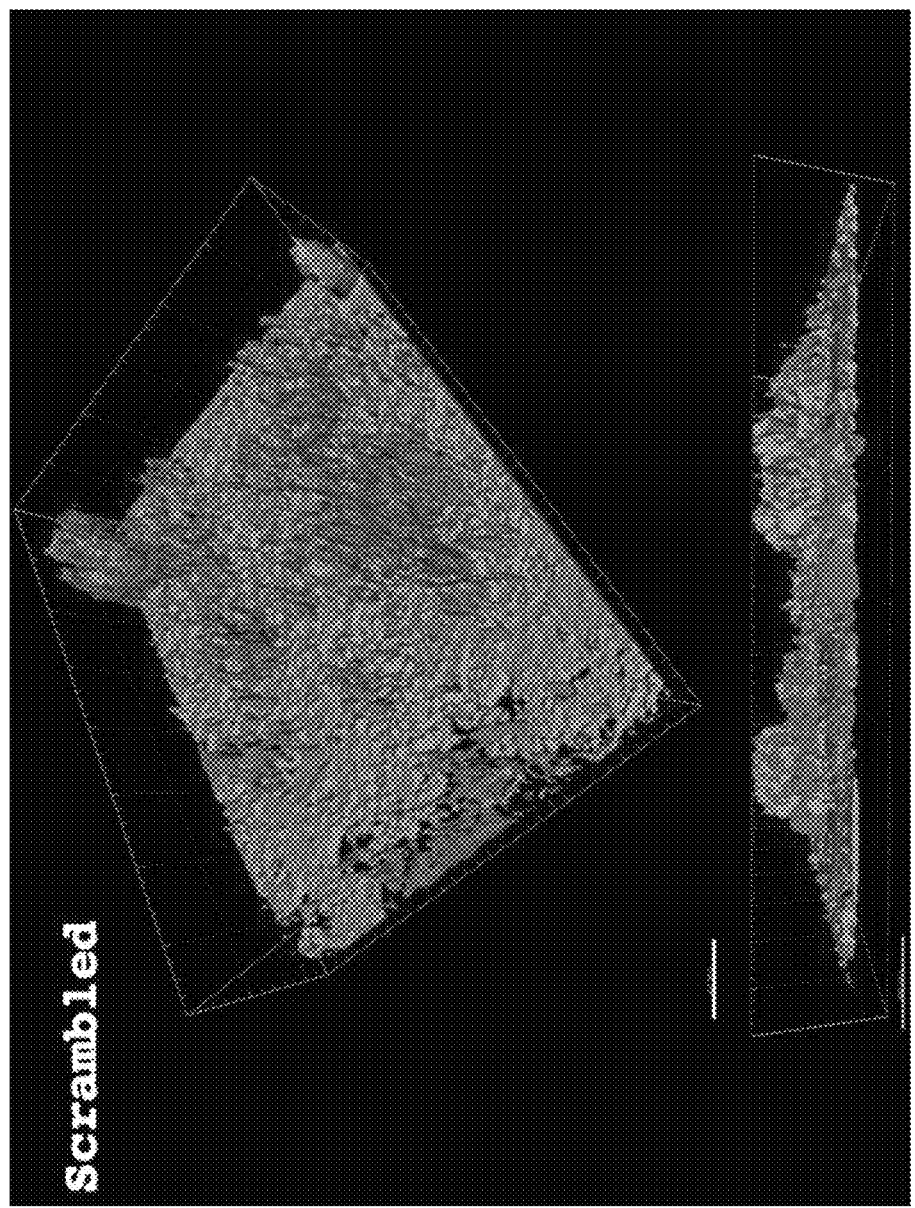
Figure 14C:
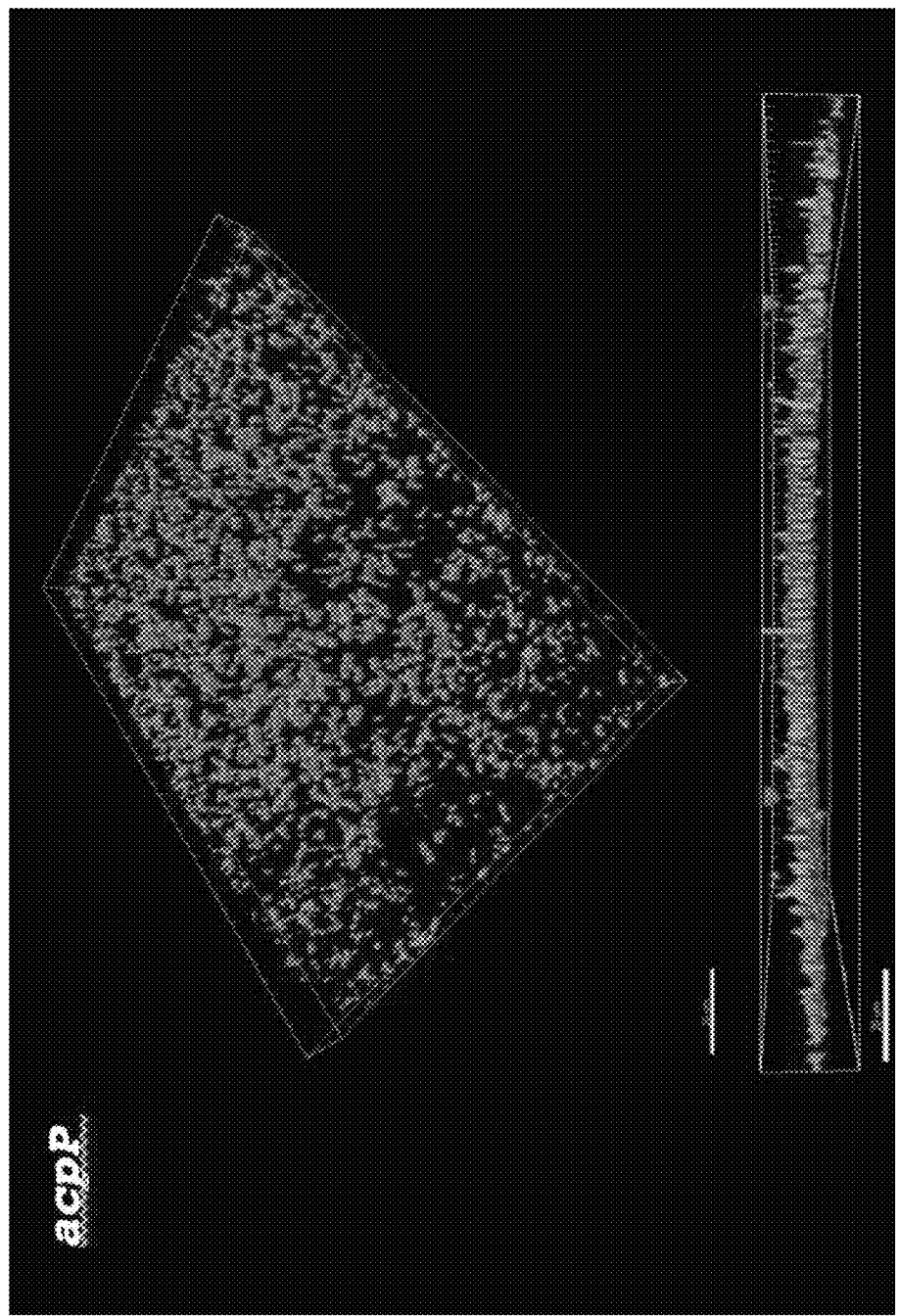

The formation of biofilm is a significant virulence trait and is utilized by both *P. aeruginosa* and the Bcc. Bcc biofilms were grown and PPMOs were tested for their ability to both prevent biofilm formation and to deconstruct existing biofilms. *B. cenocepacia* J2315 (a genome sequenced, epidemic CF isolate) was grown utilizing MBEC biofilm assay plates which contain a peg that grows reproducible biofilms from day to day. J2315 was grown for 48 hours in the presence of either acpP PPMO (10 μM), scrambled PPMO (10 μM), peptide or media alone (FIG. 13). The acpP-targeted PPMO (PPMO#19) has the following sequence:

CCATTACCCCT (SEQ ID NO: 27). The PPMO was conjugated at its 5' end to the beta-alanine residue of (RFF)$_3$RXB (SEQ ID NO: 41). Biofilm production was measured utilizing a crystal violet method. As can be seen, the acpP PPMO reduced biofilm formation by >50% compared to controls. The acpP PPMO was then tested to see if it could break down an existing biofilm. Biofilms were grown for 48 hours and then the mature biofilm pegs were transferred to a fresh plate with media alone (FIG. 14A), scrambled control PPMO at 10 µM (FIG. 14B) or acpP PPMO at 10 µM (FIG. 14C). The plates were incubated for 48 hours more and biofilm formation was measure both by crystal violet as well as by confocal microscopy. As measured by a fluorescent-red expressing J2315 strain, the acpP PPMO significantly reduced the amount of biofilm present both by confocal microscopy and crystal violet measurements (FIG. 14C). The ability of PPMOs (designed against essential gene targets) to break down existing biofilms is a novel and critically important finding.

Example 9

Figure 15:
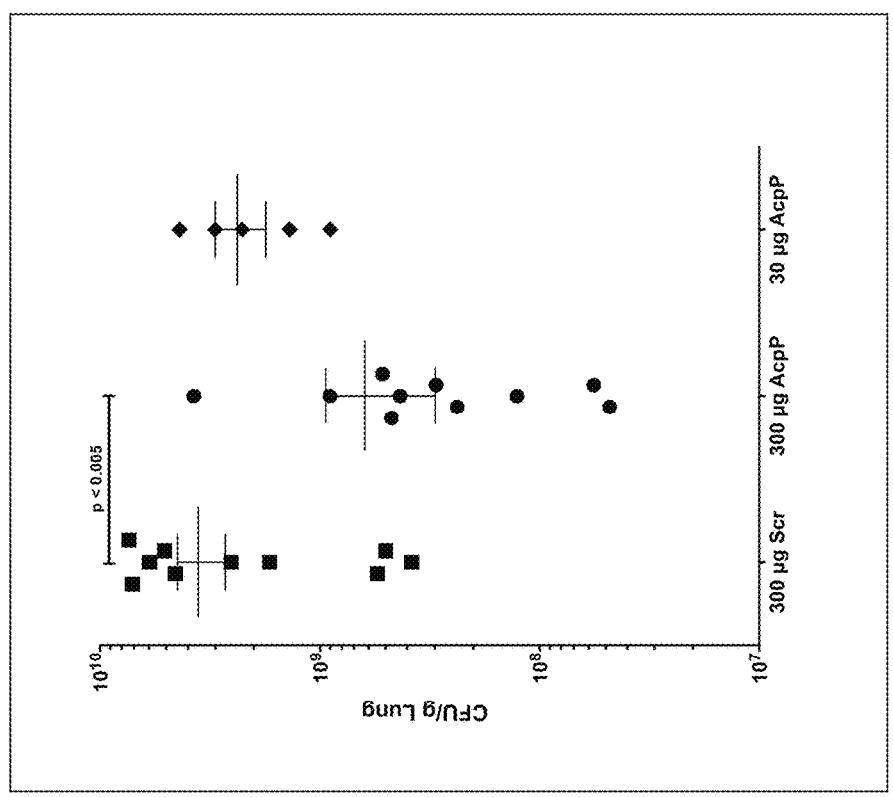
FIG. 15 shows that aerosol delivery of PPMO reduces the burden of *B. multivorans* in a pulmonary infection model. Chronic granulomatous disease (CGD) mice were used as a Bcc infection model. An Aerogen nebulizer was used to deliver either scrambled (Scr) PPMO (300 µg) or acpP PPMO (PPMO#15, Table 2C, 300 µg or 30 µg) as a one-time dose 6 hours post-infection. Mice were euthanized 24 hours after infection and lung burden was determined as CFU/g.

Aerosol Delivery of PPMO Reduces Burden of *B. multivorans* in a Pulmonary Infection Model Delivering PPMOs directly to the lung in the setting of chronic pulmonary infections would be useful. Chronic granulomatous disease (CGD) mice were used as a Bcc infection model. These mice develop significant morbidity and mortality when infected with various Bcc strains. Mice were infected intranasally with a clinical *B. multivorans* isolate (FIG. 15). An Aerogen nebulizer was used to deliver either scrambled (Scr) PPMO (300 µg) or acpP PPMO (PPMO#15, 300 µg or 30 µg) as a one-time dose 6 hours post-infection. The acpP-targeted PPMO has the following sequence: GTCCATTACCC (SEQ ID NO: 25). The PPMO was conjugated at its 5' end to the C-terminal β-alanine residue of (RFF)$_3$RXB (SEQ ID NO: 41). Mice were euthanized 24 hours after infection and lung burden was determined. The single 300 µg dose of the acpP PPMO reduced the lung burden by 93% and was a statistically significant decrease. Aerosol delivery of PPMOs is a viable therapeutic strategy and importantly, this is the first time that nebulized delivery of Bcc PPMOs has been attempted.

The invention claimed is:

1. An antisense morpholino oligomer of formula (I):

[Structure (I): morpholino oligomer showing repeating subunits with T at 5' end, Nu nucleobases, phosphorodiamidate linkages O=P-R¹, repeating X times, terminating in morpholine with R² and R³ substituents on nitrogen]

or a pharmaceutically acceptable salt thereof, where each Nu is a nucleobase which taken together forms a targeting sequence;

X is an integer from 9 to 38;

T is selected from OH and a moiety of the formula:

[Structure: O=P(R⁶)(—N(R⁴)₂R⁵)—O—]

where each R⁴ is independently $C_1$-$C_6$ alkyl, and R⁵ is selected from an electron pair and H, and R⁶ is selected from OH, —N(R⁷)CH₂C(O)NH₂, and a moiety of the formula:

[Structure: piperazine ring with —R⁸ substituent]

where:

R⁷ is selected from H and $C_1$-$C_6$ alkyl, and

R⁸ is selected from G, —C(O)—R⁹OH, acyl, trityl, and 4-methoxytrityl, where:

R⁹ is of the formula —(O-alkyl)$_y$- wherein y is an integer from 3 to 10 and each of the y alkyl groups is independently selected from $C_2$-$C_6$ alkyl;

each instance of R¹ is —N(R¹⁰)₂R¹¹ wherein each R¹⁰ is independently $C_1$-$C_6$ alkyl, and R¹¹ is selected from an electron pair and H;

R² is selected from H, G, acyl, trityl, 4-methoxytrityl, benzoyl, stearoyl, and a moiety of the formula:

[Structure: L—N-piperazine—N—triazine with (R¹²)₂N and N(R¹²)₂ substituents]

where L is selected from —C(O)(CH₂)₆C(O)— and —C(O)(CH₂)₂S₂(CH₂)₂C(O)—, and each R¹² is of the formula —(CH₂)₂OC(O)N(R¹⁴)₂ wherein each R¹⁴ is of the formula —(CH₂)₆NHC(=NH)NH₂; and R³ is selected from an electron pair, H, and $C_1$-$C_6$ alkyl, wherein G is a cell penetrating peptide ("CPP") and linker moiety selected from —C(O)(CH₂)₅NH—CPP, —C(O)(CH₂)₂NH—CPP, —C(O)(CH₂)₂NHC(O)(CH₂)₅NH—CPP, and —C(O)CH₂NH—CPP, or G is of the formula:

[Structure: pyrrolidine-2-carbonyl with CPP attached to N]

wherein the CPP is attached to the linker moiety by an amide bond at the CPP carboxy terminus, with the proviso that only one instance of G is present, wherein the targeting sequence specifically hybridizes to a bacterial mRNA target sequence that encodes a virulence factor, and wherein the targeting sequence is selected from:

a) SEQ ID NO: 11 (TCA AGT TTT CC);

b) SEQ ID NO: 12 (TCC TTT TAT TC);

c) SEQ ID NO: 13 (CCA TCA AGT TT);

d) SEQ ID NO: 14 (GGC AAT TCC AT);

e) SEQ ID NO: 15 (ATA CTG TCC AA);

wherein X is 9, and thymine bases (T) may be uracil bases(U).

2. The antisense morpholino oligomer of claim 1, wherein T is selected from:

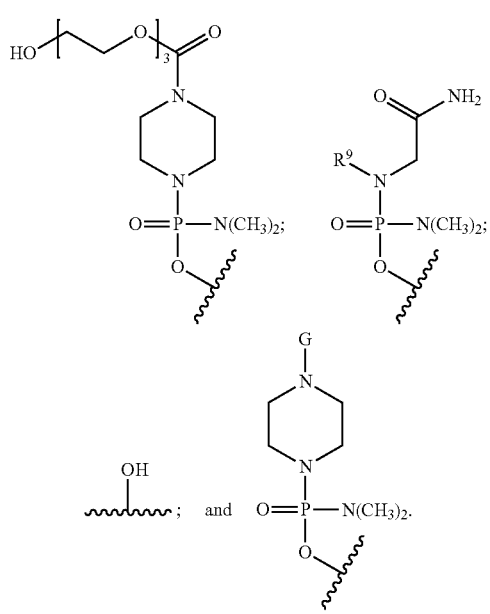

3. The antisense morpholino oligomer of claim 2, wherein $R^2$ is selected from H, G, acyl, trityl, 4-methoxytrityl, benzoyl, and stearoyl.

4. The antisense morpholino oligomer of claim 1, wherein T is selected from:

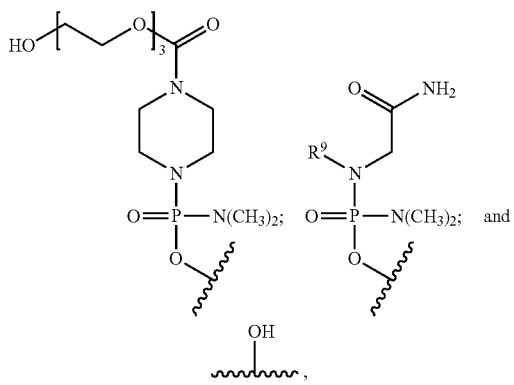

and
$R^2$ is G.

5. The antisense morpholino oligomer of claim 1, wherein T is of the formula:

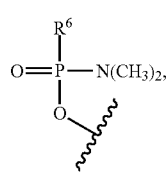

$R^6$ is of the formula:

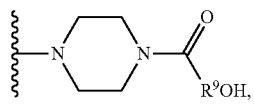

and $R^2$ is G.

6. The antisense morpholino oligomer of claim 1, wherein T is of the formula:

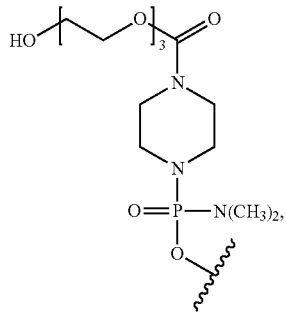

and $R^2$ is G.

7. The antisense morpholino oligomer of claim 1, wherein T is of the formula:

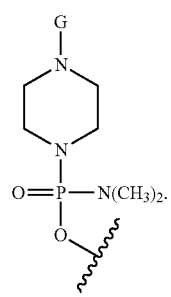

8. The antisense morpholino oligomer according to claim 7, wherein $R^2$ is selected from H, acyl, trityl, 4-methoxytrityl, benzoyl, and stearoyl.

9. The antisense morpholino oligomer according to claim 8, wherein at least one instance of $R^1$ is —N(CH$_3$)$_2$.

10. The antisense morpholino oligomer of claim 9, wherein each $R^1$ is —N(CH$_3$)$_2$.

11. The antisense morpholino oligomer according to claim 1, wherein the CPP is selected from:

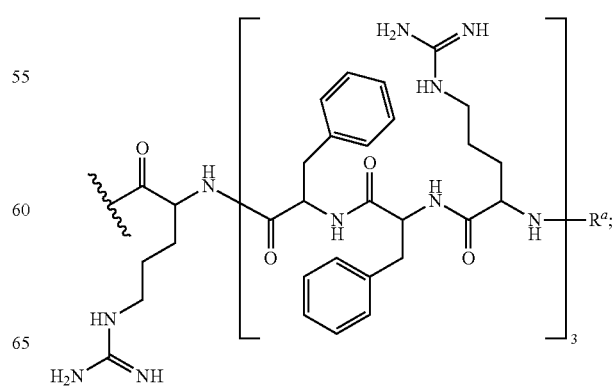

-continued
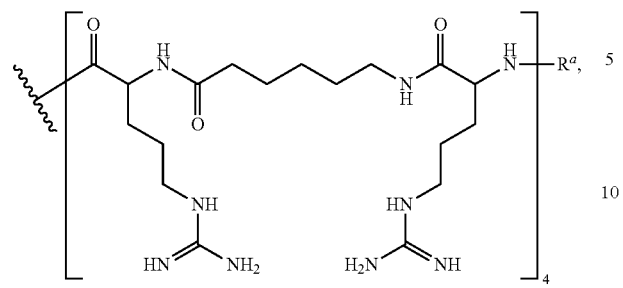
wherein $R^a$ is selected from H, acetyl, benzoyl, and stearoyl.
12. The antisense morpholino oligomer according to claim 1, wherein G is selected from:
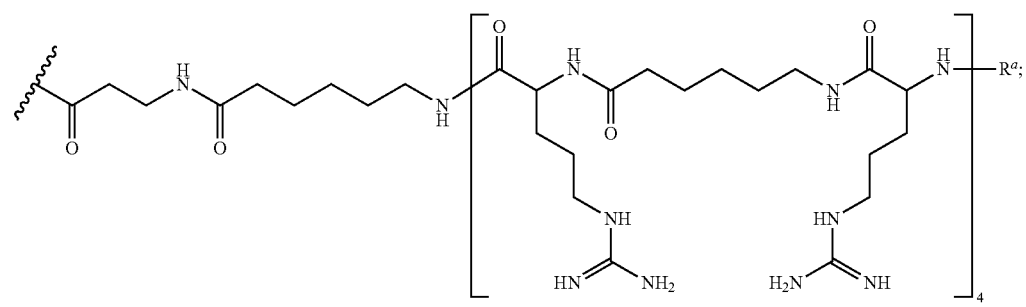
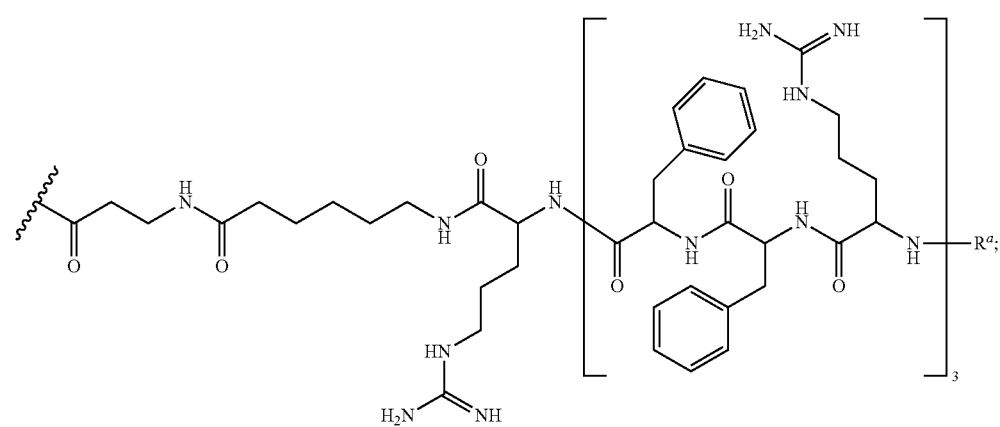

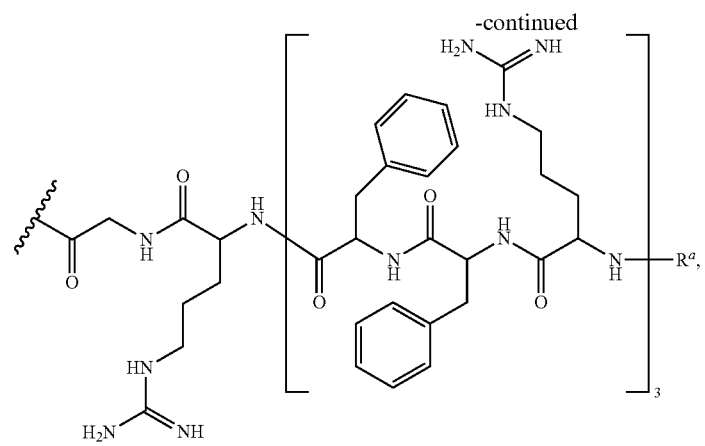
wherein $R^a$ is selected from H, acetyl, benzoyl, and stearoyl.
13. An antisense morpholino oligomer of formula (VII) selected from:

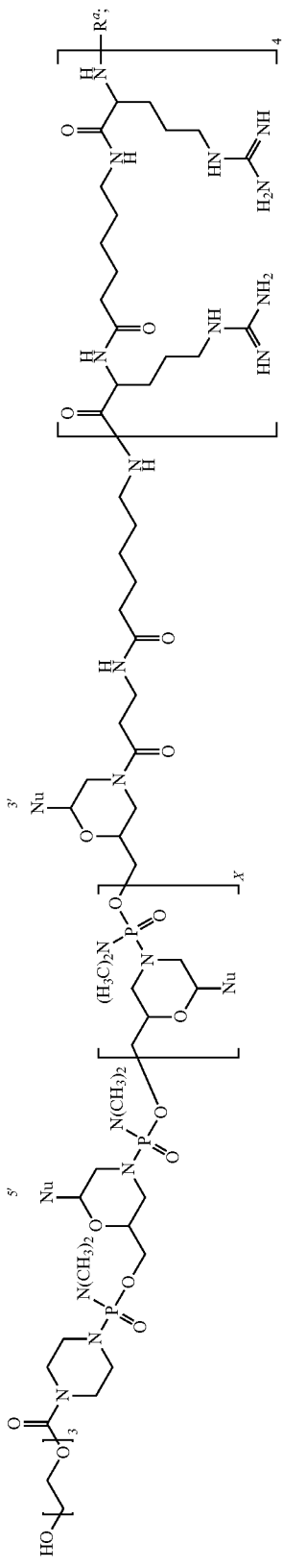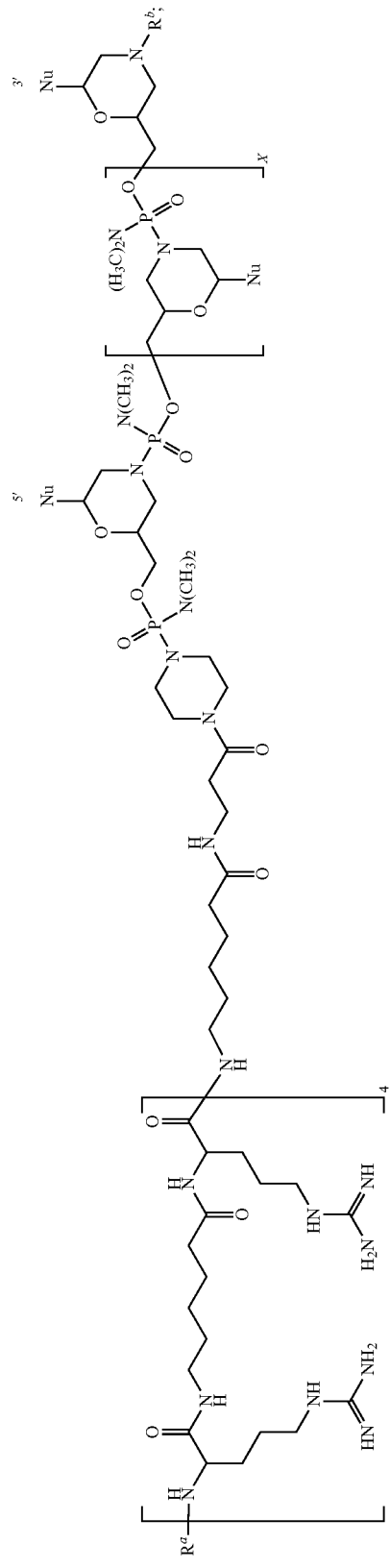

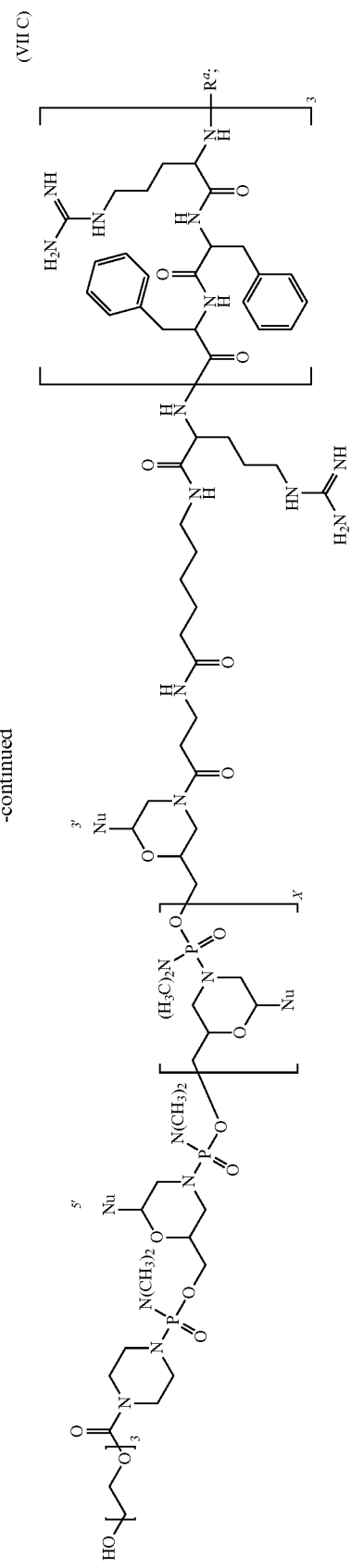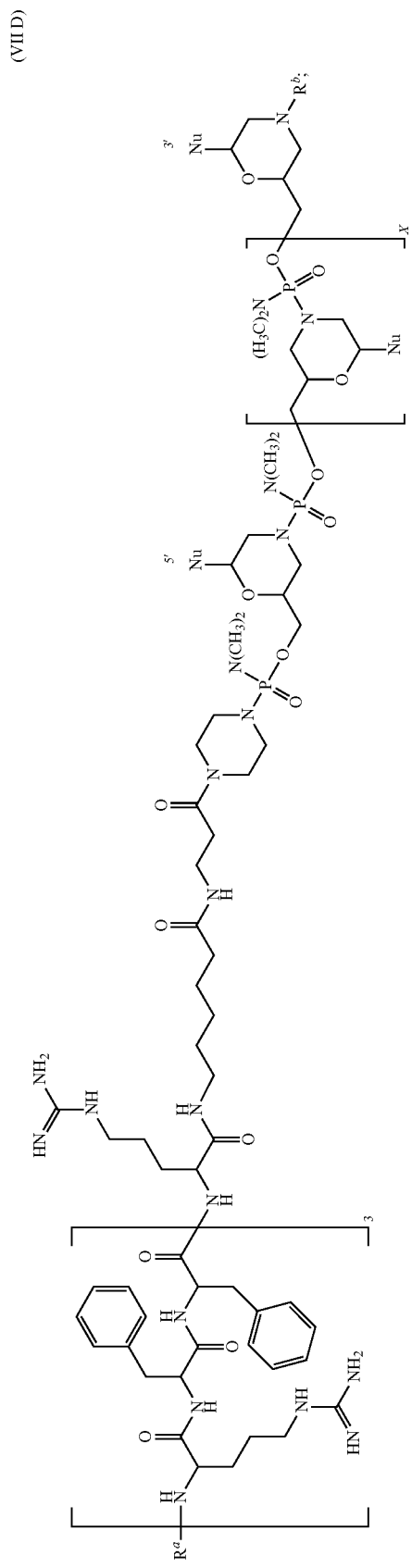

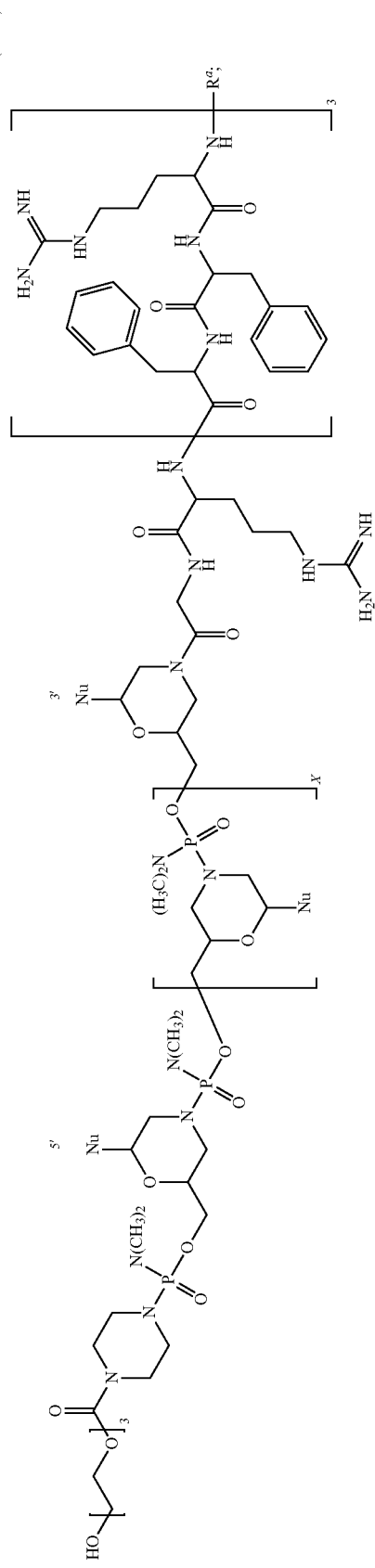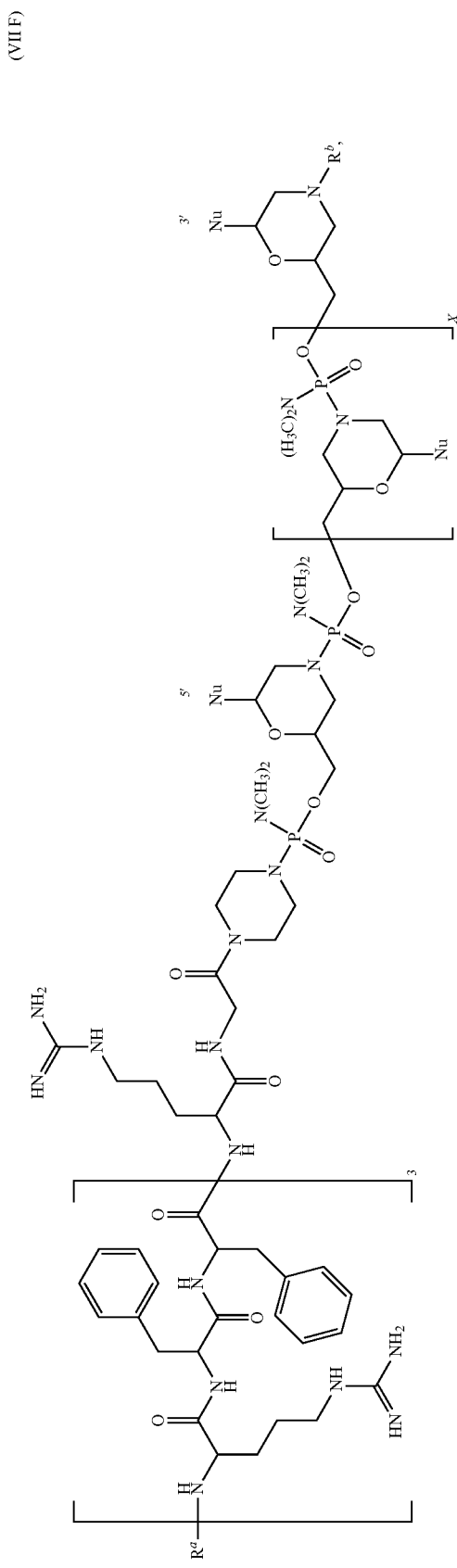

or a pharmaceutically acceptable salt of any of the foregoing, wherein $R^a$ is H or acetyl, each Nu is a nucleobase which taken together forms a targeting sequence, and the targeting sequence is selected from:

f) SEQ ID NO: 11 (TCA AGT TTT CC);

g) SEQ ID NO: 12 (TCC TTT TAT TC);

h) SEQ ID NO: 13 (CCA TCA AGT TT);

i) SEQ ID NO: 14 (GGC AAT TCC AT);

j) SEQ ID NO: 15 (ATA CTG TCC AA);

wherein X is 9, and thymine bases (T) may be uracil bases(U).

14. A pharmaceutical composition, comprising a pharmaceutically acceptable carrier and an antisense morpholino oligomer of formula (I):

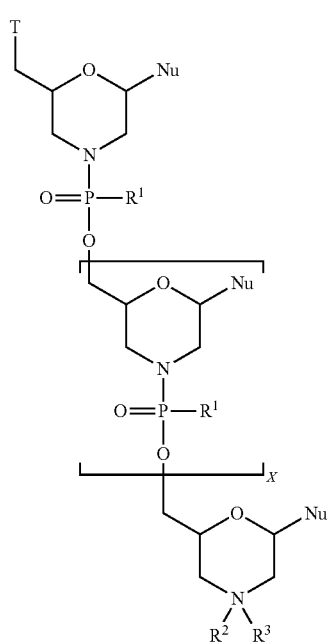
(I)

or a pharmaceutically acceptable salt thereof, where each Nu is a nucleobase which taken together forms a targeting sequence;

X is an integer from 9 to 38;

T is selected from OH and a moiety of the formula:

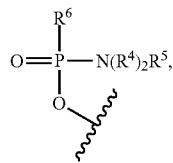

where each $R^4$ is independently $C_1$-$C_6$ alkyl, and $R^5$ is selected from an electron pair and H, and $R^6$ is selected from OH, —N($R^7$)CH$_2$C(O)NH$_2$, and a moiety of the formula:

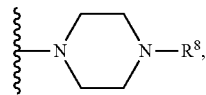

where:

$R^7$ is selected from H and $C_1$-$C_6$ alkyl, and $R^8$ is selected from G, —C(O)—$R^9$OH, acyl, trityl, and 4-methoxytrityl, where:

$R^9$ is of the formula —(O-alkyl)$_y$- wherein y is an integer from 3 to 10 and each of the y alkyl groups is independently selected from $C_2$-$C_6$ alkyl;

each instance of $R^1$ is —N($R^{10}$)$_2$$R^{11}$ wherein each $R^{10}$ is independently $C_1$-$C_6$ alkyl, and $R^{11}$ is selected from an electron pair and H;

$R^2$ is selected from H, G, acyl, trityl, 4-methoxytrityl, benzoyl, stearoyl, and a moiety of the formula:

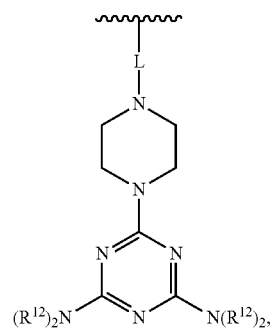

where L is selected from —C(O)(CH$_2$)$_6$C(O)— and —C(O)(CH$_2$)$_2$S$_2$(CH$_2$)$_2$C(O)—, and each $R^{12}$ is of the formula —(CH$_2$)$_2$OC(O)N($R^{14}$)$_2$ wherein each $R^{14}$ is of the formula —(CH$_2$)$_6$NHC(=NH)NH$_2$; and $R^3$ is selected from an electron pair, H, and $C_1$-$C_6$ alkyl, wherein G is a cell penetrating peptide ("CPP") and linker moiety selected from
—C(O)(CH$_2$)$_5$NH—CPP, —C(O)(CH$_2$)$_2$NH—CPP,
—C(O)(CH$_2$)$_2$NHC(O)(CH$_2$)$_5$NH—CPP,
and —C(O)CH$_2$NH—CPP, or G is of the formula:

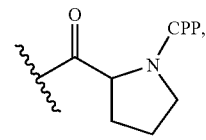

wherein the CPP is attached to the linker moiety by an amide bond at the CPP carboxy terminus, with the proviso that only one instance of G is present, wherein the targeting sequence specifically hybridizes to a bacterial mRNA target sequence that encodes a virulence factor, and wherein the targeting sequence is selected from:

k) SEQ ID NO: 11 (TCA AGT TTT CC);

l) SEQ ID NO: 12 (TCC TTT TAT TC);

m) SEQ ID NO: 13 (CCA TCA AGT TT);

n) SEQ ID NO: 14 (GGC AAT TCC AT);

o) SEQ ID NO: 15 (ATA CTG TCC AA);

wherein X is 9, and thymine bases (T) may be uracil bases(U).

15. The antisense oligomer of claim 13, wherein the antisense oligomer is:
(VII A)
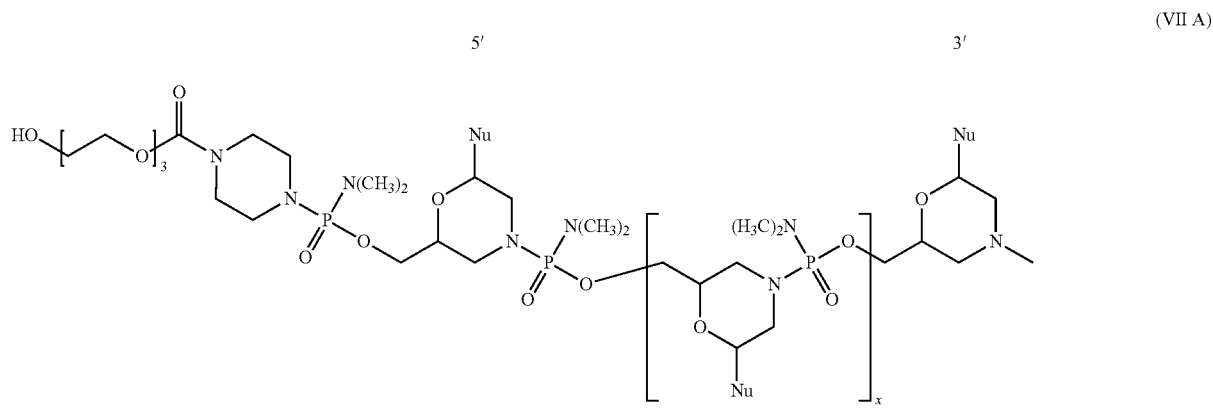
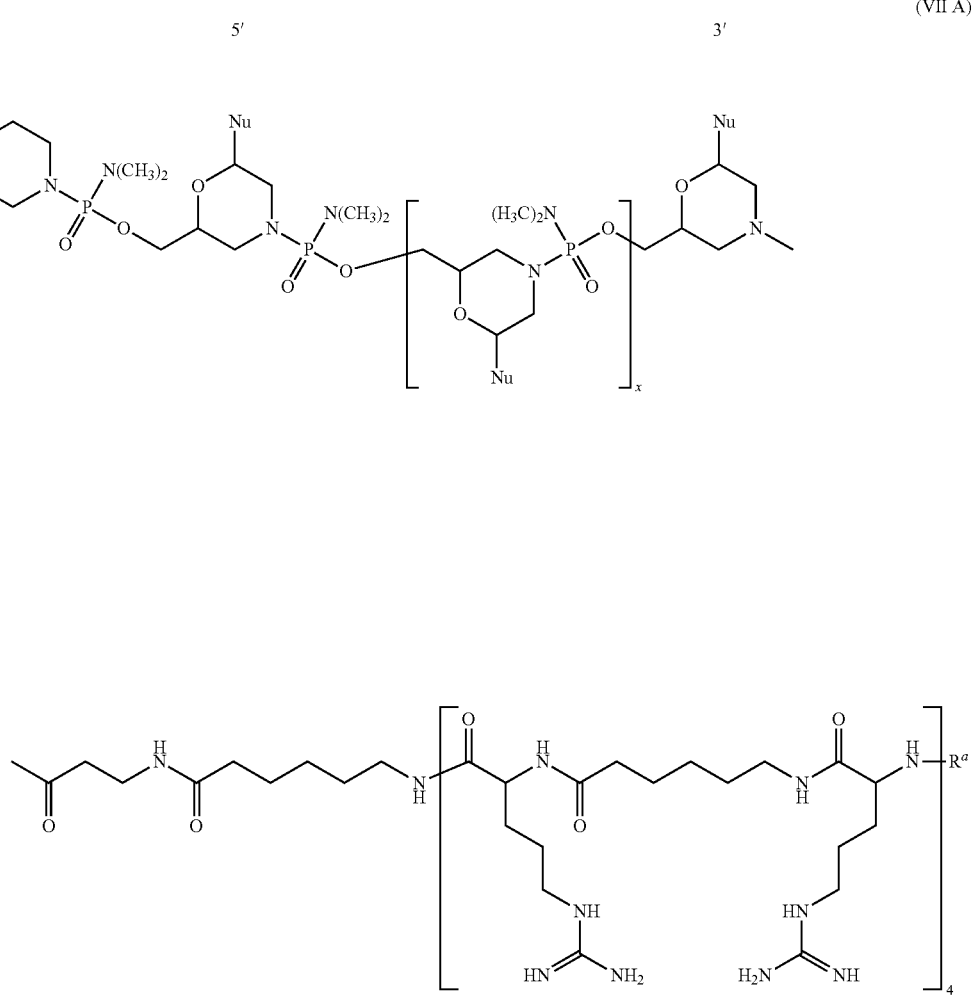
or a pharmaceutically acceptable salt thereof, wherein $R^a$ is H or acetyl, and the targeting sequence consists of SEQ ID NO: 11 (TCA AGT TTT CC) wherein X is 9.
16. The antisense oligomer of claim 13, wherein the antisense oligomer is:
(VII A)
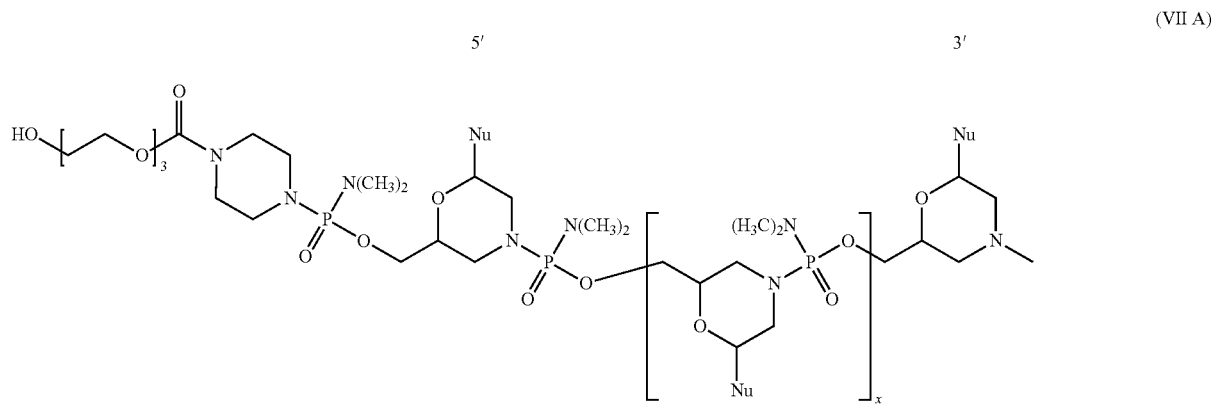

-continued
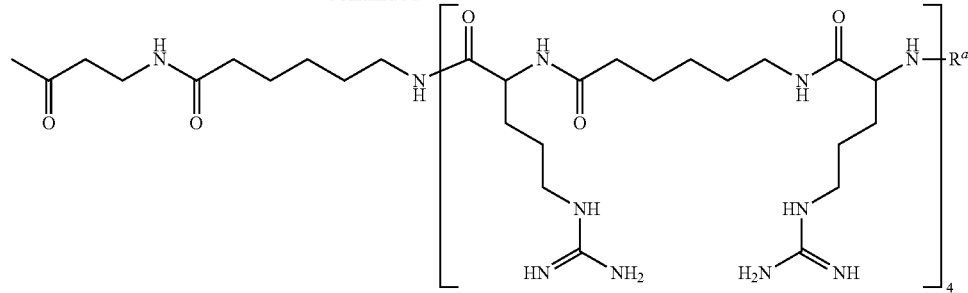
or a pharmaceutically acceptable salt thereof, wherein W is H or acetyl, and the targeting sequence consists of SEQ ID NO: 12 (TCC TTT TAT TC) wherein X is 9.
17. The antisense oligomer of claim 13, wherein the antisense oligomer is:
(VII A)
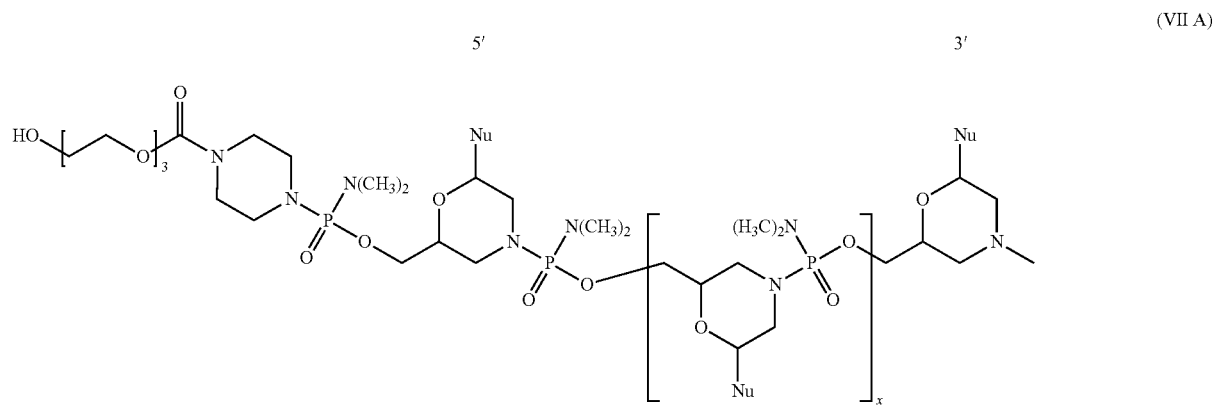
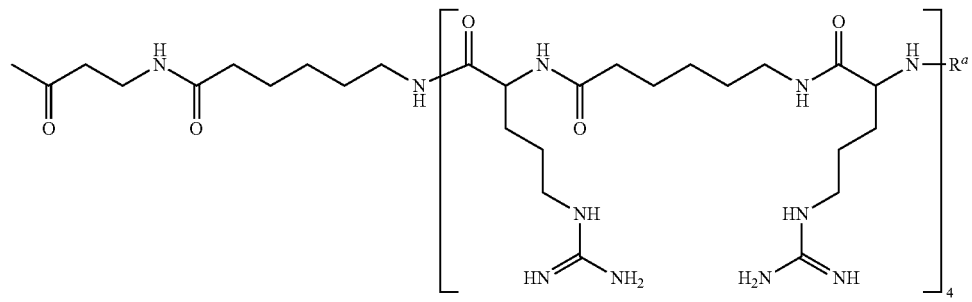

or a pharmaceutically acceptable salt thereof, wherein W is H or acetyl, and the targeting sequence consists of SEQ ID NO: 13 (CCA TCA AGT TT) wherein X is 9.

18. The antisense oligomer of claim 13, wherein the antisense oligomer is:

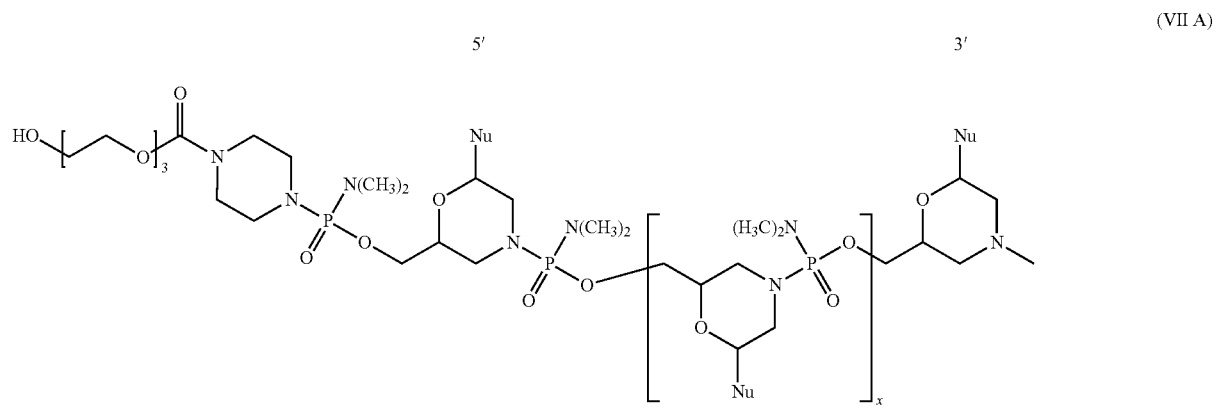

(VII A)

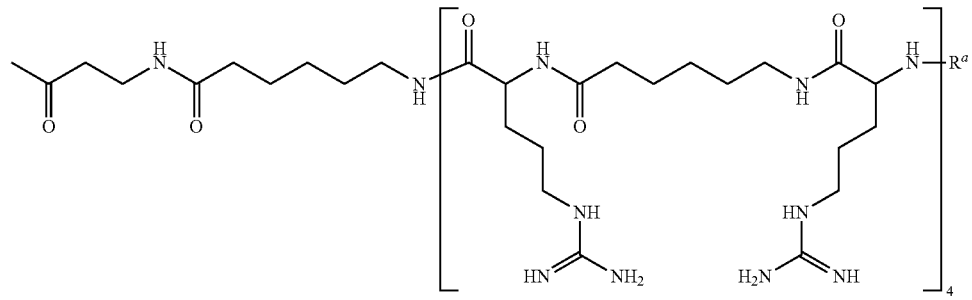

or a pharmaceutically acceptable salt thereof, wherein W is H or acetyl, and the targeting sequence consists of SEQ ID NO: 14 (GGC AAT TCC AT) wherein X is 9.

19. The antisense oligomer of claim 13, wherein the antisense oligomer is:

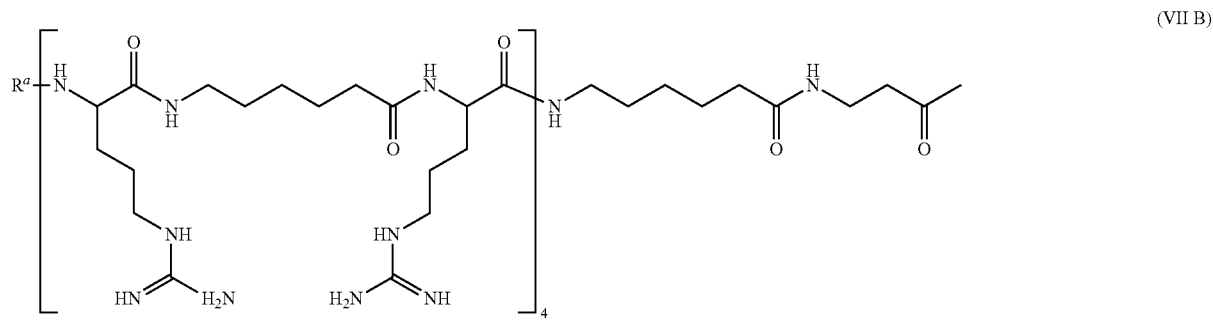

(VII B)

-continued
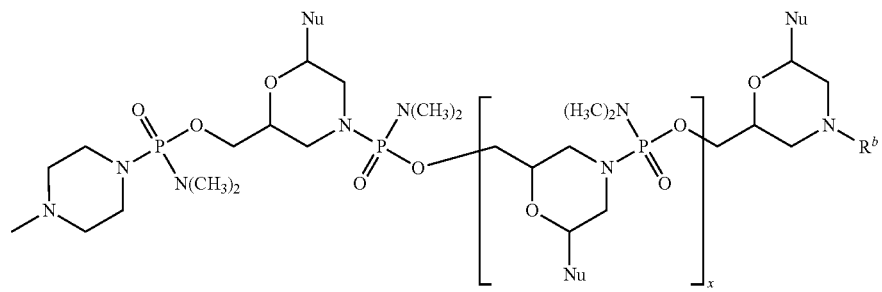
or a pharmaceutically acceptable salt thereof, wherein $R^a$ is H or acetyl, and the targeting sequence consists of SEQ ID NO: 11 (TCA AGT TTT CC) wherein X is 9.
20. The antisense oligomer of claim 13, wherein the antisense oligomer is:
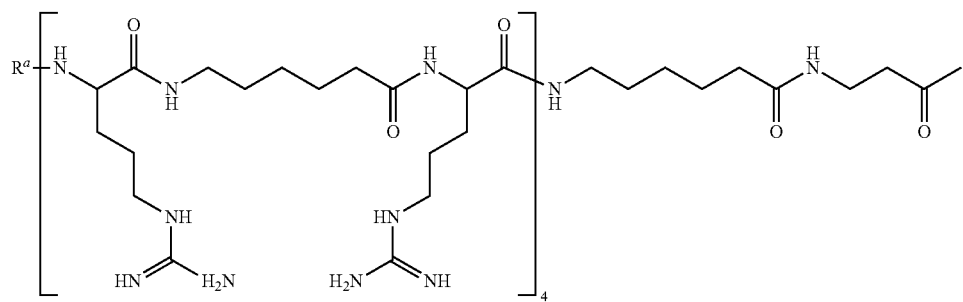
(VII B)
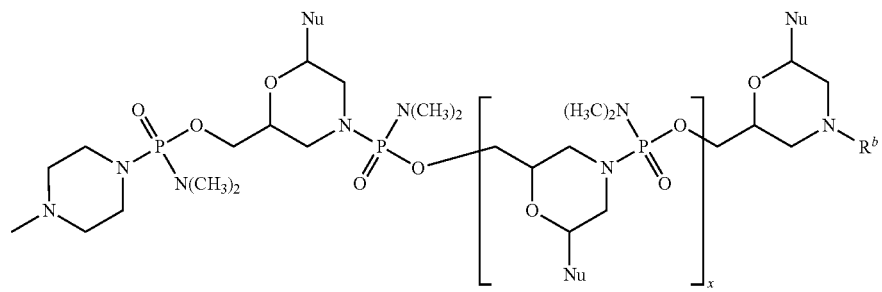

or a pharmaceutically acceptable salt thereof, wherein W is H or acetyl, and the targeting sequence consists of SEQ ID NO: 12 (TCC TTT TAT TC) wherein X is 9.

21. The antisense oligomer of claim 13, wherein the antisense oligomer is:

(VII B)

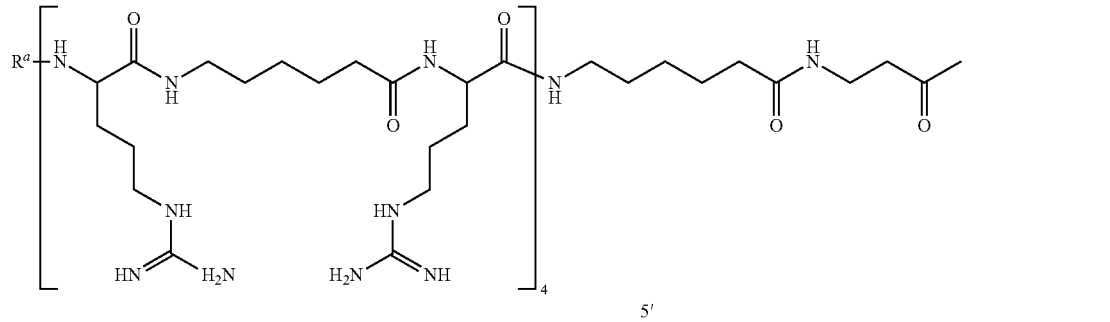

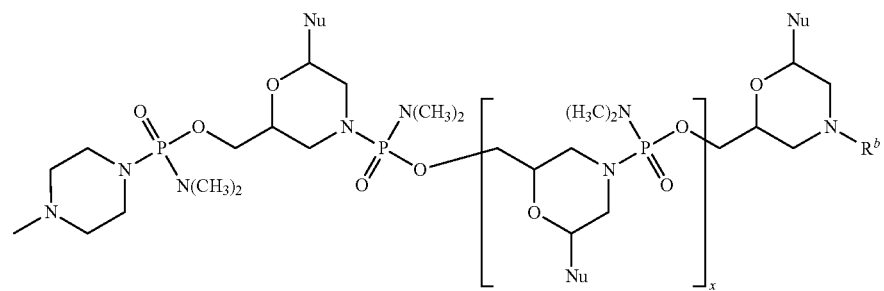

or a pharmaceutically acceptable salt thereof, wherein W is H or acetyl, and the targeting sequence consists of SEQ ID NO: 13 (CCA TCA AGT TT) wherein X is 9.

22. The antisense oligomer of claim 13, wherein the antisense oligomer is:

(VII B)

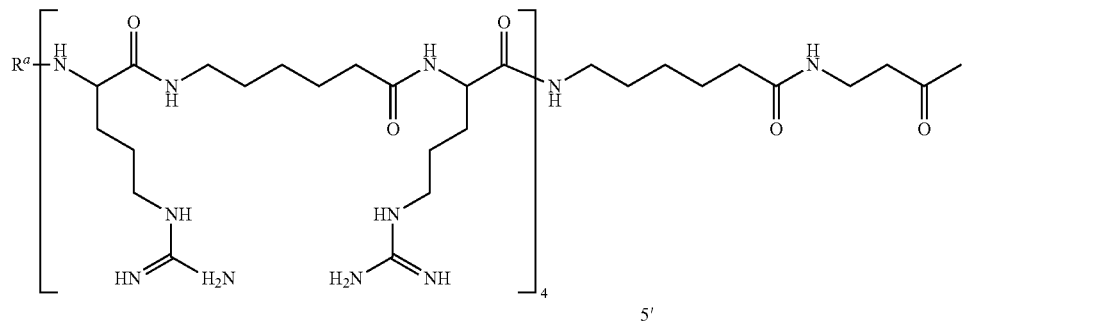

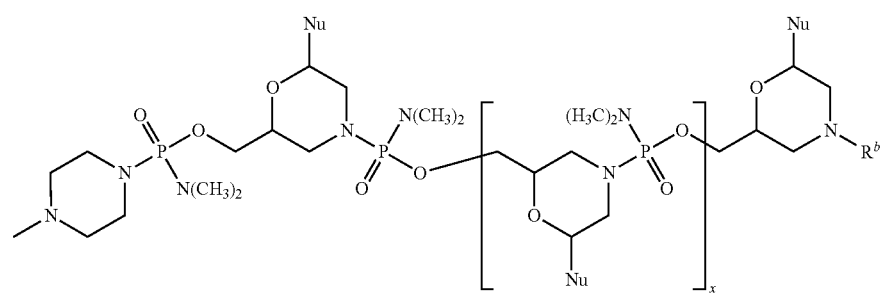

or a pharmaceutically acceptable salt thereof, wherein $R^a$ is H or acetyl, and the targeting sequence consists of SEQ ID NO: 14 (GGC AAT TCC AT) wherein X is 9.

23. The antisense oligomer of claim 13, wherein the antisense oligomer is:

(VII C)

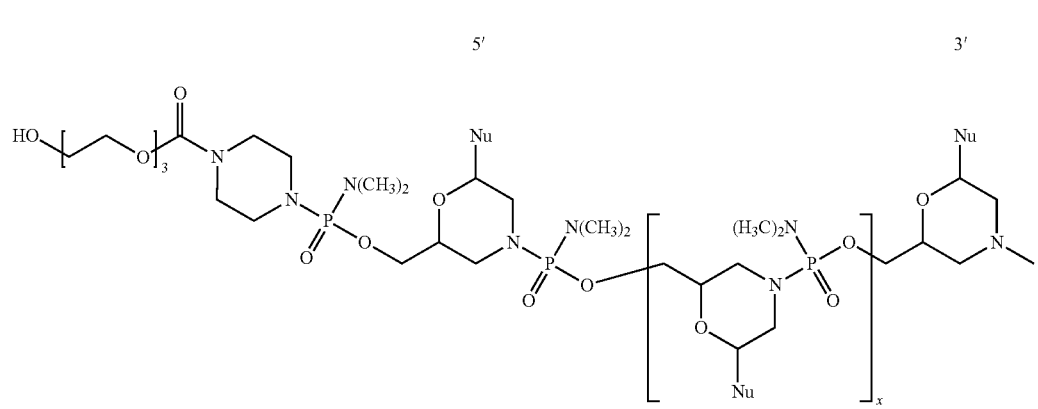

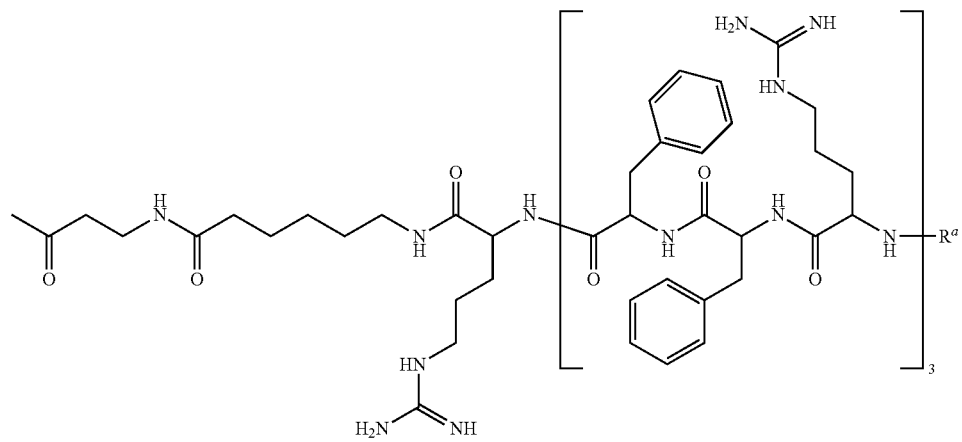

or a pharmaceutically acceptable salt thereof, wherein W is H or acetyl, and the targeting sequence consists of SEQ ID NO: 11 (TCA AGT TTT CC) wherein X is 9.

24. The antisense oligomer of claim 13, wherein the antisense oligomer is:

(VII C)

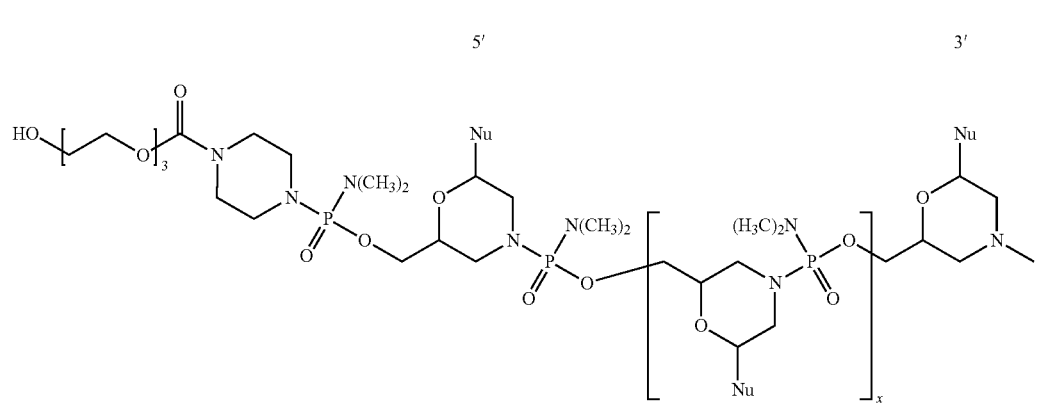

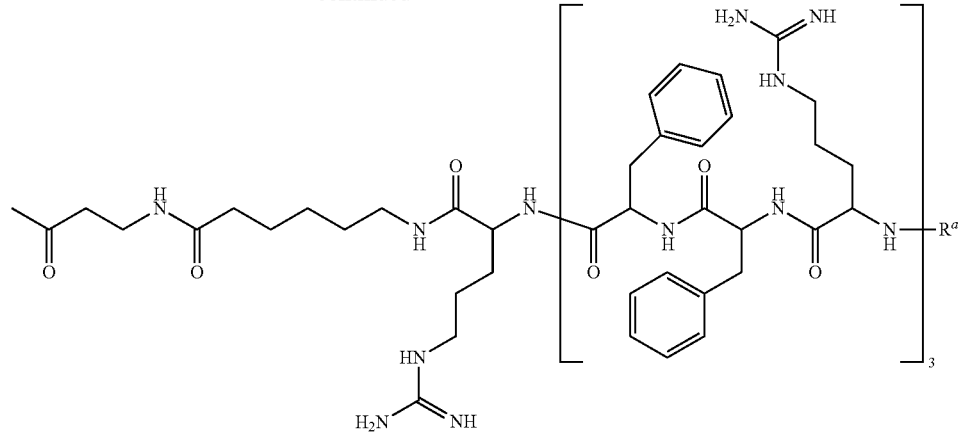
or a pharmaceutically acceptable salt thereof, wherein W is H or acetyl, and the targeting sequence consists of SEQ ID NO: 12 (TCC TTT TAT TC) wherein X is 9.
25. The antisense oligomer of claim 13, wherein the antisense oligomer is:
(VII C)
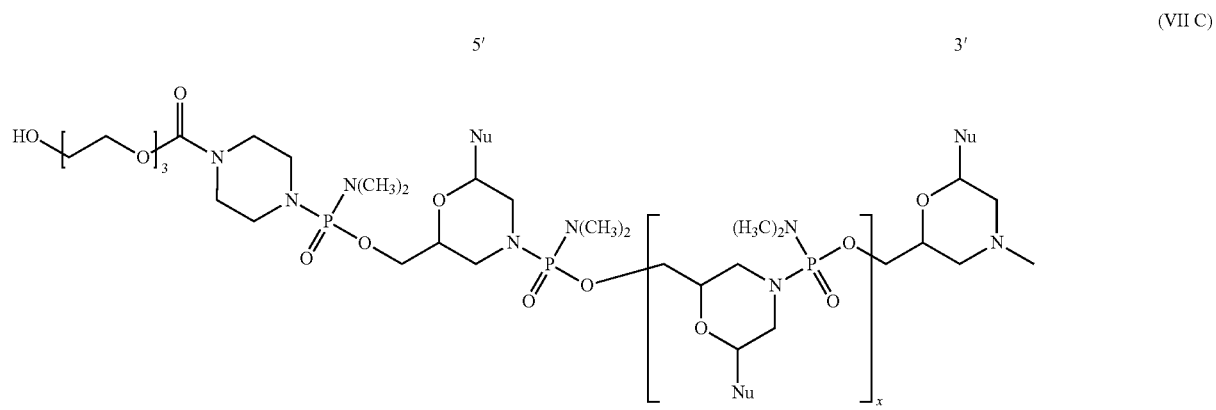
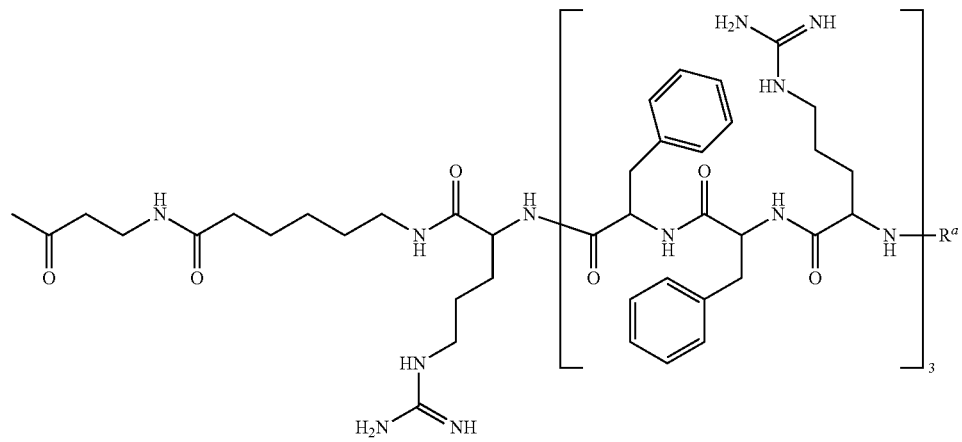

or a pharmaceutically acceptable salt thereof, wherein W is H or acetyl, and the targeting sequence consists of SEQ ID NO: 13 (CCA TCA AGT TT) wherein X is 9.
26. The antisense oligomer of claim 13, wherein the antisense oligomer is:
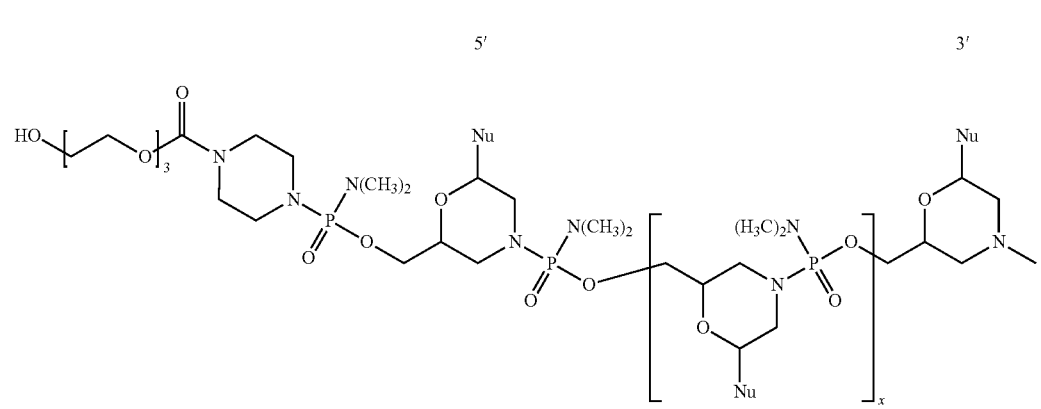
(VII C)
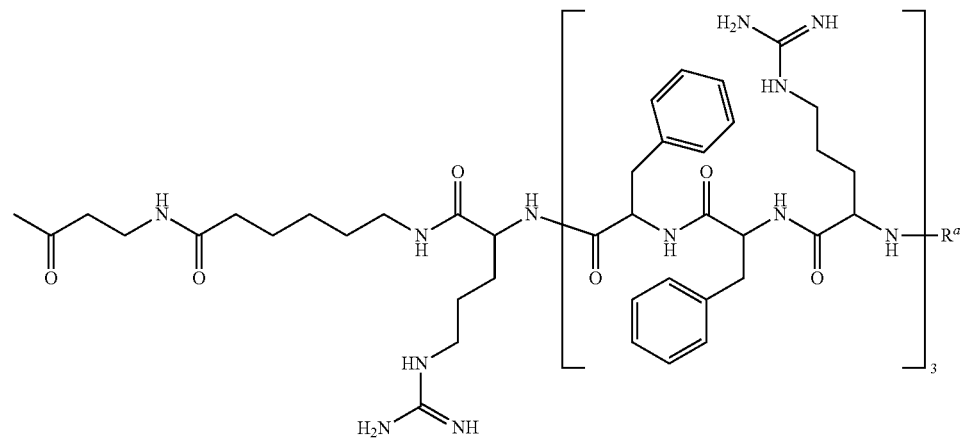

or a pharmaceutically acceptable salt thereof, wherein W is H or acetyl, and the targeting sequence consists of SEQ ID NO: 14 (GGC AAT TCC AT) wherein X is 9.

27. The antisense oligomer of claim 13, wherein the antisense oligomer is:

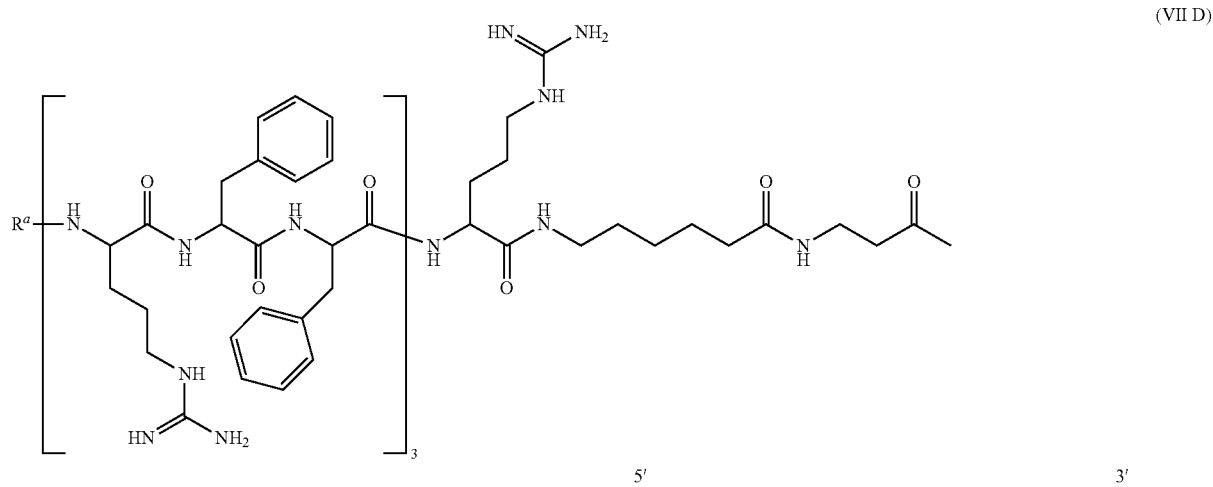

(VII D)

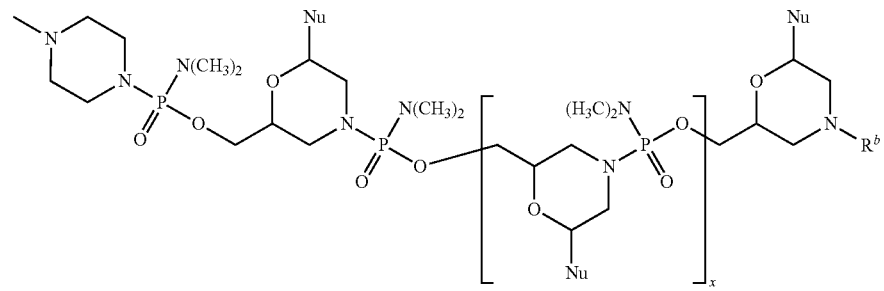

or a pharmaceutically acceptable salt thereof, wherein W is H or acetyl, and the targeting sequence consists of SEQ ID NO: 11 (TCA AGT TTT CC) wherein X is 9.

28. The antisense oligomer of claim 13, wherein the antisense oligomer is:

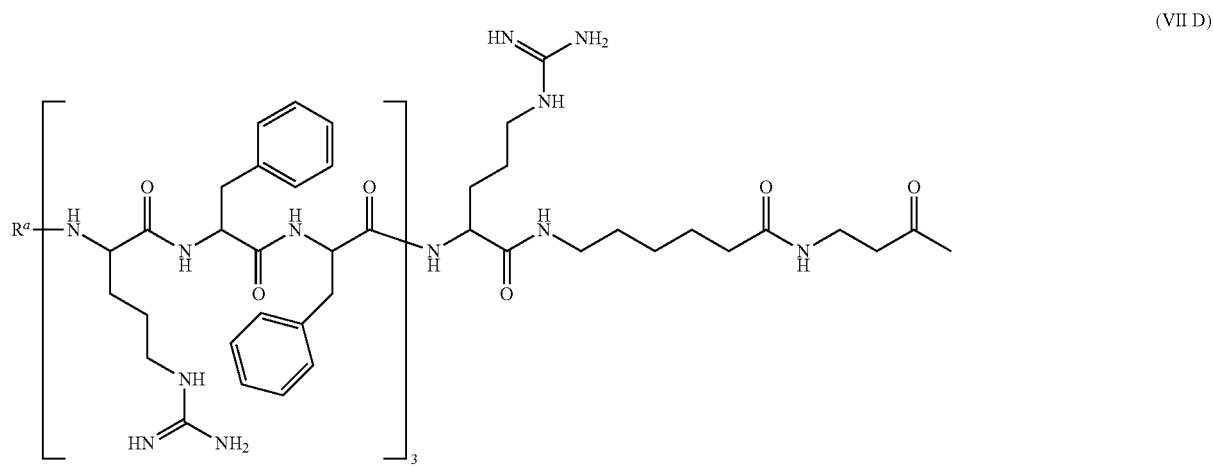

(VII D)

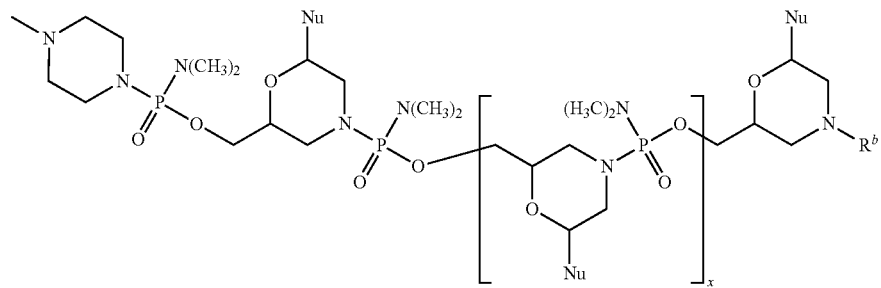
or a pharmaceutically acceptable salt thereof, wherein W is H or acetyl, and the targeting sequence consists of SEQ ID NO: 12 (TCC TTT TAT TC) wherein X is 9.
29. The antisense oligomer of claim 13, wherein the antisense oligomer is:
(VII D)
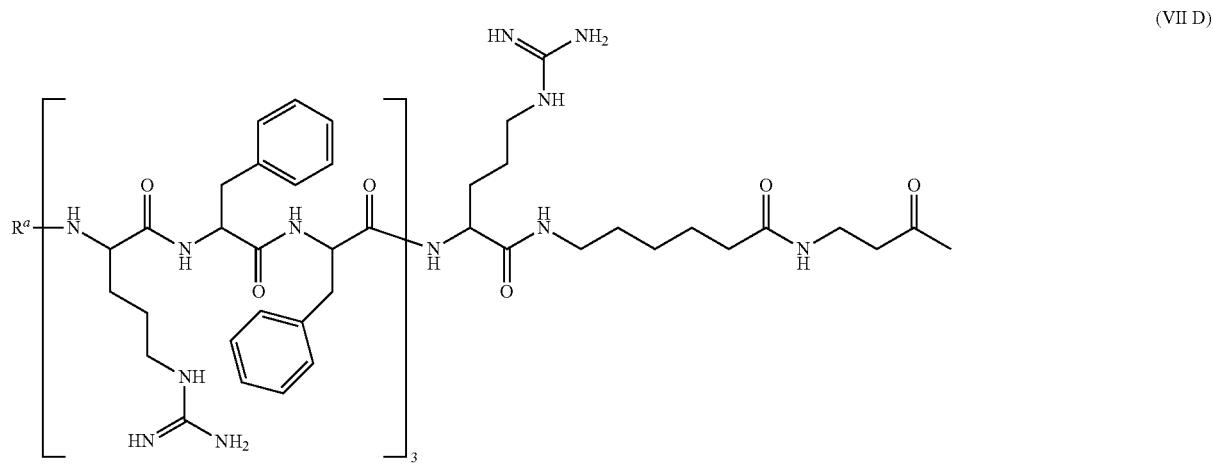
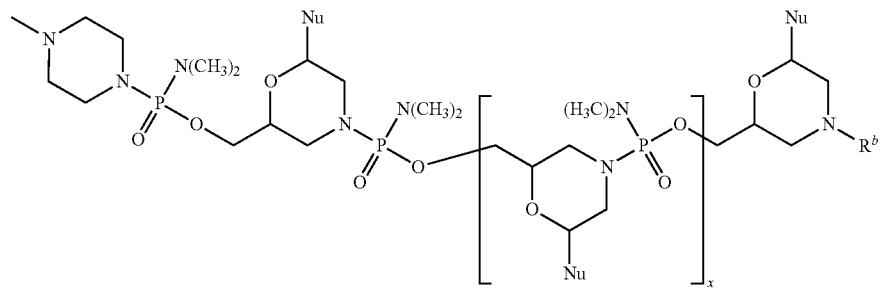

or a pharmaceutically acceptable salt thereof, wherein $R^a$ is H or acetyl, and the targeting sequence consists of SEQ ID NO: 13 (CCA TCA AGT TT) wherein X is 9.
30. The antisense oligomer of claim 13, wherein the antisense oligomer is:
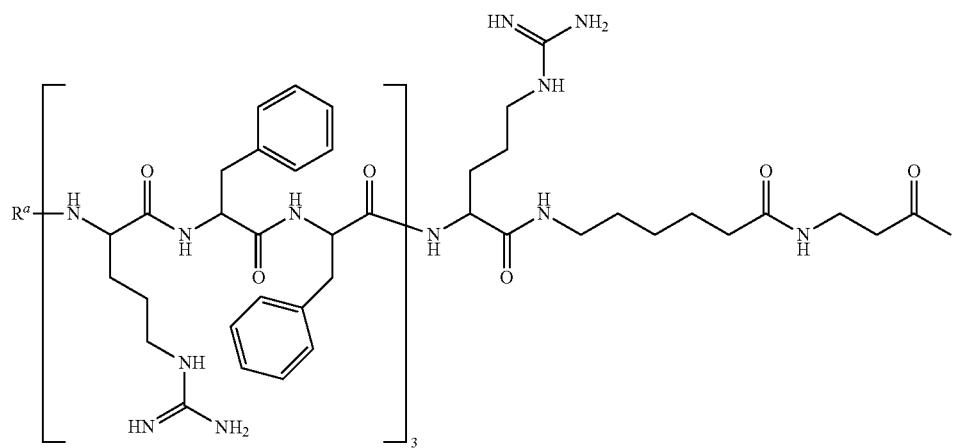
(VII D)
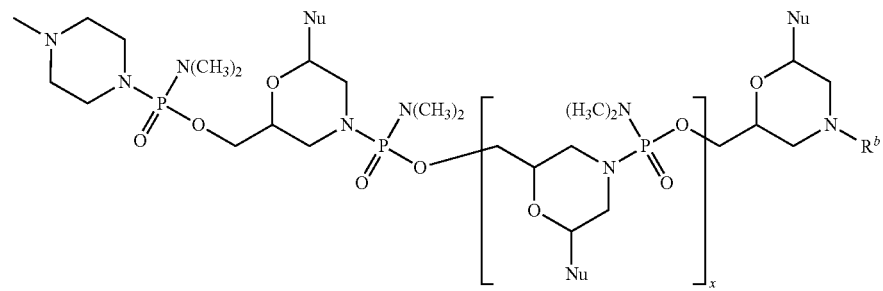

or a pharmaceutically acceptable salt thereof, wherein W is H or acetyl, and the targeting sequence consists of SEQ ID NO: 14 (GGC AAT TCC AT) wherein X is 9.

31. The antisense oligomer of claim 13, wherein the antisense oligomer is:

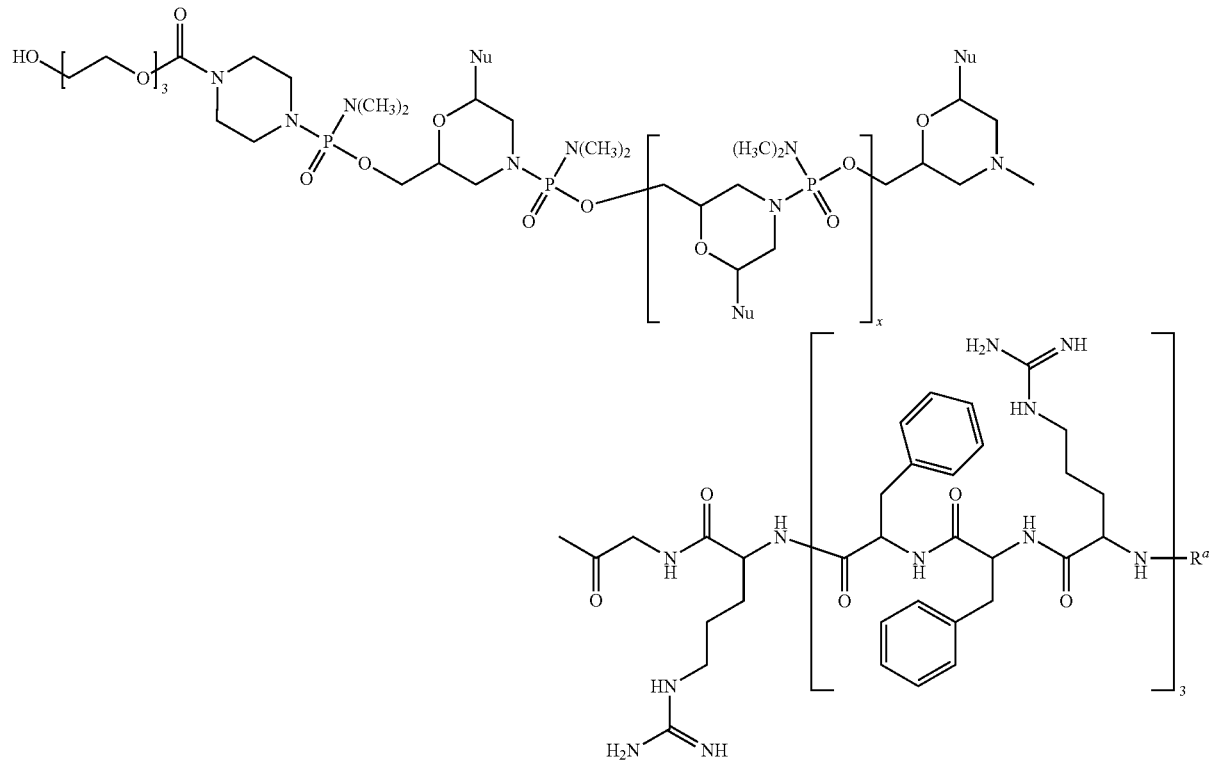

(VII E)

or a pharmaceutically acceptable salt thereof, wherein $R^a$ is H or acetyl, and the targeting sequence consists of SEQ ID NO: 11 (TCA AGT TTT CC) wherein X is 9.

32. The antisense oligomer of claim 13, wherein the antisense oligomer is:

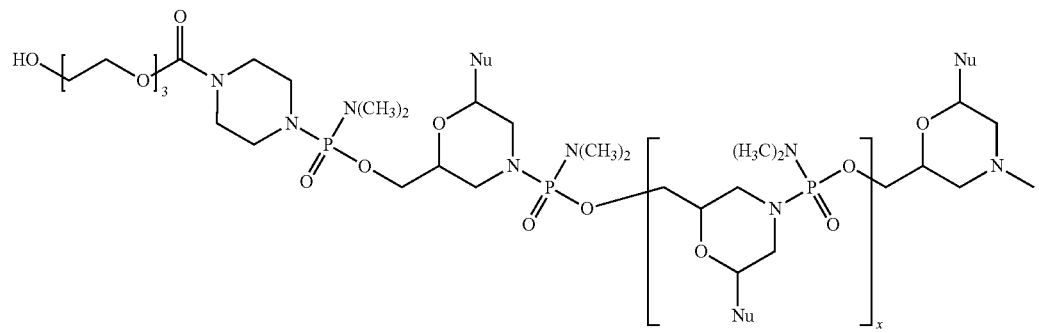

(VII E)

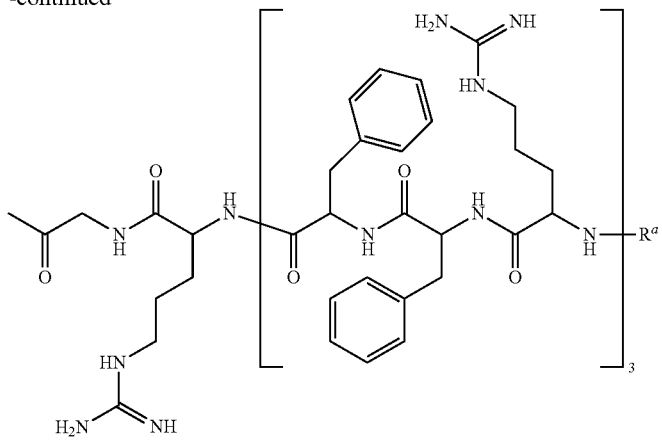
or a pharmaceutically acceptable salt thereof, wherein $R^a$ is H or acetyl, and the targeting sequence consists of SEQ ID NO: 12 (TCC TTT TAT TC) wherein X is 9.
33. The antisense oligomer of claim 13, wherein the antisense oligomer is:
(VII E)
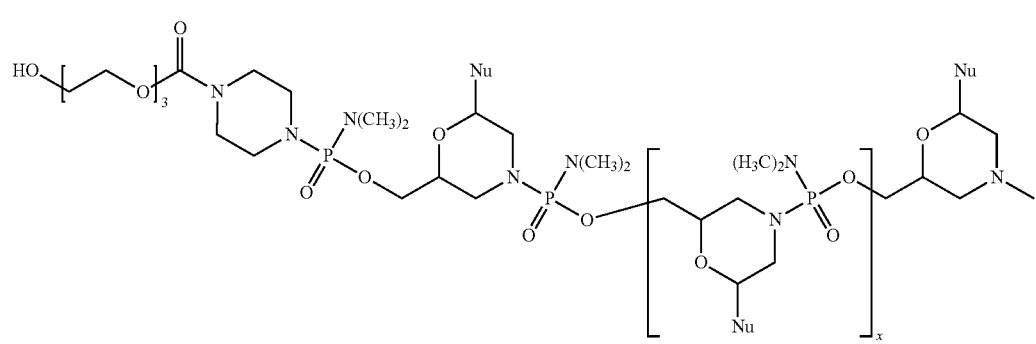
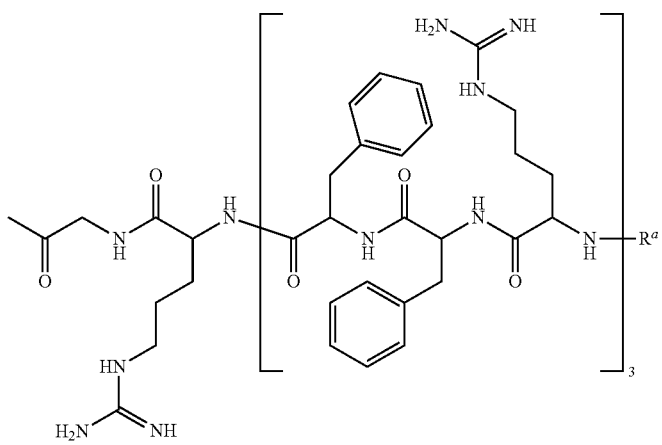

or a pharmaceutically acceptable salt thereof, wherein R<sup>a</sup> is H or acetyl, and the targeting sequence consists of SEQ ID NO: 13 (CCA TCA AGT TT) wherein X is 9.

34. The antisense oligomer of claim 13, wherein the antisense oligomer is:

(VII E)

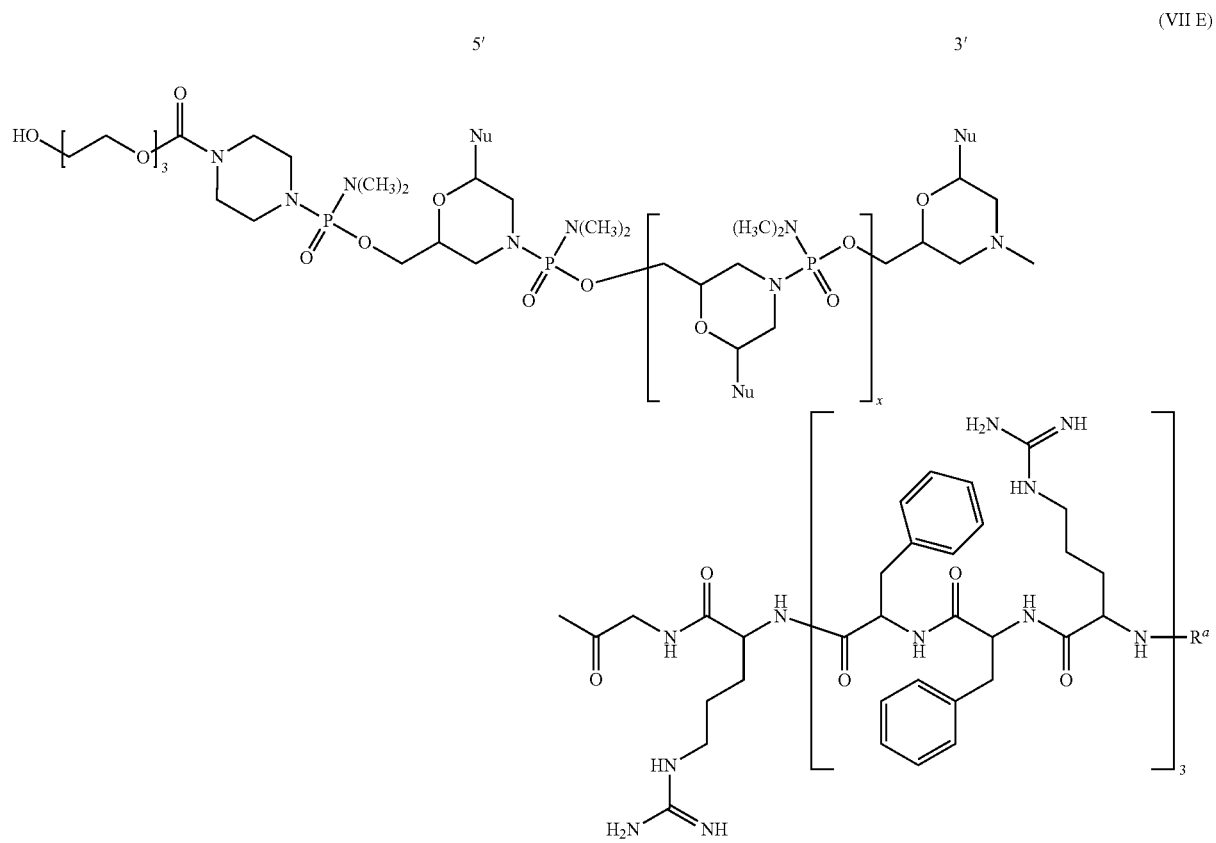

or a pharmaceutically acceptable salt thereof, wherein R<sup>a</sup> is H or acetyl, and the targeting sequence consists of SEQ ID NO: 14 (GGC AAT TCC AT) wherein X is 9.

35. The antisense oligomer of claim 13, wherein the antisense oligomer is:

(VII D)

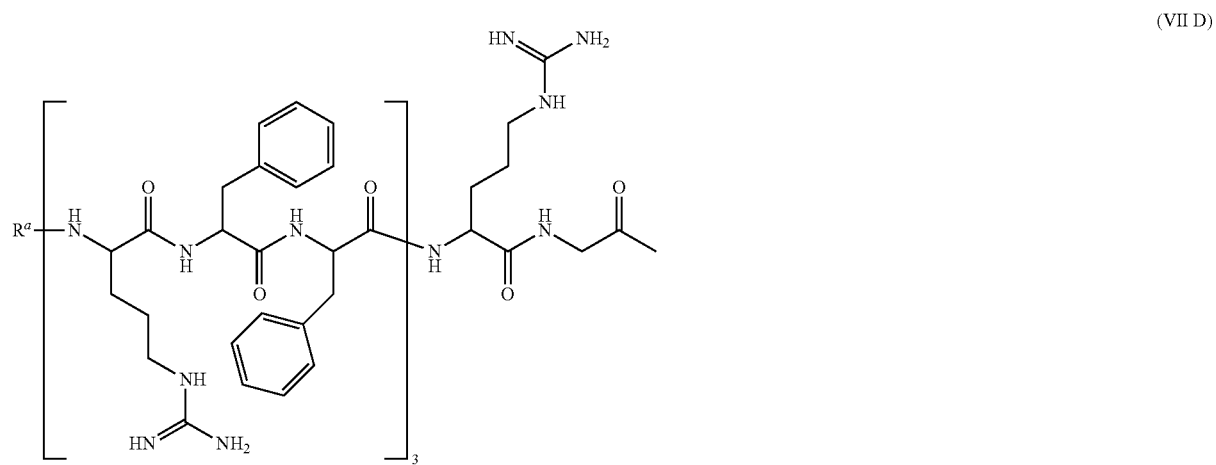

-continued
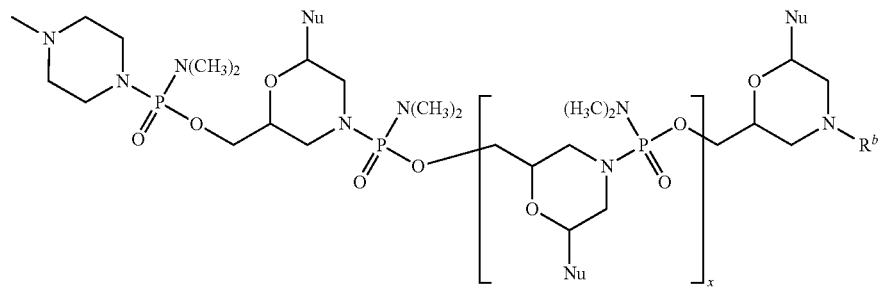
or a pharmaceutically acceptable salt thereof, wherein $R^a$ is H or acetyl, and the targeting sequence consists of SEQ ID NO: 11 (TCA AGT TTT CC) wherein X is 9.
36. The antisense oligomer of claim 13, wherein the antisense oligomer is:
(VII D)
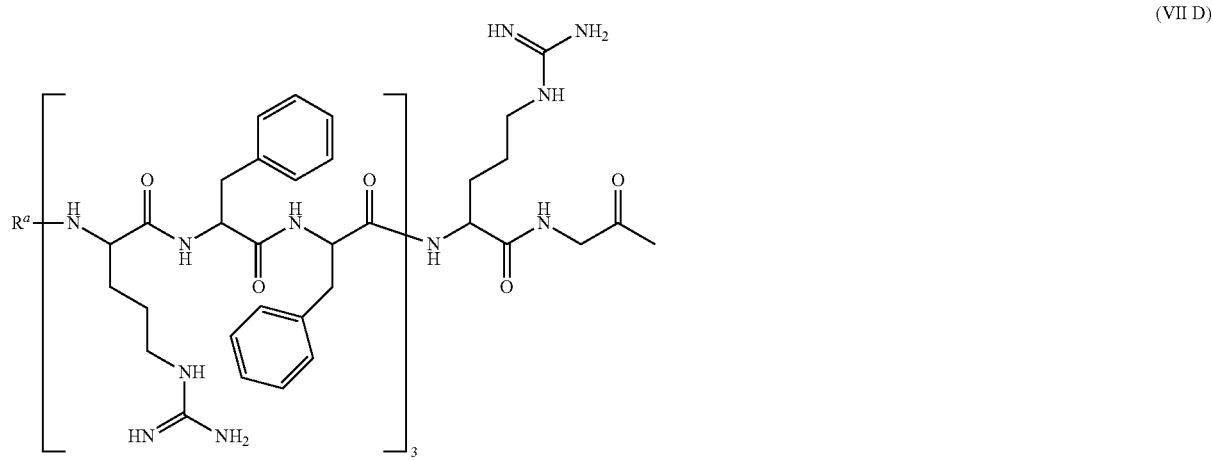
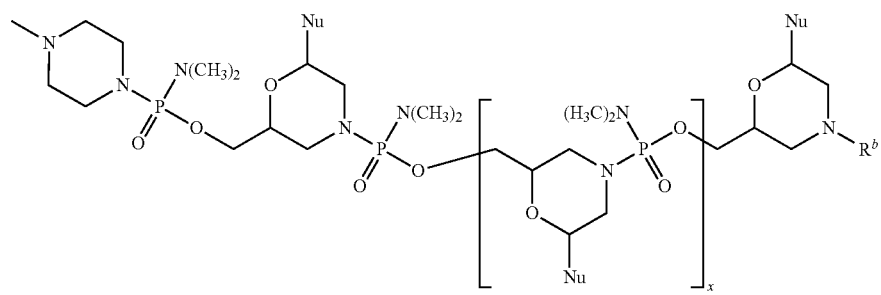

or a pharmaceutically acceptable salt thereof, wherein $R^a$ is H or acetyl, and the targeting sequence consists of SEQ ID NO: 12 (TCC TTT TAT TC) wherein X is 9.

37. The antisense oligomer of claim 13, wherein the antisense oligomer is:

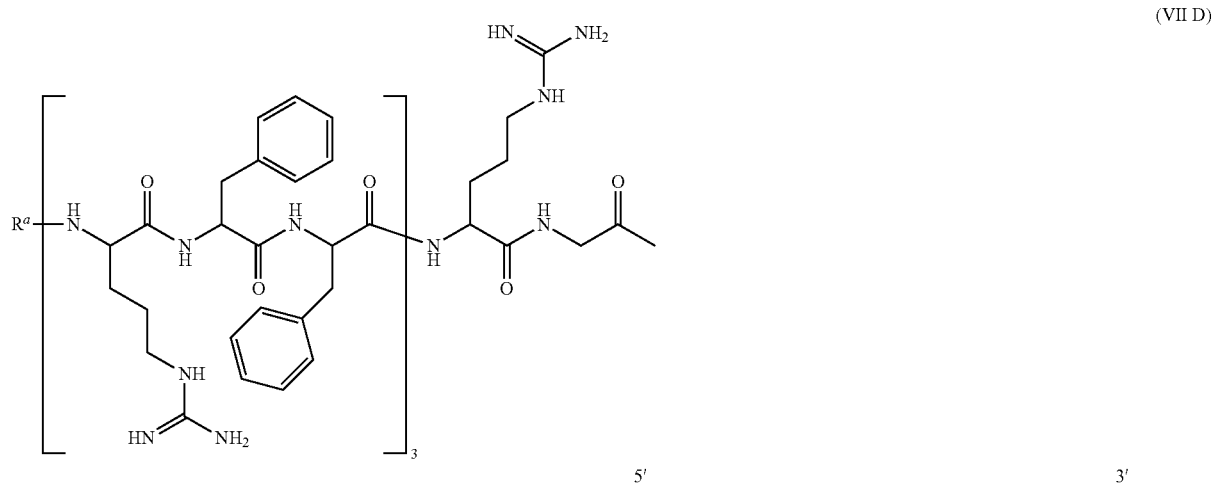

(VII D)

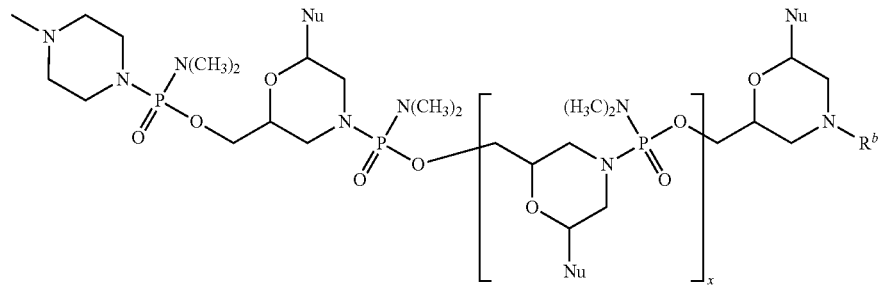

or a pharmaceutically acceptable salt thereof, wherein $R^a$ is H or acetyl, and the targeting sequence consists of SEQ ID NO: 13 (CCA TCA AGT TT) wherein X is 9.

38. The antisense oligomer of claim 13, wherein the antisense oligomer is:

(VII D)

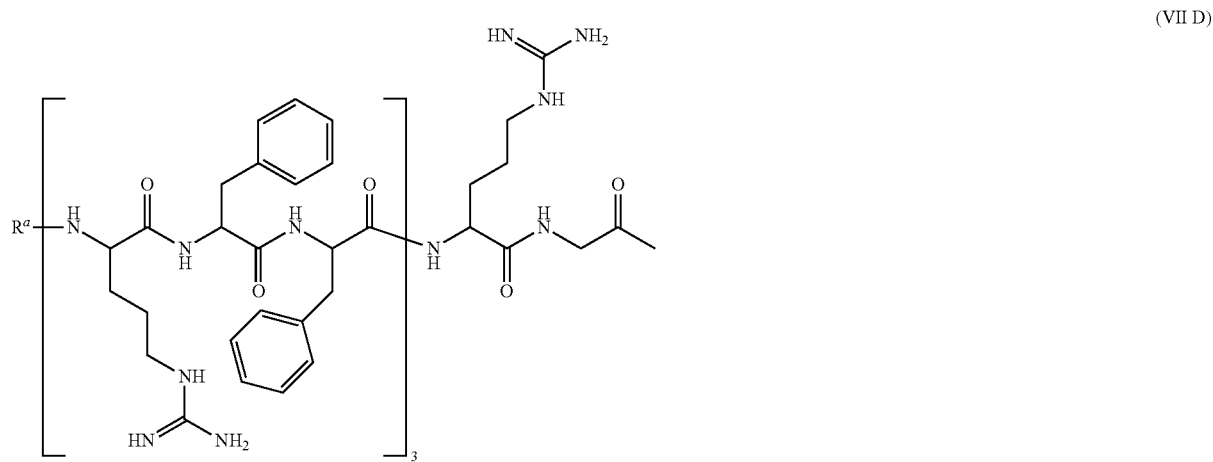

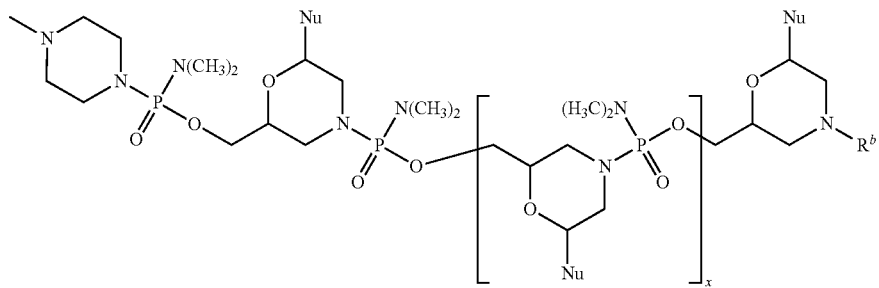
or a pharmaceutically acceptable salt thereof, wherein $R^a$ is H or acetyl, and the targeting sequence consists of SEQ ID NO: 14 (GGC AAT TCC AT) wherein X is 9.
* * * * *

UNITED STATES PATENT AND TRADEMARK OFFICE
CERTIFICATE OF CORRECTION

PATENT NO. : 9,790,495 B2
APPLICATION NO. : 14/713857
DATED : October 17, 2017
INVENTOR(S) : Bruce L. Geller et al.

Page 1 of 1

It is certified that error appears in the above-identified patent and that said Letters Patent is hereby corrected as shown below:

In the Specification

Please insert the following section on Column 1, Line 1:
--STATEMENT OF GOVERNMENT LICENSE RIGHTS
This invention was made with U.S. Government support under grant numbers R21 AI098724, R33 AI098724, R21 AI105980, R33 AI105980, R21 AI111753, R33 AI111753, and R21 AI103653 awarded by National Institutes of Health. The government has certain rights in the invention.--

Signed and Sealed this
Twelfth Day of December, 2017

Joseph Matal
*Performing the Functions and Duties of the
Under Secretary of Commerce for Intellectual Property and
Director of the United States Patent and Trademark Office*

UNITED STATES PATENT AND TRADEMARK OFFICE
CERTIFICATE OF CORRECTION

| | |
|---|---|
| PATENT NO. | : 9,790,495 B2 |
| APPLICATION NO. | : 14/713857 |
| DATED | : October 17, 2017 |
| INVENTOR(S) | : Bruce L. Geller et al. |

It is certified that error appears in the above-identified patent and that said Letters Patent is hereby corrected as shown below:

In the Specification

In Column 1, Line 1, after "STATEMENT OF GOVERNMENT LICENSE RIGHTS", delete paragraph and insert:
--This invention was made with government support under grant number AI105980 awarded by The National Institutes of Health. The government has certain rights in the invention.-- therefor.

Signed and Sealed this
Seventh Day of July, 2020

Andrei Iancu
*Director of the United States Patent and Trademark Office*